(12) United States Patent
Wurtman et al.

US008518882B2

(10) Patent No.: US 8,518,882 B2
(45) Date of Patent: Aug. 27, 2013

(54) METHODS AND COMPOSITIONS FOR AMELIORATING OR INHIBITING DECLINE IN MEMORY OR INTELLIGENCE OR IMPROVING SAME

(75) Inventors: Richard Wurtman, Boston, MA (US); Lisa A. Teather, St. Catharines (CA)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 11/341,912

(22) Filed: Jan. 30, 2006

(65) Prior Publication Data

US 2006/0241077 A1    Oct. 26, 2006

Related U.S. Application Data

(63) Continuation-in-part of application No. 11/224,311, filed on Sep. 13, 2005, which is a continuation-in-part of application No. 10/972,777, filed on Oct. 26, 2004, which is a continuation-in-part of application No. 10/941,025, filed on Sep. 15, 2004, which is a continuation-in-part of application No. 09/363,748, filed on Jul. 30, 1999, now Pat. No. 6,989,376, application No. 11/341,912, which is a continuation-in-part of application No. 10/944,269, filed on Sep. 20, 2004, which is a continuation-in-part of application No. 09/363,748, filed on Jul. 30, 1999, now Pat. No. 6,989,376.

(60) Provisional application No. 60/095,002, filed on Jul. 31, 1998.

(51) Int. Cl.
| A61K 38/27 | (2006.01) |
| A61K 31/70 | (2006.01) |
| A61K 31/14 | (2006.01) |
| A61P 5/06 | (2006.01) |
| A01N 43/04 | (2006.01) |
| A01N 33/12 | (2006.01) |

(52) U.S. Cl.
USPC ............... 514/11.3; 514/50; 514/51; 514/642

(58) Field of Classification Search
USPC ............................................. 514/49, 50, 51
See application file for complete search history.

(56) References Cited

U.S. PATENT DOCUMENTS

| 4,221,784 A | 9/1980 | Growdon et al. | |
| 4,609,647 A | 9/1986 | Growdon et al. | |
| 4,960,759 A | 10/1990 | De Luca et al. | |
| 4,994,442 A | 2/1991 | Gil et al. | |
| 5,141,943 A | 8/1992 | Naguib et al. | |
| 5,470,838 A * | 11/1995 | von Borstel et al. | 514/50 |
| 5,567,689 A | 10/1996 | Sommadossi et al. | |
| 5,583,117 A * | 12/1996 | von Borstel et al. | 514/50 |
| 5,601,829 A | 2/1997 | Quintanilla-Almagro | |
| 5,700,590 A | 12/1997 | Masor et al. | |
| 5,723,449 A | 3/1998 | Sommadossi et al. | |
| 5,962,459 A * | 10/1999 | Piazza et al. | 514/269 |
| 5,977,174 A | 11/1999 | Bradley et al. | |
| 6,191,154 B1 | 2/2001 | Landreth et al. | |
| 6,258,795 B1 * | 7/2001 | von Borstel et al. | 514/49 |
| 6,274,563 B1 * | 8/2001 | von Borstel et al. | 514/50 |
| 6,316,426 B1 * | 11/2001 | von Borstel et al. | 514/50 |
| 6,472,378 B2 * | 10/2002 | von Borstel | 514/50 |
| 6,989,376 B2 * | 1/2006 | Watkins et al. | 514/50 |
| 7,105,498 B2 * | 9/2006 | von Borstel et al. | 514/49 |
| 8,143,234 B2 * | 3/2012 | Wurtman et al. | 514/49 |
| 8,314,064 B2 * | 11/2012 | Watkins et al. | 514/8.4 |
| 2001/0005719 A1 * | 6/2001 | von Borstel | 514/49 |
| 2002/0028787 A1 | 3/2002 | Watkins et al. | |
| 2003/0114415 A1 * | 6/2003 | Wurtman et al. | 514/51 |

FOREIGN PATENT DOCUMENTS

| DE | 2508474 | | 9/1976 |
| DE | 2629845 | | 1/1978 |
| DE | 9412374 | | 9/1994 |
| EP | 0178267 | | 4/1986 |
| EP | 0178267 | A2 * | 4/1986 |
| EP | 0 462 075 | | 12/1991 |
| EP | 0 348 360 | | 1/1994 |
| GB | 2265072 | | 9/1993 |
| JP | 07/215879 | A1 * | 8/1985 |
| JP | 07/215879 | A * | 8/1995 |
| JP | 09/30976 | A2 * | 2/1997 |
| JP | 09285267 | | 11/1997 |
| JP | 09323979 | | 12/1997 |
| JP | 2001/33776 | A2 * | 8/2001 |
| JP | 2001/233776 | A2 | 8/2001 |
| JP | 2001/233776 | A2 * | 8/2001 |

(Continued)

OTHER PUBLICATIONS

Page et al., "Developmental Disorder Associated with Increased Cellular Nucleotidase Activity," ☐☐ Proc. National Academy of Sciences USA, 94(21), 11601-11606 (Oct. 14, 1997).*
Merlini et al., "Effects of . . . Cytidine and.Uridine in Elderly Patients with . . . Metabolic Insufficiency," Gazzetta Medica Italiana Archivio Scienze Mediche, 145(6), 379-390 (Jun., 1966); ☐☐ Biological Abtracts, 83, Abstract No. 27367 (1987).*
Page et al., "Developmental Disorder Associated withftased Cellular Nucleotidase Activity," ☐☐ Proc. National Academy of Sciences USA, 94(21), 11601-11606 (Oct. 14, 1997).*
Coirault et al., "Uridine 5-Triphosphate in Therapy. I. Cure of Neurogenic Muscular Atrophy," ☐☐ La Presse Medicale(Fr.), 68(29), 1127-1129 (Jun. 11, 1960); ☐☐ Chemical Abstracts, 57(7), p. 73, Abstract No. 10485f (Oct. 1, 1962).*

(Continued)

*Primary Examiner* — Lawrence E Crane
(74) *Attorney, Agent, or Firm* — Pearl Cohen Zedek Latzer, LLP

(57) ABSTRACT

The present invention is directed to methods of ameliorating hippocampal dysfunction and improving or inhibiting decline in intelligence or cognitive or hippocampal-dependent memory of a subject and of increasing synthesis and release of neurotransmitters, neurite outgrowth, and levels of neurofilament proteins in the brain and CNS of a subject, comprising administering to the subject a uridine, an acyl derivative thereof, a uridine phosphate, uracil, or a salt thereof.

6 Claims, 30 Drawing Sheets

(56) References Cited

FOREIGN PATENT DOCUMENTS

| JP | 2001233776 A2 | * | 8/2001 |
|---|---|---|---|
| RU | 2003332 C1 | | 11/1993 |
| WO | W O 89/03837 A1 | | 5/1989 |
| WO | WO89/03837 A1 | * | 5/1989 |
| WO | WO 95/05180 | | 2/1995 |
| WO | W O 97/43899 A1 | | 11/1997 |
| WO | WO97/43899 A1 | * | 11/1997 |
| WO | W O 97/45127 A1 | | 12/1997 |
| WO | WO97/4517 A1 | * | 12/1997 |
| WO | WO 97/45127 | | 12/1997 |
| WO | WO97/45127 A1 | * | 12/1997 |
| WO | WO 00/06174 | | 2/2000 |
| WO | WO 00/11952 | | 3/2000 |
| WO | WO00/50043 A1 | * | 8/2000 |
| WO | WO 2005/079250 A2 | | 9/2005 |
| WO | WO 2005/112635 A | | 12/2005 |
| WO | WO 2006/031683 | | 3/2006 |
| WO | WO 2006/127620 | | 11/2006 |

OTHER PUBLICATIONS

Merlini et al., "Effects of . . . Cytidine and Uridine in Elderly Patients with . . . Metabolic Insufficiency," Gazzetta Medica Italiana Archivio Scienze Mediche, 145(6), 379-390 (Jun., 1966); ☐☐ Biological Abtracts, 83, Abstract No. 27367 (1987).*
Gallai et al. (I), "Effects of Uridine in the Treatment of Diabetic Neuropathy: An Electrophysiological Study," ☐☐ Acta Neurol. Scand., 86(1), 3-7 (1992); ☐☐ Biological Abtracts, 94, Abstract No. 112030 (1992).*
Page et al., "Developmental Disorder Associated with Increased Cellular Nucleotidase Activity," Proc. National Academy of Sciences USA, 94(21), 11601-11606 (Oct. 14, 1997).*
Coirault et al., "Uridine 5-Triphosphate in Therapy. I. Cure of Neurogenic Muscular Atrophy," La Presse Medicale(Fr.), 68(29), 1127-1129 (Jun. 11, 1960); Chemical Abstracts, 57(7), p. 73, Abstract No. 10485f (Oct. 1, 1962).*
Merlini et al., "Effects of . . . Cytidine and Uridine in Elderly Patients with . . . Metabolic Insufficiency," Gazzetta Medica Italiana Archivio Scienze Mediche, 145(6), 379-390 (Jun., 1966); Biological Abtracts, 83, Abstract No. 27367 (1987).*
Gallai et al. (I), "Effects of Uridine in the Treatment of Diabetic Neuropathy: An Electrophysiological Study," Acta Neurol. Scand., 86(1), 3-7 (1992); Biological Abtracts, 94, Abstract No. 112030 (1992).*
Gallai et al. (II), "Multi-Infarct Dementia: Modification . . . Patients Treated . . . Cytidine and Uridine," Rivista di Neuropsichiatria e Science Affini, 41(1), 1-9 (1995); BIOSIS, 1996, Abstt Citation No. 466219; only abstract supplied.*
Drago et al., "Memory Deficits of Aged Male Rats Can Be Improved by Pyrimidine Nucleosides and N-Acetylglutamine," Clinical Neuropharmacology, 13(4), 290-296 (1990); Biological Abstracts, 90, Abstract No. 91117 (1990).*
Manna et al., "Effects of Short-Term Administration of Cytidine, Uridine and L-Glutamine . . . Patients with Chronic Cerebrovascular Disease," Intl. J. Clinical Pharmacology Res., 8(3), 199-210 (1988); Biological Abstracts, 86, Abstract No. 51989 (1988).*
Keilbaugh et al., "Anti-Hiv Type 1 Therapy and Peripheral Neuropathy: Prevention of 2', 3'-Dideoxycytidine Toxicity . . . By Uridine and Pyruvate," Molecular Pharamcology, 44(4), 702-706 (Oct. 1, 1993); Biosis, 1994, Abstract No. 413648.*
Popov et al., "Protective Effect of Uridine on D-Galactosamine-Induced Deficiency in Brain Uridine Phosphates," Biomedica Biochimica Acta, 43(12), 1399-1404 (1984); Biological Abstracts, 80, Abstract No. 34525 (1985).*
Ingraham et al., "Nucleoside Diphosphokinase from Salmonella . . . ," Chapter 48 et seq. In Methods in Enzymology, Ll(vol. 51), Hoffee et al. (eds.), New York, NY, 1978, Academic Press, only pp. supplied were 371, 375 305, 306, 318, 327, 329 and 330.*

Miyazaki et al., "Effects of Nucleotides on Learning and Memory in a Morris Water Maze Test in Normal and Basal Forebrain-Lesioned Rats," Life Sciences, 64(1), 45-52 (Nov. 27, 1998).*
Entingh et al., "Brain Uridine Monophosphate: Reduced Incorporation of Uridine During Avoidance Learning," Brain Research, 70(1), 131-138 (Apr. 12, 1974); only abstract supplied.*
Ruthrich et al., "Increase of Guanosine Incorporation into RNA of . . . Application of Uridine Monophosphate During a Learning Experiments," Brain Research, 69(1), 49-55 (Mar. 29, 1974);.*
Ott et al. (I), "Effects of RNA Precursors on Development and Maintenance of Long-Term Memory," Psychopharmacologia, 28(2), 195-204 (1973); Chemical Abstracts, 78(19), p. 77, Abstr. No. 119731q, (May 14, 1973).*
Ott et al. (II), "Influence of 6-Azauridine on Facilitation of Relearning by Precursors of Ribonucleic Acid," Psychopharmacologia, 23(3), 272-278 (1972); Chemical Abstracts, 76(25), p. 103, Abstr. No. 149588z, (Jun. 19, 1972).*
A. Lehninger, Biochemistry, Second Edition, Worth Publishers, Inc., New York, NY, Jul., 1978, only pp. 735-737 supplied.*
Gibbons et al., Biochemistry of Cholesterol, Elsevier Biomedical Press, New York, NY, 1982, only pp. 258 and 259 supplied.*
Lodish et al., Molecular Cell Biology, W. H. Freeman & Co., New York, NY, 2000, only pp. 68-78 supplied, see especially pp. 75-76.*
Zaffaroni et al., "Adrenal Conversion of C14 Labeled Cholesterol and Acetate to Adrenal Cortical Hormones," Journal of the American Chemical Society, 73, 1390-1391 (Mar., 1951).*
Kato et al., "Determinants of Sex Hormone Levels in Men as Useful Indices in Hormone-Related Disorders," Journal of Clinical Epidemiology, 45(12), 1417-1421 (Dec., 1992).*
Marcus et al., "Water Soluble Vitamins," Ch. 63 in Goodman & Gilman's The Pharmacological Basis of Therapeutics, 8th Edition, Pergamon Press, Elmsford, NY, 1990, only pp. 1530 and 1542-1544 supplied.*
Sitaram et al., "Human Serial Learning: Enhancement with Arecholine and Choline and Impairment with Scopolamine," Science, 201, 274-276 (Jul., 1978).*
Beers et al. (eds.), a portion of "Nutritional Disorders," Chapter 1 in the Merck Manual of Diagnosis and Therapy, 17th Edition, Merck & Co., Inc., Rahway, NJ, Jan., 1999, only title and text pp. 1 & 12-21 supplied.*
Albright et al., "Choline Availability Alters Embryonic Development of the Hippocampus and Septum in the Rat," Developmental Brain Research, 113, 13-20 (1999); reference cited by applicant in the response of Aug. 14, 2007, copy supplied as a courtesy.*
Merlini et al., "Effects of Large Doses of Pyrimidine Nucleosides Cytidine and Uridine in Elderly Patients with Neuropsychological Disturbances Caused by Vascular and Cerebral Metabolic Insufficiency," Gazzetta Medica Italiana Archivio Scienze Mediche, 145(6), 379-390 (Jun., 1966); Biological Abtracts, 83, Abstract No. 27367 (1987).
Gallai et al. (II), "Multi-Infarct Dementia: Modification of the P300 Cognitive Event-Related Potential in Patients Treated with the Association of Cytidine and Uridine," Rivista di Neuropsichiatria e Science Affini, 41(1), 1-9 (1995); Biosis, 1996, Abstract Citation No. 466219; only Abstract supplied.
Drago et al., "Memory Deficits of Aged Male Rats Can Be Improved by Pyrimidine Nucleosides and N-Acetylglutamine, " Clinical Neuropharmacology, 13 (4), 290-296 (1990); Biological Abstracts, 86, Abstarct No. 91117 (1990).
Manna et al., "Efects of Short-Term Administration of Cytidine, Uridine and L-Glutamine Alone or in Combination on the Cerebral Electrical Activity of Patients with Chronic Cerebrovascular Disease," Intl. Journal Clinical Pharmacology Research, 8 (3), 199-210 (1988); Biological Abstracts, 86, Abstract No. 51989 (1988).
Keilbaugh et al., "Anti-Human Immunodeficiency Virus Type 1 Therapy and Peripheral Neuropathy: Prevention of 2', 3'-Dideoxycytidine Toxicity in PC12 Cells, a Neuronal Model, by Uridine and Pyruvate, " Molecular Pharmacology, 44 (4), 702-706 Oct. 1, 1993); BIOSIS, 1994, Abstract Citation No. 413648.
Popov et al., "Protective Effect of Uridine on D-Galactosamine-Induced Deficiency in Brain Uridine Phosphates, " Biomedica Biochimica Acta, 43 (12), 1399-1404 (1984); Biological Absracts, 80, Abstract No. 34525 (1985).

Ingraham et al., "Nucleoside Diphosphokinase from *Salmonella typhimurium*, " Chapter 48 in *Methods in Enzymology, LI (vol. 51)*, Hoffee et al., (eds.), New York, NY, 1978, Academic Press, only pages 371 and 375 supplied; asorted portions of other chapters were also supplied including pages 305, 306, 318, 327, 329, and 330.

Entingh et al., "Brain Uridine Monophosphate: Reduced Incorporation of Uridine During Avoidence Learning, " *Brain Reasearch, 70* (1), 131-138 (Apr. 12, 1974; only abstract supplied.

Rüthrich et al., "Increase of Guanosine Incorporation into RNA of Hippocampal Neurons by Application of Urodine Monophosphate During a Learning Experiments, " *Brain Research, 69* (1), 49-55 Mar. 29, 1974); only abstact supplied.

Ott et al. (I), "Effects of RNA Precursors on Development and Maintenance of Long-Term Memory, " *Psychopharmacolgia, 28* (2), 195-204 (1973); *Chemical Abstracts, 78* (19), p. 77, Abstr. No. 119731q, (May 14, 1973).

Ott et al. (II), "Influence of 6-Azauridine on Facilitation of Releasing by Precursors of Ribonucleic Acid, " *Psychopharmacologia, 23* (3), 272-278 (1972); *Chemical Abstracts, 76* (25), p. 103, Abstr. No. 149588z, (Jun. 19, 1972).

A. Lehninger, *Biochemistry, Second Edition*, Worth Publishers, Inc. New York, NY, Jul., 1978, only pages 735-737 supplied.

Gibbons et al., *Biochemistry of Cholesterol*, Elsevier Biomedical Press, New York, NY, 1982, only pages 258 and 259 supplied.

Lodish et al., *Molecular Cell Biology*, W. H. Freeman & Co., New York, NY, 2000, only pages 68-78 supplied, se especially pp. 75-76.

Zaffaroni et al., "Adrenal Conversion of C $^{14}$ Labeled Choleserol and Acetate to Adenal Cortical Hormones, " *Journal of the American Chemical Society, 73*, 1390-1391 (Mar., 1951).

Kato et al., "Determinants of Sex Hormone Levels in Men as Useful Indices in Hormone-Related Disorders, " *Journal of Clinical Epidemiology, 45* (12), 1417-1421 (Dec., 1992).

Marcus, et al. (1990) "Water soluble vitamins" Ch. 63 in Goodman & Gilman's The Pharmacological Basis of Therapeutics 1530 and 154-1544.

Sitaram, et al (1978) "Human Serial Learning: Enhancement with Arecholine and Choline and Impairment with Scopolamine" Science 201, 274-276.

Savendahl, et al (1997) "Prolonged Fasting in Humans Results in Diminished Plasma Choline Concentrations But Does Not Cause Liver Dysfunction" American Journal of Clinical Nutrition, 66, 622-625.

Beers, et al (1999) "The Merck Manual of diagnosis and Therapy " 977, 1025, 1027, 1038, 1471, 1472, 1475 and 2417.

Hull A.M., "Neuroimaging findings in post-traumatic stress disorder." Br. J. Psychiatry. Aug. 2002, vol. 101, pp. 102-110; abstract.

Pawlak R et al. "Tissue plasminogen activator and plasminogen mediate stress- induced decline of neuronal and cognitive functions in the mouse hippocampus." Proc. Natl. Acad. Sci. USA. Dec. 13, 2005, vol. 102, No. 50, pp. 18201-18206; abstract.

Judith Wurtman; Sources of Choline and Lecithin in the Diet, Nutrition & The Brain, vol. 5, A. Barbeau, J.H. Growdon, & R.J. Wurtman, Eds., Raven Press, New York, 1979, pp. 73-81.

Supplementary European Search Report of corresponding European Application No. 05796529, dated Jan. 20, 2011.

Office Action of the corresponding Chinese patent application No. 200780039887.3 dated Jul. 21, 2010.

Chen T-H et al.: "A nucleoside-nucleotide mixture may reduce memory deterioration in old senescence-accelerated mice." Journal of Nutrition 2000 US, vol. 130, No. 12, 2000, pp. 3085-3089.

Liu L-S et al.: "Uridine prodrug PN401 improves memory in APP2576 mice that model Alzheimer's disease and uridine decreases cell death due to chemical hypoxia in fibroblasts from patients with sporadic AD." Journal of Neurological Sciences; $3^{rd}$ International Congress on Vascular Dementia; Prague, Czech Republic; Oct. 23-26, 2003, Elsevier Scientific Publishing Co, Amsterdam, NL, vol. 229, No. Special Issue SI, Mar. 1, 2005, pp. 316-317.

Villardita C et al.: "Effects of pyrimidine nucleosides and N-acetylglutamine on learning and memory processes in men of various ages." Acta Therapeutica, XX, XX, vol. 9, No. 4, Jan. 1, 1983, pp. 407-416.

De Bruin N M W J et al,: "Combined uridine and choline administration improvies cognitive deficits in spontaneously hypertensive rats." Neurobiology of Learning and Memory 200307 US LNKD-D0I:10.1016/S1074-7427(03) 00024-8, vol. 80, No. 1, Jul. 2003, pp. 63-79.

Extended European Search Report and Search Opinion for corresponding EP application No. 07717110.6, dated Oct. 14, 2010.

Teather L-A et al.: "Chronic administration of UMP ameliorates the impairment of hippocampal-dependentmemory in impoverished rats." Journal of Nutrition, vol. 136, No. 11, Nov. 2006. pp. 2834-2837.

International Preliminary Report on Patentability for corresponding PCT application No. PCT/US05/32312, dated Oct. 4, 2010.

Cacabelos R. et al, "Therapeutic effects of CDP-Choline in Alzheimer's disease cognition, brain mapping, cerebrovascular hemodynamics, and immune factors." Annals New York Academy of Sciences, 777:399-403.

Franco-Maside A. et al: "Brain Mapping Activity and Mental Performance After Chronic Treatment with CDP-Choline in Alzheimer's Disease," Methods and Findings in Experimental and Clinical Pharmacology, Prous, Barcelona, ES, vol. 16, No. 8, Jan. 1, 1994, pp. 597-607.

Supplementary European Search Report of corresponding European Application No. 07 83 7399, dated Nov. 26, 2010.

Extended European Search Report of corresponding EP Application No. 10075660 dated Jun. 20, 2011.

Extended European Search Report of corresponding EP Application No. 10075661 dated Jun. 20, 2011.

Piccoli F et al., "CDP-choline in the treatment of chronic cerebrovasculopathies," Archives of Gerontology and Geriatrics, vol. 18, No. 3, 1994, pp. 161-168.

Karkishchenko N N et al., "Use of uridine as antidepressant—shows its reduced toxicity and elimination of several harmful side effects," DERWENT, 1993, abstract.

Ingraham et al., "Nucleoside Diphosphokinase from *Salmonella typhimurium*, " Chapter 48 in Methods in Enzymoloy, LI(vol. 51), Hoffee et al. (eds.), New York, NY, 1978, Academic Press, only pp.371 and 375 supplied; assorted portions of other chapters were also supplied including pp. 305, 306, 318, 329 and 330.

De Bruin et al, "Effects of Uridine/Cholin on cognative deficits in spontaneously hypersensative rats" Program No. 184. 16. 2002 Abstract Viewer/Itinerary Planner, Washington, DC, Society for Neuroscience, 2002, Online:http//sfn.scholarone.com/ltin2002/index.html Wurtman et al, Effect of oral CDPcholine on plasma choline and uridine levels in humans, Biochem Pharmacol, Oct. 1, 2000;60(7):989-992.

Petersen et al, Mild cognitive impairment: clinical characterization and outcome, Arch Neurol. Mar. 1999;56(3):303-308, Erratum in: Arch Neurol Jun. 1999;56(6):760.

Agnati et al, Intravenous uridine treatment antagonizes hypoglycaemia-induced reduction in brain somatostatin-loke immunoreactivity, Acta Physiol Scand. Apr. 1986;126(4):525-531.

Zaffaroni, et al (1951) "Adrenal Conversion of C14 Labeled Cholesterol and Aceiate to Adrenal Cortical Hormones" Journal of the American Chemical Society, 73, 1390-1391.

Marcus, et al (1990) "Water soluble vitamins" Ch. 63 in Goodman & Gillman's The Pharmacological Basis of Therapeutics 1530 and 1542-1544.

Sitaram, et al (1978) "Human Serial Learning: Enhancement with Arecholine and Choline and impairment with Scopolamin" Science 201,274-276.

Hock, et al (2000) "Increased CSF Levels of Nerve Growth Factor in Patients with Alzheimer's Disease" Neurology 54 2009-2011.

Savendahl, et al (1997) "Prolonged Fasting in Humans Results in Diminshed Plasma Choline Concentraions But Dos Not cause Liver Dysfunction" American Journal of Clinical Nutrition, 65, 622-625.

A Lehninger, Biochemistry, Second edition Worth Publishers, Inc. New York, NY Jul. 1978, pp. 735-737 supplied.

Beers, et al (1999) "The Mercj Manual of Diagnosis and Therapy" 977, 1025, 1027, 1038, 1471, 1472, 1475 and 2417.

Yates, et al., J. Am. Dietetics Assn 98:699-706, Jun. 1998.

Millington & Wurtman, J. Neurochem 38:1748, 1982.

Ross et al., "Phospholipid biosynthetic enzymes in human brain" Lipids 1997;32:351-358.

Cohen et al., JAMA 274:902, 1995.

Weiner et al., American Journal of Public Health, vol. 89, Issue 11 1637-1640, 1999.

Schnider-Helmert and Spinweber, Psychopharmacology (Berl). 1986;89 (1), 1-7.

Cornford et al., Independent blood-brain barrier transport sstems for nucleic acid precursors, Biochim. Biophys Acta, 349:211-219, (Jun. 25, 1975).

Monticone GF, et al., On the therapeutic use of nucleosides, cytidine and uridine, in some neurological diseases. Minvera Med., 57(101): 4348-4352, (Dec. 19, 1966).

Dawson, Enzymatic conversion of uridine nucleotide to cytidinenucleotide by rat brain. J. Neurochem., 15:31-34, (Jan. 1968).

Becfort DM et al., Hereditary orotic aciduria: long-term therapy with uridine and a trial of uracil. Pediair, 75(5): 885-891, (Oct. 1969).

Roberts CA, et al, Uridine anticonvulsant effects: selective control of nucleoside incorporation in experimental epilepsy. Epilepsia, 15(4): 479-500, (Dec. 1974).

Lopez-Coviella et al., Evidence that 5'-cytidinephosphocholine can affect brain phospholipid composition by increasing choline and cytidine plasma levels. J. Neurochemistry, 65: 889-894, (Aug. 1995).

Ginsburg et al., Rodent models of cerebral ischemia. Stroke 20:1627-1642, (Dec. 1989).

Spiers et al, Citicoline imroves verbal memory in aging. Arch Neurol., 53(5): 441-448, May 1996.

Hoffee et al, Purine and pyrimidine nucleotide metabolism. Methods in Enzymology, vol. LI, pages 38-48. 1978, Academic Press, New York.

Camiener, Studies of the Enzymatic deamination of cytosine arabinoside-l, Pharmacology, 14: 1405-1416, Oct. 1965.

Cheal, The Gerbil: A unique Model for Research on Aging, Experimental Aging Res 12 (1): 3-11, Spring 1986.

Vincent, et al, The Pathology of the Mongolian Gerbil (Meriones unguiculatus): A review. Lab Animal Science 2(5): 645-651, Oct. 1979.

Ross et al, Phospholipid Biosynthetic Enzymes in Human Brain, Lipids, 32(4): 351-358, Apr. 1997.

De Bruin et al, "Effects of Uridine/Choline on cognitive deficits in spontaneously hypertensive rats" Program No. 184.16. 2002 Abstract Viewer/Itinerary Planner. Washington, DC: Society for Neuroscience, 2002. Online: http://sfn.scholarone.com/itin2002/index.html.

Connolly et al, Uridine and its nucleotides. biological actions, therapeutic potentials, May 1999, 20: 218-225. Trends Pharmacological Sciences.

Wurtman et al, Effect of oral CDP-choline on plasma choline and uridine levels in humans. Biochem Pharmacol. Oct. 2000 1:60(7):989-992.

Petersen et al, Mild cognitive impairment: clinical characterization and outcome. Arch Neurol. Mar. 1999;56(3):303308. Erratum in: Arch Neurol Jun. 1999;56(6):760.

Agnati et al, Intravenous uridine treatment antagonizes hypoglycaemic-induced reduction in brain somatostatin-like immunoreactivity, Acta Physiol Scand. Apr. 1986;126(4):525-531.

Alvarez, et al (1997) "Citicoline Improves Memory Performance in Elderly Subjects " Meth Find Exp Clin Pharmacol. (19) 3 201-210.

Carabelos, et al "Therapuetic Efects of CDP-Choline in Alheimer's Disease " Anal. Of NY Acad of Sci 399403, vol. 77 (1996).

Petkov, et al "Effects of Cytidine Diphosphate Choline on Rats with Memory Deficits" Drug Research 1993 82-828, vol. 48 (8).

Secades, et al "CDP-Choline: Pharmalogical and Clinical Review" Meth Find Exp Clin Pahrmacol. 1995 17(Suppl B) 1-54.

Teather, et al "Post-training Cyclooxygenase-2 (CO-2) Inhibition Impairs Memory Consolidation" Learning and Memory 41-47. (Jan. 2002), 9(1).

Teather, et al "Dietary CDP-choline supplementation prevents memory impairment caused by impoverished environmental conditions in rats" Learning and Memory 39-43. (Jan. 2005), 12(1).

Weiss, et al. "Metabolism and Actions of CDP Choline as an Endogenous Compund and Administered Exogenously as Citicoline" Life Sciences vol. 56, No. 9 637-660. 1995.

Breckenridge W.C. et al.: "The lipid composition of adult rat brain synaptosomal plasma membranes", Biochim. Biophys. Acta, 1972, 266:695-707.

Choy P. et al.: "An increase in cytoplasmic CTP accelerates the reaction catalysed by CTP: phosphocholine cytidyltransferase in poliovirus-infected HeLa". The Journal of Biological Chemistry, 1980, 255(3): 1070-1073.

Conant R. et al. "Therapeutic Applications of Citicoline for Stroke and Cognitive Dysfunction in the Elderly: A Review of the Literature" Alternative Medicine Review, vol. 9, No. 1, 17-31, 2004.

de la Morena, E., "Efficacy of CDP-choline in the Treatment of Senile Alterations in Memory," Annals NY Acad, Sci 640, 233-236, 1991.

Fioravanti et al., "Cytidinediphosphocholine (CDP-choline) for Cognitive and Behavioural Disturbances Associated with Chronic cCerebral Disorders in the Elderly," Cochrane Database of Systematic Reviews, Issue 2, Art No. CD000269, pp. 1-28, 2005.

Fujio et al., "Enzymatic production of pyrimidine nucleotides using Corynebacterium ammoniagenes cells and recombinant Escherichia coli cells: enzymatic production of CDP-choline from orotic acid and choline chloride (Part I)," Biosci. Biotechnol. Biochem., vol. 61 (6), pp. 956-959. Jun. 1997.

Gallagher et al., "Spatial Learning Deficits in Old Rats: A Model for Memory Decline in the Aged," Neurobiology of Aging. Vo. 9, pp. 549-556, 1988.

Jann et al. "Action of cytidine and uridine in the treatment of neuropsychological syndromes caused by brain diseases of various origins," Minerva Medica, 1969 May 26;60(42):2092-108.

Jansen et al., "Biosynthesis of Phosphatidylcholine from a Phosphocholine Precursor Pool Derived from the Late Endosomal/ Lysosomal Degradation of Sphingomyelin," J. Biological Chemistry, 276(22), 18722-18727, 2001.

Kolanowski et al. "Possibilities of fish oil application for food products enrichment with omega-3 PUFA." Int. J. Food Sci. Nutr. 1999, Jan, 50(1); 39-49.

Lopez G-Coviella et al.: "Enhancement by cytidine of membrane phospholipid synthesis," Journal of Neurochemistry, 1992, 59:338-343.

Mosharrof A. H. et al., "Effects of Meclofenoxate and Citicholine on Learning and Memory in Aged Rats" ACTA Physiologica et Pharmacologica Bulgarica, vol. 13, No. 4 Sofia, 17-24, 1987.

Osada et al., "Changes in serum cholinesterase (EC 3 1 * 1 * 8) activity in rats consuming a high-fat diet," Br. J. Nutr., vol. 62 (2), pp. 343-348, 1989.

Patel, S. V., "Pharmacotherapy of Cognitive Impairment in Alzheimer's Disease: A Review" J. Geriatric Psychiatry and Neurology, 8, 81-95, 1995.

Richardson, I. U. et al., "Stimulation of Cdt-Choline Synthesis by Uridine or Cytidine in PC12 Rat Pheochromocytoma Cells," Brain Research, 971, 161-167, 2003.

Sepe, O., "Effectiveness of the Association of Cytidine and Uridine in Cerebrovascular Conditions," Minerva Medica, 61, 5934-5941 (Dec. 22, 1970), (w/ translation).

Stryer Lubert: "Biochemistry", Third Edition, W.H. Freeman and Company / New York; 1988, p. 550 and p. 609.

Teather L. A. et al., "Dietary Cytidine (5')-diphosphocholine Supplementation Protects against Development of Memory Deficits in Aging Rats," Progress in Neuro-Psychopharmacology & Biological Psychiatry 27, 711-717, 2003.

Terry R.D. et al.: "Physical basis of cognitive alterations in Alzheimer's disease: synapse loss is the major correlate of cognitive impairment". Ann. Neurol., 1991; 30:572-580.

Venes et al. (eds.) Taber's Cyclopedic Medical Dictionary, 19th Edition, F. A. Davis Co., Philadelphia, PA, 2001, See pp. 594 ("differentiation"), 1225 ("Lewy bodies"), and 1656 ("Pick's disease").

International Search Report and Written Opinion of corresponding PCT application PCT/US05/32312 dated Oct. 17, 2006.

International Search Report and Written Opinion of corresponding PCT application PCT/US07/02405 dated Sep. 24, 2007.

International Search Report and Written Opinion of corresponding PCT application PCT/US07/1 8876 dated Sep. 17, 2008.

European Search Report of corresponding EP application EP 07 11 6909 dated Jun. 25, 2008.

European Search Report of corresponding EP application EP 09 17 3495 dated Dec. 14, 2009.
English translation of Office Action issued for corresponding Japanese application No. 2000-562028 dated Nov. 21, 2006.
Petkov V.D. et al., "Effect of CDP-Choline on Learning and Memory Processes in Rodents," Meth Find Exp Clin Pharmacol, 1992. 14(8), pp. 593-605.

Barker et al., "Age-Associated Memory Impairment: Diagnostic and Treatment Issues," International Journal of Geriatric Psychiatry, 8(4), 305-310 (Apr., 1993).
Geiger et al., "Cytidine and Uridine Requirement of the Brain," Journal of Neurochemistry, 1, 93-100 (1956).

* cited by examiner

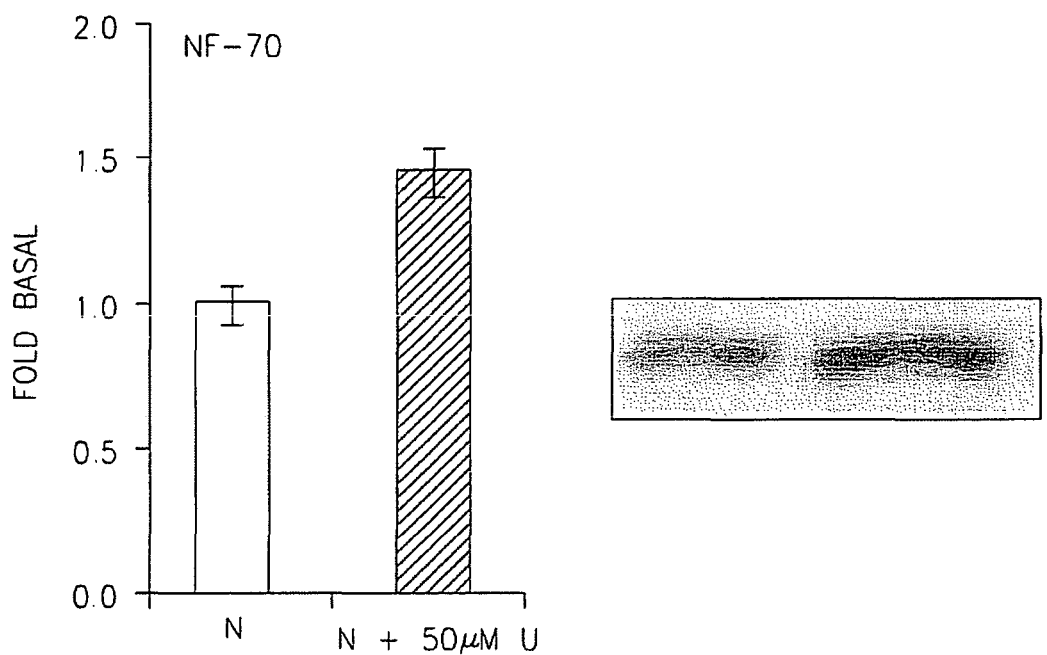
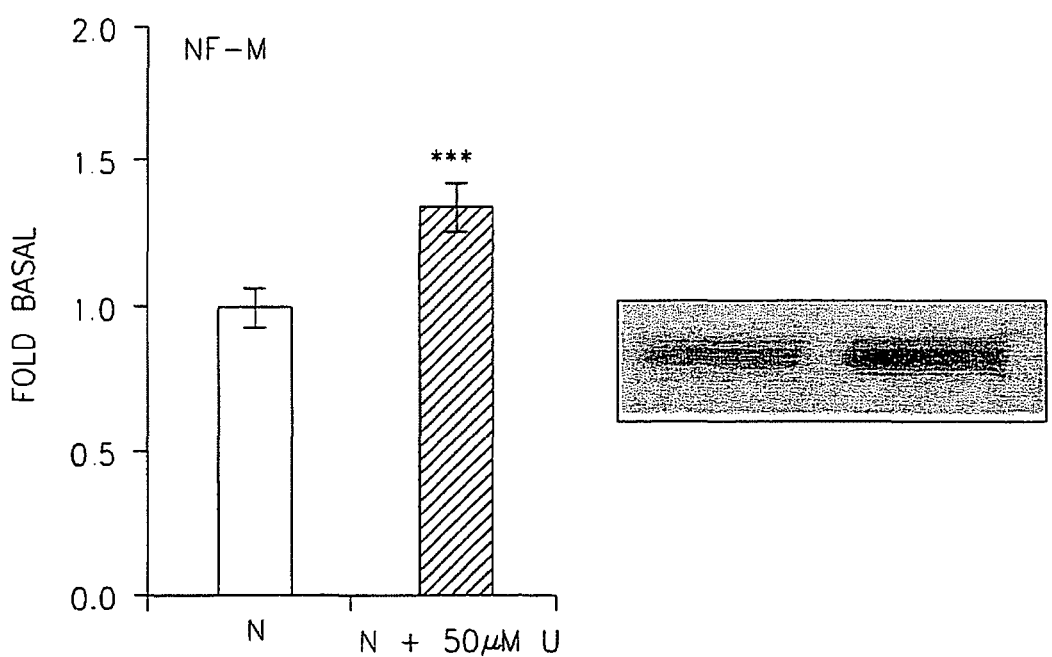
FIG.16E

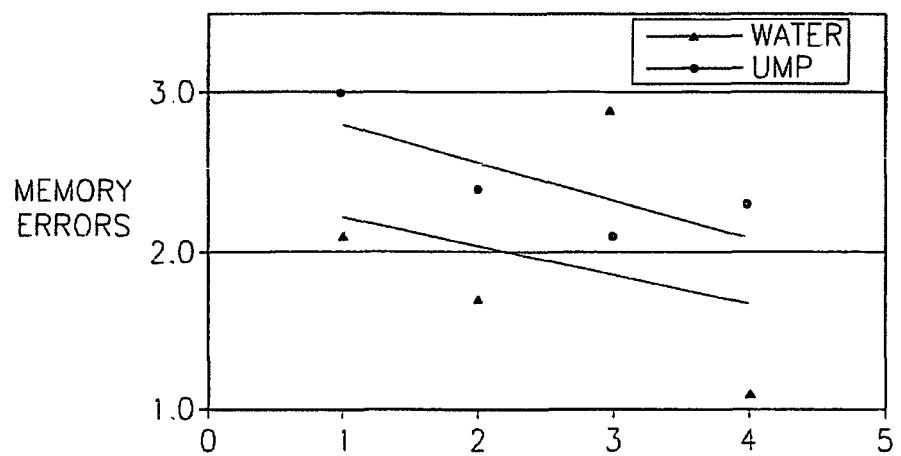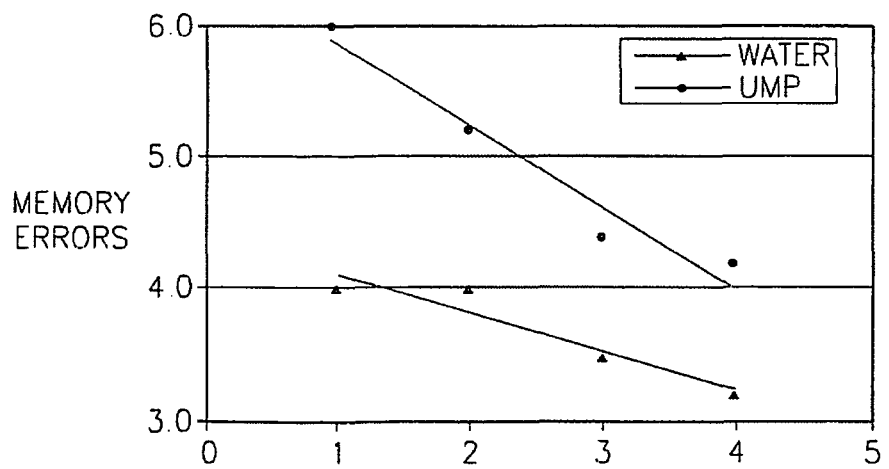
FIG.25

METHODS AND COMPOSITIONS FOR AMELIORATING OR INHIBITING DECLINE IN MEMORY OR INTELLIGENCE OR IMPROVING SAME

CROSS REFERENCE TO RELATED APPLICATIONS

This application is (a) a Continuation-in-Part of U.S. application Ser. No. 11/224,311, filed Sep. 13, 2005, which is a Continuation-in-Part of U.S. application Ser. No. 10/972,777, filed Oct. 26, 2004, which is a Continuation-in-Part of U.S. application Ser. No. 10/941,025, filed Sep. 15, 2004, which is a Continuation-in-Part of U.S. application Ser. No. 09/363,748, filed Jul. 30, 1999, now U.S. Pat. No. 6,989,376, which claims priority from U.S. Provisional Patent Application 60/095,002, filed Jul. 31, 1998; and is also (b) a Continuation-in-Part of U.S. application Ser. No. 10/944,269, filed Sep. 20, 2004, which is a Continuation-in-Part of U.S. application Ser. No. 09/363,748, filed Jul. 30, 1999, now U.S. Pat. No. 6,989,376, which claims priority from U.S. Provisional Patent Application 60/095,002, filed Jul. 31, 1998. These applications are incorporated herein by reference.

STATEMENT REGARDING FEDERALLY SPONSORED RESEARCH OR DEVELOPMENT

The invention described herein was supported in part by grants from The National Institutes of Mental Health (Grant No. 5-R01 MH-28783-24). The government has certain rights in the invention.

FIELD OF THE INVENTION

The present invention is directed to methods of ameliorating hippocampal dysfunction and improving or inhibiting decline in intelligence or cognitive or hippocampal-dependent memory of a subject and of increasing synthesis and release of neurotransmitters, neurite outgrowth, and levels of neurofilament proteins in the brain and CNS of a subject, comprising administering to the subject a uridine, an acyl derivative thereof, a uridine phosphate, uracil, or a salt thereof.

BACKGROUND OF THE INVENTION

Uridine is a pyrimidine nucleoside and is essential in the synthesis of ribonucleic acids and tissue glycogens such as UDP glucose and UTP glucose. Prior medical uses of uridine alone include treatment of genetic disorders related to deficiencies of pyrimidine (synthesis such as orotic aciduria. Choline, a dietary component of many foods, is part of several major phospholipids that are critical for normal membrane structure and function. Choline is included with lipid emulsions that deliver extra calories and essential fatty acids to patients receiving nutrition parenterally.

SUMMARY OF THE INVENTION

The present invention is directed to methods of ameliorating hippocampal dysfunction and improving or inhibiting decline in intelligence or cognitive or hippocampal-dependent memory of a subject and of increasing synthesis and release of neurottansmitters, neurite outgrowth, and levels of neurofilament proteins in the brain and CNS of a subject, comprising administering to the subject a uridine, an acyl derivative thereof, a uridine phosphate, uracil, or a salt thereof.

In one embodiment, the present invention provides a method of ameliorating or inhibiting a decline in a cognitive memory or intelligence of a subject, comprising administering to the subject a uridine, an acyl derivative thereof, a uridine phosphate, uracil, or a salt thereof, thereby ameliorating or inhibiting a decline in a cognitive memory or intelligence of a subject.

In another embodiment, the present invention provides a method of ameliorating or inhibiting a decline in a cognitive memory or intelligence of a subject, comprising administering to the subject a composition comprising (a) a uridine, an acyl derivative thereof, a uridine phosphate, uracil, or a salt thereof; and (b) a choline or salt thereof, thereby ameliorating or inhibiting a decline in a cognitive memory or intelligence of a subject.

In another embodiment, the present invention provides a method of ameliorating or inhibiting a decline in a hippocampal-dependent memory of a subject, comprising administering to the subject a uridine, an acyl derivative thereof, a uridine phosphate, uracil, or a salt thereof, thereby ameliorating or inhibiting a decline in a hippocampal-dependent memory of a subject.

In another embodiment, the present invention provides a method of ameliorating or inhibiting a decline in a hippocampal-dependent memory of a subject, comprising administering to the subject a composition comprising (a) a uridine, an acyl derivative thereof, a uridine phosphate, uracil, or a salt thereof; and (b) a choline or salt thereof, thereby ameliorating or inhibiting a decline in a hippocampal-dependent memory of a subject.

In another embodiment, the present invention provides a method of improving or enhancing a cognitive memory or intelligence, or function of a subject, comprising administering to the subject a uridine, thereby improving or enhancing a cognitive memory or intelligence, or function of a subject. In another embodiment, the present invention provides a method of improving or enhancing a cognitive memory or intelligence, or function of a subject, comprising administering to the subject an acylated uridine compound or acyl derivative of a uridine, thereby improving or enhancing a cognitive memory or intelligence, or function of a subject. In another embodiment, the present invention provides a method of improving or enhancing a cognitive memory or intelligence, or function of a subject, comprising administering to the subject a uridine phosphate, thereby improving or enhancing a cognitive memory or intelligence, or function of a subject. Each possibility represents a separate embodiment of the present invention.

In another embodiment, the present invention provides a method of improving or enhancing a cognitive memory or intelligence of a subject, comprising administering to the subject a composition comprising (a) a uridine; and (b) a choline or salt thereof, thereby improving or enhancing a cognitive memory or intelligence of a subject. In another embodiment, the present invention provides a method of improving or enhancing a cognitive memory or intelligence of a subject, comprising administering to the subject a composition comprising (a) an acylated uridine compound or acyl derivative of a uridine; and (b) a choline or salt thereof, thereby improving or enhancing a cognitive memory or intelligence of a subject. In another embodiment, the present invention provides a method of improving or enhancing a cognitive memory or intelligence of a subject, comprising administering to the subject a composition comprising (a) a uridine phosphate; and (b) a choline or salt thereof, thereby improving or enhancing a cognitive memory or intelligence of a subject. Each possibility represents a separate embodiment of the present invention.

In another embodiment, the present invention provides a method of ameliorating a hippocampal dysfunction in a subject, comprising administering to the subject a uridine, an acyl derivative thereof, a uridine phosphate, uracil, or a salt thereof, thereby ameliorating a hippocampal dysfunction in a subject.

In another embodiment, the present invention provides a method of ameliorating a hippocampal dysfunction in a subject, comprising administering to the subject a composition comprising (a) a uridine, an acyl derivative thereof, a uridine phosphate, uracil, or a salt thereof, and (b) a choline or salt thereof, thereby ameliorating a hippocampal dysfunction in a subject.

In another embodiment, the present invention provides a method of increasing or enhancing an ability of a brain cell or neural cell of a subject to release an effective quantity of dopamine into a synapse, comprising administering to the subject a uridine, an acyl derivative thereof, a uridine phosphate, uracil, or a salt thereof, thereby increasing or enhancing an ability of a brain cell or neural cell of a subject to release an effective quantity of dopamine into a synapse.

In another embodiment, the present invention provides a method of increasing or enhancing an ability of a brain cell or neural cell of a subject to release an effective quantity of dopamine into a synapse, comprising administering to the subject a composition comprising (a) a uridine, an acyl derivative thereof, a uridine phosphate, uracil, or a salt thereof; and (b) a choline or salt thereof, thereby increasing or enhancing an ability of a brain cell or neural cell of a subject to release an effective quantity of dopamine into a synapse.

In another embodiment, the present invention provides a method of increasing a level of acetylcholine in a synapse of a subject, comprising administering to the subject a uridine, an acyl derivative thereof, a uridine phosphate, uracil, or a salt thereof, thereby increasing a level of acetylcholine in a synapse of a subject.

In another embodiment, the present invention provides a method of increasing a level of a neurotransmitter in a synapse of a subject, comprising administering to the subject a composition comprising (a) a uridine, an acyl derivative thereof, a uridine phosphate, uracil, or a salt thereof, and (b) a choline or salt thereof, thereby increasing a level of a neurotransmitter in a synapse of a subject.

In another embodiment, the present invention provides a method of stimulating or enhancing a neurite outgrowth of a neural cell of a subject, comprising administering to the subject a composition comprising (a) a uridine, an acyl derivative thereof, a uridine phosphate, uracil, or a salt thereof; and (b) a choline or salt thereof, thereby stimulating or enhancing a neurite outgrowth of a neural cell of a subject.

In another embodiment, the present invention provides a method of stimulating or enhancing a neurite branching of a neural cell of a subject, comprising administering to the subject a composition comprising (a) a uridine, an acyl derivative thereof, a uridine phosphate, uracil, or a salt thereof; and (b) a choline or salt thereof, thereby stimulating or enhancing a neurite branching of a neural cell of a subject.

In another embodiment, the present invention provides a method of increasing a level of a neurofilament-70 (NF-70) or a neurofilament-M (NF-M) protein in a brain of a subject, comprising administering to the subject a uridine, an acyl derivative thereof, a uridine phosphate, uracil, or a salt thereof, thereby increasing a level of an NF-70 or an NF-M protein in a brain of a subject.

In another embodiment, the present invention provides a method of increasing a level of an NF-70 or an NF-M protein in a brain of a subject, comprising administering to the subject a composition comprising (a) a uridine, an acyl derivative thereof, a uridine phosphate, uracil, or a salt thereof, and (b) a choline or salt thereof, thereby increasing a level of an NF-70 or an NF-M protein in a brain of a subject, thereby increasing a level of an NF-70 or an NF-M protein in a brain of a subject.

In another embodiment, the present invention provides a method of facilitating or enhancing brain repair, comprising administering to the subject a uridine, an acyl derivative thereof, a uridine phosphate, uracil, or a salt thereof, thereby facilitating or enhancing brain repair.

In another embodiment, the present invention provides a method of facilitating or enhancing brain repair, comprising administering to the subject a composition comprising (a) a uridine, an acyl derivative thereof, a uridine phosphate, uracil, or a salt thereof, and (b) a choline or salt thereof, thereby facilitating or enhancing brain repair.

In another embodiment, the present invention provides a method of restoring a cognitive function in a subject having an impairment in said cognitive function, comprising administering to said subject a uridine, an acyl derivative thereof, a uridine phosphate, uracil, or a salt thereof, thereby restoring a cognitive function in a subject having an impairment in said cognitive function.

In another embodiment, the present invention provides a method of restoring a cognitive function in a subject having an impairment in said cognitive function, comprising administering to said subject a comprising (a) a uridine, an acyl derivative thereof, a uridine phosphate, uracil, or a salt thereof; and (b) a choline or salt thereof, thereby restoring a cognitive function in a subject having an impairment in said cognitive function.

In another embodiment, the present invention provides a method of treating or reducing an incidence of an age-related cognitive disorder or Age-Associated Memory Impairment (AAMI) in a subject, comprising administering to said subject a uridine, an acyl derivative thereof, a uridine phosphate, uracil, or a salt thereof, thereby treating or reducing an incidence of an age-related cognitive disorder or AAMI in a subject.

In another embodiment, the present invention provides a method of treating or reducing an incidence of an age-related cognitive disorder or AAMI in a subject, comprising administering to said subject a composition comprising (a) a uridine, an acyl derivative thereof, a uridine phosphate, uracil, or a salt thereof, and (b) a choline or salt thereof, thereby treating or reducing an incidence of an age-related cognitive disorder or AAMI in a subject.

In another embodiment, the present invention provides a method of improving or restoring a cholinergic function of a brain of a subject, comprising administering to said subject a uridine, an acyl derivative thereof, a uridine phosphate, uracil, or a salt thereof, thereby improving or restoring a cholinergic function of a brain of a subject.

In another embodiment, the present invention provides a method of improving or restoring a cholinergic function of a brain of a subject, comprising administering to said subject a composition comprising (a) a uridine, an acyl derivative thereof, a uridine phosphate, uracil, or a salt thereof; and (b) a choline or salt thereof, thereby improving or restoring a cholinergic function of a brain of a subject.

DETAILED DESCRIPTION OF THE INVENTION

Figure 1:
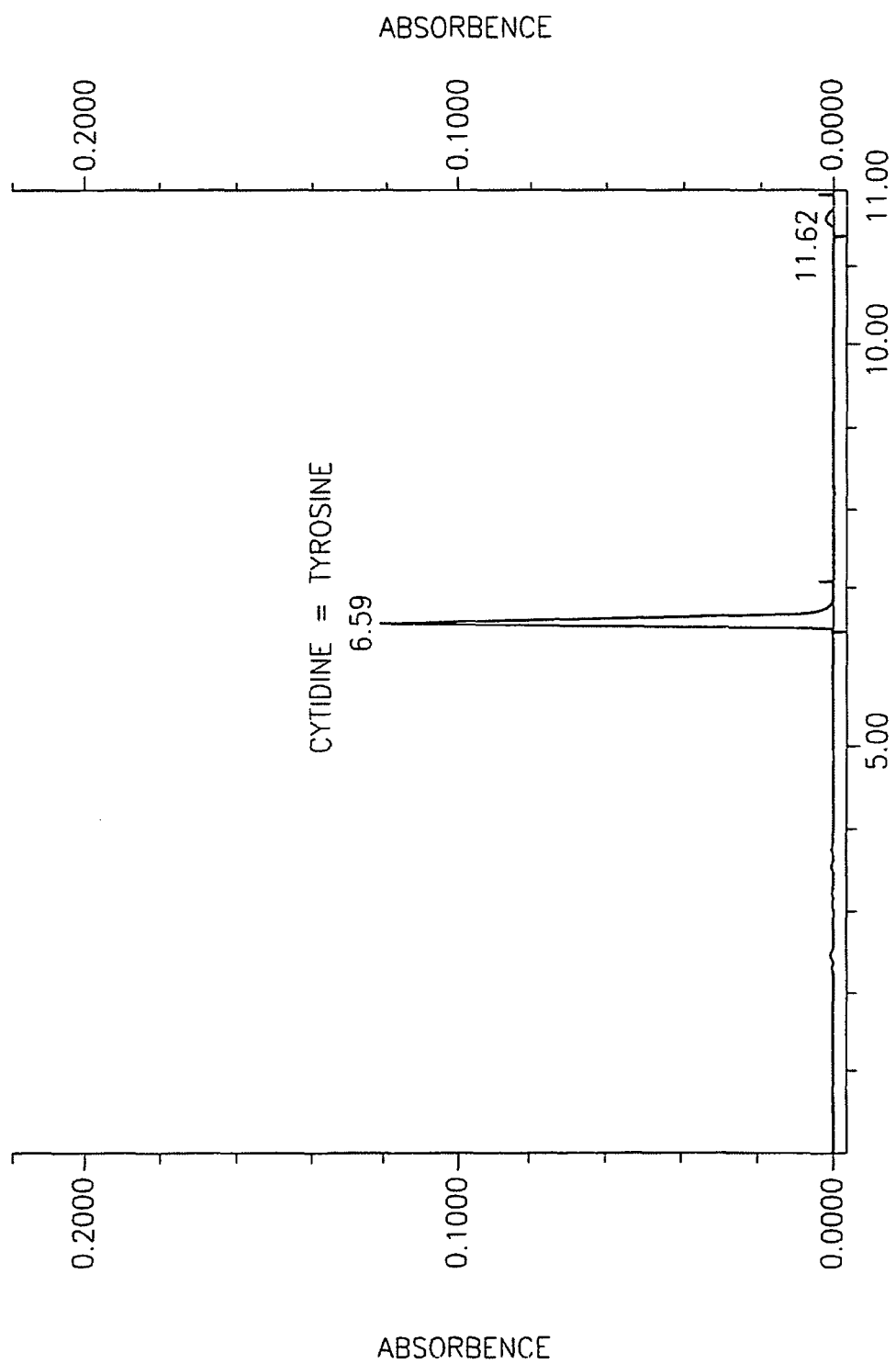
FIG. 1 illustrates the coincidence of cytidine and tyrosine peaks (6.59) when tested by a standard HPLC method.

The present invention is directed to methods of ameliorating hippocampal dysfunction and improving or inhibiting decline in intelligence or cognitive or hippocampal-dependent memory of a subject and of increasing synthesis and release of neurotransmitters, neurite outgrowth, and levels of neurofilament proteins in the brain and CNS of a subject, comprising administering to the subject a uridine, an acyl derivative thereof, a uridine phosphate, uracil, or a salt thereof.

In one embodiment, the present invention provides a method of ameliorating or inhibiting a decline in a cognitive memory or intelligence of a subject, comprising administering to the subject a uridine, thereby ameliorating or inhibiting a decline in a cognitive memory or intelligence of a subject. In another embodiment, the present invention provides a method of ameliorating or inhibiting a decline in a cognitive memory or intelligence of a subject, comprising administering to the subject an acylated uridine compound or acyl derivative of a uridine, thereby ameliorating or inhibiting a decline in a cognitive memory or intelligence of a subject. In another embodiment, the present invention provides a method of ameliorating or inhibiting a decline in a cognitive memory or intelligence of a subject, comprising administering to the subject a uridine phosphate, thereby ameliorating or inhibiting a decline in a cognitive memory or intelligence of a subject. Each possibility represents a separate embodiment of the present invention.

In another embodiment, the present invention provides a method of improving or enhancing a cognitive memory or intelligence of a subject, comprising administering to the subject a uridine, thereby improving or enhancing a cognitive memory or intelligence of a subject. In another embodiment, the present invention provides a method of improving or enhancing a cognitive memory or intelligence of a subject, comprising administering to the subject an acylated uridine compound or acyl derivative of a uridine, thereby improving or enhancing a cognitive memory or intelligence of a subject. In another embodiment, the present invention provides a method of improving or enhancing a cognitive memory or intelligence of a subject, comprising administering to the subject a uridine phosphate, thereby improving or enhancing a cognitive memory or intelligence of a subject. Each possibility represents a separate embodiment of the present invention.

In another embodiment, the present invention provides a method of ameliorating or inhibiting a decline in a cognitive memory or intelligence of a subject, comprising administering to the subject a composition comprising (a) a uridine; and (b) a choline or salt thereof, thereby ameliorating or inhibiting a decline in a cognitive memory or intelligence of a subject. In another embodiment, the present invention provides a method of ameliorating or inhibiting a decline in a cognitive memory or intelligence of a subject, comprising administering to the subject a composition comprising (a) an acylated uridine compound or acyl derivative of a uridine; and (b) a choline or salt thereof, thereby ameliorating or inhibiting a decline in a cognitive memory or intelligence of a subject. In another embodiment, the present invention provides a method of ameliorating or inhibiting a decline in a cognitive memory or intelligence of a subject, comprising administering to the subject a composition comprising (a) a uridine phosphate; and (b) a choline or salt thereof, thereby ameliorating or inhibiting a decline in a cognitive memory or intelligence of a subject. Each possibility represents a separate embodiment of the present invention.

In another embodiment, the present invention provides a method of improving or enhancing a cognitive memory or intelligence of a subject, comprising administering to the subject a composition comprising (a) a uridine; and (b) a choline or salt thereof, thereby improving or enhancing a cognitive memory or intelligence of a subject. In another embodiment, the present invention provides a method of improving or enhancing a cognitive memory or intelligence of a subject, comprising administering to the subject a composition comprising (a) an acylated uridine compound or acyl derivative of a uridine; and (b) a choline or salt thereof, thereby improving or enhancing a cognitive memory or intelligence of a subject. In another embodiment, the present invention provides a method of improving or enhancing a cognitive memory or intelligence of a subject, comprising administering to the subject a composition comprising (a) a uridine phosphate; and (b) a choline or salt thereof, thereby improving or enhancing a cognitive memory or intelligence of a subject. Each possibility represents a separate embodiment of the present invention.

As provided herein (Example 14), chronic dietary supplementation with UMP prevents the impairments caused by impoverished environmental conditions in spatial and/or cognitive memory and intelligence and improves spatial and/or cognitive memory and intelligence in healthy subjects. The data in Example 13 further show that the effects of uridine are enhanced by inclusion of a choline. Thus, administration of compositions comprising uridine and choline are effective at preventing impairments caused by impoverished environmental conditions in spatial and/or cognitive memory and intelligence and improving spatial and/or cognitive memory and intelligence in healthy subjects.

In another embodiment, the present invention provides a method of ameliorating or inhibiting a decline in a hippocampal-dependent memory of a subject, comprising administering to the subject a uridine, thereby ameliorating or inhibiting a decline in a hippocampal-dependent memory of a subject. In another embodiment, the present invention provides a method of ameliorating or inhibiting a decline in a hippocampal-dependent memory of a subject, comprising administering to the subject an acylated uridine compound or acyl derivative of a uridine, thereby ameliorating or inhibiting a decline in a hippocampal-dependent memory of a subject. In another embodiment, the present invention provides a method of ameliorating or inhibiting a decline in a hippocampal-dependent memory of a subject, comprising administering to the subject a uridine phosphate, thereby ameliorating or inhibiting a decline in a hippocampal-dependent memory of a subject. Each possibility represents a separate embodiment of the present invention.

In another embodiment, the present invention provides a method of ameliorating or inhibiting a decline in a hippocampal-dependent memory of a subject, comprising administering to the subject a composition comprising (a) a uridine; and (b) a choline or salt thereof, thereby ameliorating or inhibiting a decline in a hippocampal-dependent memory of a subject. In another embodiment, the present invention provides a method of ameliorating or inhibiting a decline in a hippocampal-dependent memory of a subject, comprising administering to the subject a composition comprising (a) an acylated uridine compound or acyl derivative of a uridine; and (b) a choline or salt thereof, thereby ameliorating or inhibiting a decline in a hippocampal-dependent memory of a subject. In another embodiment, the present invention provides a method of ameliorating or inhibiting a decline in a hippocampal-dependent memory of a subject, comprising administering to the subject a composition comprising (a) a uridine phosphate; and (b) a choline or salt thereof, thereby ameliorating or inhibiting a decline in a hippocampal-dependent memory of a subject. Each possibility represents a separate embodiment of the present invention.

In another embodiment, the present invention provides a method of improving or enhancing a hippocampal-dependent memory of a subject, comprising administering to the subject a uridine, thereby improving or enhancing a hippocampal-dependent memory of a subject. In another embodiment, the present invention provides a method of improving or enhancing a hippocampal-dependent memory of a subject, comprising administering to the subject an acylated uridine compound or acyl derivative of a uridine, thereby improving or enhancing a hippocampal-dependent memory of a subject. In another embodiment, the present invention provides a method of improving or enhancing a hippocampal-dependent memory of a subject, comprising administering to the subject a uridine phosphate, thereby improving or enhancing a hippocampal-dependent memory of a subject. Each possibility represents a separate embodiment of the present invention.

In another embodiment, the present invention provides a method of improving or enhancing a hippocampal-dependent memory of a subject, comprising administering to the subject a composition comprising (a) a uridine; and (b) a choline or salt thereof, thereby improving or enhancing a hippocampal-dependent memory of a subject. In another embodiment, the present invention provides a method of improving or enhancing a hippocampal-dependent memory of a subject, comprising administering to the subject a composition comprising (a) an acylated uridine compound or acyl derivative of a uridine; and (b) a choline or salt thereof, thereby improving or enhancing a hippocampal-dependent memory of a subject. In another embodiment, the present invention provides a method of improving or enhancing a hippocampal-dependent memory of a subject, comprising administering to the subject a composition comprising (a) a uridine phosphate; and (b) a choline or salt thereof, thereby improving or enhancing a hippocampal-dependent memory of a subject. Each possibility represents a separate embodiment of the present invention.

As provided herein (Example 14), chronic dietary supplementation with UMP prevents the hippocampal-dependent memory impairments caused by impoverished environmental conditions and improves hippocampal-dependent memory in healthy subjects. The data in Example 13 further show that the effects of uridine are enhanced by inclusion of a choline. Thus, administration of compositions comprising uridine and choline are effective at preventing the hippocampal-dependent memory impairments caused by impoverished environmental conditions and improving hippocampal-dependent memory in healthy subjects.

The decline in cognitive memory, hippocampal-dependent memory, or intelligence that is treated, ameliorated, or inhibited by a method of the present invention is, in one embodiment, due to age. "Due to age" refers, in another embodiment, to a decline observed in a subject over the age of 55. In another embodiment, the subject is over the age of 57. In another embodiment, the subject is over the age of 59. In another embodiment, the subject is over the age of 60. In another embodiment, the subject is over the age of 62. In another embodiment, the subject is over the age of 64. In another embodiment, the subject is over the age of 65. In another embodiment, the subject is over the age of 67. In another embodiment, the subject is over the age of 69. In another embodiment, the subject is over the age of 70. In another embodiment, the subject is over the age of 72. In another embodiment, the subject is over the age of 74. In another embodiment, the subject is over the age of 75. In another embodiment, the subject is over the age of 76. In another embodiment, the subject is over the age of 78. In another embodiment, the subject is over the age of 80. In another embodiment, the subject is over the age of 82. In another embodiment, the subject is over the age of 84. Each possibility represents another embodiment of the present invention.

In another embodiment, the decline that is treated is due to an age-related disease or age-related cognitive decline. In another embodiment, the age-related disease is Alzheimer's disease. In another embodiment, the age-related disease is Parkinson's disease. In another embodiment, the age-related disease is mild cognitive impairment. In another embodiment, the age-related disease is any other age-related disease or age-related cognitive decline that is known in the art. Each possibility represents a separate embodiment of the present invention.

The subject of methods of the present invention is, in one embodiment, a human. In another embodiment, the subject is a female. In another embodiment, the subject is a male. In another embodiment, the subject is a pregnant female. In another embodiment, the subject is a nursing female. In another embodiment, the subject is a baby. In another embodiment, the subject is a child. In another embodiment, the subject is a young child in another embodiment, the subject is an adult. In another embodiment, the subject is an aging adult. In another embodiment, "aging" refers to any of the embodiments enumerated above. Each possibility represents a separate embodiment of the present invention.

"Baby" refers, in another embodiment, to a subject under the age of 1 year. In another embodiment, the term refers to a subject under the age of 18 months. In another embodiment, the term refers to a subject under the age of 6 months. In another embodiment, the term refers to a subject under the age of 7 months. In another embodiment, the term refers to a subject under the age of 8 months. In another embodiment, the term refers to a subject under the age of 9 months In another embodiment, the term refers to a subject under the age of 10 months. In another embodiment, the term refers to a subject under the age of 10 months. In another embodiment, the term refers to a subject under the age of 13 months. In another embodiment, the term refers to a subject under the age of 14 months. In another embodiment, the term refers to a subject under the age of 16 months. In another embodiment, the term refers to a subject under the age of 20 months. In another embodiment, the term refers to a subject under the age of 2 years. In another embodiment, the term refers to a subject that has not yet been weaned. In another embodiment, the term refers to a subject that has been weaned, but is within one of the above age ranges Each possibility represents a separate embodiment of the present invention.

"Child" refers, in another embodiment, to a subject under the age of 18 years. In another embodiment, the term refers to a subject under the age of 17 years. In another embodiment, the term refers to a subject under the age of 16 years. In another embodiment, the term refers to a subject under the age of 15 years. In another embodiment, the term refers to a subject under the age of 14 years. In another embodiment, the term refers to a subject under the age of 13 years. In another embodiment, the term refers to a subject under the age of 12 years. In another embodiment, the term refers to a subject under the age of 17 years In another embodiment, the term refers to a subject under the age of 10 years. In another embodiment, the term refers to a subject under the age of 9 years. In another embodiment, the term refers to a subject under the age of 8 years. In another embodiment, the term refers to a subject under the age of 7 years.

"Young child" refers, in another embodiment, to a subject under the age of 7 years In another embodiment, the term refers to a subject under the age of 6 years. In another embodiment, the term refers to a subject under the age of 5 years In another embodiment, the the refers to a subject under the age of 4 years. In another embodiment, the term refers to a subject under the age of 3½ years In another embodiment, the term refers to a subject under the age of 3 years In another embodiment, the term refers to a subject under the age of 2½ years. Each possibility represents a separate embodiment of the present invention.

"Adult" refers, in other embodiments, to a subject over one of the ages listed above as an upper limit for a child. In another embodiment, the term refers to a subject over one of the ages listed above as an upper limit for a young child. Each possibility represents a separate embodiment of the present invention.

In another embodiment, the decline that is treated is due to inactivity. In another embodiment, the inactivity is physical inactivity. In another embodiment, the inactivity is mental inactivity In another embodiment, the inactivity is social inactivity. In another embodiment, the inactivity is any other type of inactivity. Each possibility represents another embodiment of the present invention.

Methods for determining the cause of decline in cognitive memory, hippocampal-dependent memory, and intelligence are well known in the art, and are described, for example, in Robertson R G et al (Geriatric failure to thrive. Am Fam Physician. 2004 Jul. 15; 70(2):343-50) and van de Port et al (Susceptibility to deterioration of mobility long-term after stroke: a prospective cohort study. Stroke. 2006 January; 37(1):167-71). Each method represents a separate embodiment of the present invention.

In another embodiment, "improving" or "improvement" of a cognitive or hippocampal-dependent memory refer to increasing the memory capacity of the subject. In another embodiment, the terms refer to an increased or improved baseline level of the memory in the subject. In another embodiment, the terms refer to an increased or improved level of the memory.

In another embodiment, "improving" a cognitive memory, hippocampal-dependent memory, and intelligence refers to effecting a 10% improvement thereof. In another embodiment, the term refers to effecting a 20% improvement thereof. In another embodiment, the term refers to effecting a 30% improvement thereof In another embodiment, the term refers to effecting a 40% improvement thereof In another embodiment, the term refers to effecting a 50% improvement thereof. In another embodiment, the term refers to effecting a 60% improvement thereof In another embodiment, the term refers to effecting a 70% improvement thereof. In another embodiment, the term refers to effecting an 80% improvement thereof. In another embodiment, the term refers to effecting a 90% improvement thereof. In another embodiment, the term refers to effecting a 100% improvement thereof. Each possibility represents a separate embodiment of the present invention.

In another embodiment, improvement of a cognitive memory or intelligence is assessed relative to the cognitive memory or intelligence before beginning treatment. In another embodiment, improvement of a cognitive memory or intelligence is assessed relative to an untreated subject. In another embodiment, improvement of a cognitive memory or intelligence is assessed according to a standardized criterion such as, for example, a test or the like. Each type of improvement of cognitive activity represents a separate embodiment of the present invention.

In another embodiment, the present invention provides a method of ameliorating a hippocampal dysfunction in a subject, comprising administering to the subject a uridine, thereby ameliorating a hippocampal dysfunction in a subject. In another embodiment, the present invention provides a method of ameliorating a hippocampal dysfunction in a subject, comprising administering to the subject an acylated uridine compound or acyl derivative of a uridine, thereby ameliorating a hippocampal dysfunction in a subject. In another embodiment, the present invention provides a method of ameliorating a hippocampal dysfunction in a subject, comprising administering to the subject a uridine phosphate, thereby ameliorating a hippocampal dysfunction in a subject. Each possibility represents a separate embodiment of the present invention.

In another embodiment, the present invention provides a method of ameliorating a hippocampal dysfunction in a subject, comprising administering to the subject a composition comprising (a) a uridine; and (b) a choline or salt thereof, thereby ameliorating a hippocampal dysfunction in a subject. In another embodiment, the present invention provides a method of ameliorating a hippocampal dysfunction in a subject, comprising administering to the subject a composition comprising (a) an acylated uridine compound or acyl derivative of a uridine; and (b) a choline or salt thereof thereby ameliorating a hippocampal dysfunction in a subject. In another embodiment, the present invention provides a method of ameliorating a hippocampal dysfunction in a subject, comprising administering to the subject a composition comprising (a) a uridine phosphate; and (b) a choline or salt thereof, thereby ameliorating a hippocampal dysfunction in a subject. Each possibility represents a separate embodiment of the present invention.

In another embodiment, the hippocampal dysfunction or decline in memory that is treated results from a neurological disorder. In one embodiment, the neurological disorder is a memory disorder. The memory disorder comprises, in one embodiment, a memory decline In another embodiment, the memory decline is associated with brain aging. In another embodiment, the memory disorder is selected from the group consisting of Pick's disease, Lewy Body disease, and a dementia. In one embodiment, the dementia is associated with Huntington's disease In another embodiment, the dementia is associated with AIDS dementia. Each possibility represents a separate embodiment of the present invention.

In one embodiment, the neurological disorder is associated with a dopaminergic pathway. In another embodiment, the neurological disorder is not associated with a dopaminergic pathway. Each possibility represents a separate embodiment of the present invention.

In another embodiment, the neurological disorder is a cognitive dysfunction. In one embodiment, the cognitive dysfunction is dyslexia, In one embodiment, the cognitive dysfunction comprises a lack of attention. In one embodiment, the cognitive dysfunction comprises a lack of alertness In one embodiment, the cognitive dysfunction comprises a lack of concentration. In one embodiment, the cognitive dysfunction comprises a lack of focus. In other embodiments, the cognitive dysfunction is associated with a stroke or a multi-infarct dementia. In one embodiment, the cognitive dysfunction comprises minimal cognitive impairment. In one embodiment, the cognitive dysfunction comprises age-related memory impairment. Each possibility represents a separate embodiment of the present invention.

In another embodiment, the neurological disorder is an emotional disorder. In one embodiment, the emotional disorder comprises mania In another embodiment, the emotional disorder comprises depression. In another embodiment, the emotional disorder comprises stress. In another embodiment, the emotional disorder comprises panic. In another embodiment, the emotional disorder comprises anxiety. In another embodiment, the emotional disorder comprises dysthymia. In another embodiment, the emotional disorder comprises psychosis. In another embodiment, the emotional disorder comprises a seasonal effective disorder. In another embodiment, the emotional disorder comprises a bipolar disorder.

In another embodiment, the neurological disorder is a depression. In one embodiment, the depression is an endogenous depression. In another embodiment, the depression is a major depressive disorder. In another embodiment, the depression is depression with anxiety. In another embodiment, the depression is bipolar depression. Each type of depression represents a separate embodiment of the present invention.

In another embodiment, the neurological disorder is selected from the group consisting of ataxia and Friedreich's ataxia. In another embodiment, the neurological disorder of the present invention excludes epilepsy, seizures, convulsions, and the like.

In another embodiment, the neurological disorder is a movement disorder. The movement disorder comprises, in one embodiment, a tardive dyskinesia. In another embodiment, the movement disorder comprises a dystonia. In another embodiment, the movement disorder comprises a Tourette's syndrome. In another embodiment, the movement disorder is any other movement disorder known in the art.

In another embodiment, the neurological disorder is a cerebro-vascular disease. The cerebro-vascular disease results, in one embodiment, from hypoxia. In another embodiment, the cerebro-vascular disease results from any other cause capable of causing a cerebro-vascular disease. In another embodiment, the cerebro-vascular disease is cerebral thrombosis. In another embodiment, the cerebro-vascular disease is ischemia.

In another embodiment, the neurological disorder is a behavioral syndrome In another embodiment, the neurological disorder is a neurological syndrome. In one embodiment, the behavioral syndrome or neurological syndrome follows brain trauma. In another embodiment, the behavioral syndrome or neurological syndrome follows spinal cord injury. In another embodiment, the behavioral syndrome or neurological syndrome follows anoxia.

In another embodiment, the neurological disorder is a peripheral nervous system disorder In one embodiment, the peripheral nervous system disorder is a neuromuscular disorder. In another embodiment, the peripheral nervous system disorder is any other peripheral nervous system disorder known in the art. In another embodiment, the neuromuscular disorder is myasthenia gravis. In another embodiment, the neuromuscular disorder is post-polio syndrome. In another embodiment, the neuromuscular disorder is a muscular dystrophy.

Each type of neurological disorder mentioned herein represents a separate embodiment of the present invention.

In another embodiment, the present invention provides a method of increasing or enhancing an ability of a brain cell or neural cell of a subject to release an effective quantity of dopamine into a synapse, comprising administering to the subject a uridine, thereby increasing or enhancing an ability of a brain cell or neural cell of a subject to release an effective quantity of dopamine into a synapse. In another embodiment, the present invention provides a method of increasing or enhancing an ability of a brain cell or neural cell of a subject to release an effective quantity of dopamine into a synapse, comprising administering to the subject an acylated uridine compound or acyl derivative of a uridine, thereby increasing or enhancing an ability of a brain cell or neural cell of a subject to release an effective quantity of dopamine into a synapse. In another embodiment, the present invention provides a method of increasing or enhancing an ability of a brain cell or neural cell of a subject to release an effective quantity of dopamine into a synapse, comprising administering to the subject a uridine phosphate, thereby increasing or enhancing an ability of a brain cell or neural cell of a subject to release an effective quantity of dopamine into a synapse. Each possibility represents a separate embodiment of the present invention.

In another embodiment, the present invention provides a method of increasing or enhancing an ability of a brain cell or neural cell of a subject to repeatedly release an effective quantity of dopamine into a synapse, comprising administering to the subject a uridine, thereby increasing or enhancing an ability of a brain cell or neural cell of a subject to repeatedly release an effective quantity of dopamine into a synapse. In another embodiment, the present invention provides a method of increasing or enhancing an ability of a brain cell or neural cell of a subject to repeatedly release an effective quantity of dopamine into a synapse, comprising administering to the subject an acylated uridine compound or acyl derivative of a uridine, thereby increasing or enhancing an ability of a brain cell or neural cell of a subject to repeatedly release an effective quantity of dopamine into a synapse. In another embodiment, the present invention provides a method of increasing or enhancing an ability of a brain cell or neural cell of a subject to repeatedly release an effective quantity of dopamine into a synapse, comprising administering to the subject a uridine phosphate, thereby increasing or enhancing an ability of a brain cell or neural cell of a subject to repeatedly release an effective quantity of dopamine into a synapse. Each possibility represents a separate embodiment of the present invention.

In another embodiment, the present invention provides a method of increasing or enhancing an ability of a brain cell or neural cell of a subject to release an effective quantity of dopamine into a synapse, comprising administering to the subject a composition comprising (a) a uridine, an acyl derivative thereof, a uridine phosphate, uracil, or a salt thereof; and (b) a choline or salt thereof, thereby increasing of enhancing an ability of a brain cell or neural cell of a subject to release an effective quantity of dopamine into a synapse.

In another embodiment, the present invention provides a method of increasing or enhancing an ability of a brain cell or neural cell of a subject to repeatedly release an effective quantity of dopamine into a synapse, comprising administering to the subject a composition comprising (a) a uridine; and (b) a choline or salt thereof, thereby increasing or enhancing an ability of a brain cell or neural cell of a subject to repeatedly release an effective quantity of dopamine into a synapse. In another embodiment, the present invention provides a method of increasing or enhancing an ability of a brain cell or neural cell of a subject to repeatedly release an effective quantity of dopamine into a synapse, comprising administering to the subject a composition comprising (a) an acylated uridine compound or acyl derivative of a uridine; and (b) a choline or salt thereof, thereby increasing or enhancing an ability of a brain cell or neural cell of a subject to repeatedly release an effective quantity of dopamine into a synapse. In another embodiment, the present invention provides a method of increasing or enhancing an ability of a brain cell or neural cell of a subject to repeatedly release an effective quantity of dopamine into a synapse, comprising administering to the subject a composition comprising (a) a uridine phosphate; and (b) a choline or salt thereof, thereby increasing or enhancing an ability of a brain cell or neural cell of a subject to repeatedly release an effective quantity of dopamine into a synapse. Each possibility represents a separate embodiment of the present invention.

In another embodiment, the present invention provides a method of increasing a level of acetylcholine in a synapse of a subject, comprising administering to the subject a uridine, thereby increasing a level of acetylcholine in a synapse of a subject. In another embodiment, the present invention provides a method of increasing a level of acetylcholine in a synapse of a subject, comprising administering to the subject an acylated uridine compound or acyl derivative of a uridine, thereby increasing a level of acetylcholine in a synapse of a subject. In another embodiment the present invention provides a method of increasing a level of acetylcholine in a synapse of a subject, comprising administering to the subject a uridine phosphate, thereby increasing a level of acetylcholine in a synapse of a subject. Each possibility represents a separate embodiment of the present invention.

In another embodiment, the present invention provides a method of increasing a level of a neurotransmitter in a synapse of a subject, comprising administering to the subject a composition comprising (a) a uridine; and (b) a choline or salt thereof, thereby increasing a level of a neurotransmitter in a synapse of a subject. In another embodiment, the present invention provides a method of increasing a level of a neurotransmitter in a synapse of a subject, comprising administering to the subject a composition comprising (a) an acylated uridine compound or acyl derivative of a uridine; and (b) a choline or salt thereof, thereby increasing a level of a neurotransmitter in a synapse of a subject. In another embodiment, the present invention provides a method of increasing a level of a neurotransmitter in a synapse of a subject, comprising administering to the subject a composition comprising (a) a uridine phosphate; and (b) a choline or salt thereof, thereby increasing a level of a neurotransmitter in a synapse of a subject. Each possibility represents a separate embodiment oft the present invention.

In another embodiment, the present invention provides a method of stimulating or enhancing a neurite outgrowth of a neural cell of a subject, comprising administering to the subject a composition comprising (a) a uridine; and (b) a choline or salt thereof, thereby stimulating or enhancing a neurite outgrowth of a neural cell of a subject. In another embodiment, the present invention provides a method of stimulating or enhancing a neurite outgrowth of a neural cell of a subject, comprising administering to the subject a composition comprising (a) an acylated uridine compound or acyl derivative of a uridine; and (b) a choline or salt thereof, thereby stimulating or enhancing a neurite outgrowth of a neural cell of a subject. In another embodiment, the present invention provides a method of stimulating or enhancing a neurite outgrowth of a neural cell of a subject, comprising administering to the subject a composition comprising (a) a uridine phosphate; and (b) a choline or salt thereof, thereby stimulating or enhancing a neurite outgrowth of a neural cell of a subject. Each possibility represents a separate embodiment of the present invention.

In another embodiment, the present invention provides a method of stimulating or enhancing a neurite branching of a neural cell of a subject, comprising administering to the subject a composition comprising (a) a uridine; (b) a choline or salt thereof, thereby stimulating or enhancing a neurite branching of a neural cell of a subject. In another embodiment, the present invention provides a method of stimulating or enhancing a neurite branching of a neural cell of a subject, comprising administering to the subject a composition comprising (a) an acylated uridine compound or acyl derivative of a uridine; and (b) a choline or salt thereof, thereby stimulating or enhancing a neurite branching of a neural cell of a subject. In another embodiment, the present invention provides a method of stimulating or enhancing a neurite branching of a neural cell of a subject, comprising administering to the subject a composition comprising (a) a uridine phosphate; and (b) a choline or salt thereof, thereby stimulating or enhancing a neurite branching of a neural cell of a subject. Each possibility represents a separate embodiment of the present invention.

In another embodiment, the present invention provides a method of increasing a level of a neurofilament-70 (NF-70) or a neurofilament-M (NF-M) protein in a brain of a subject, comprising administering to the subject a uridine, thereby increasing a level of an NF-70 or an NF-M protein in a brain of a subject. In another embodiment, the present invention provides a method of increasing a level of a neurofilament-70 (NF-70) or a neurofilament-M (NF-M) protein in a brain of a subject, comprising administering to the subject an acylated uridine compound or acyl derivative of a uridine, thereby increasing a level of an NF-70 or an NF-M protein in a brain of a subject. In another embodiment, the present invention provides a method of increasing a level of a neurofilament-70 (NF-70) or a neurofilament-M (NF-M) protein in a brain of a subject, comprising administering to the subject a uridine phosphate, thereby increasing a level of an NF-70 or an NF-M protein in a brain of a subject. Each possibility represents a separate embodiment of the present invention.

In another embodiment, the present invention provides a method of increasing a level of an NF-70 or an NF-M protein in a brain of a subject, comprising administering to the subject a composition comprising (a) a uridine; and (b) a choline or salt thereof, thereby increasing a level of an NF-70 or an NF-M protein in a brain of a subject. In another embodiment, the present invention provides a method of increasing a level of an NF-70 or an NF-M protein in a brain of a subject, comprising administering to the subject a composition comprising (a) an acylated uridine compound or acyl derivative of a uridine; and (b) a choline or salt thereof, thereby increasing a level of an NF-70 or an NF-M protein in a brain of a subject. In another embodiment, the present invention provides a method of increasing a level of an NF-70 or an NF-M protein in a brain of a subject, comprising administering to the subject a composition comprising (a) a uridine phosphate; and (b) a choline or salt thereof, thereby increasing a level of an NF-70 or an NF-M protein in a brain of a subject. Each possibility represents a separate embodiment of the present invention.

In another embodiment, the present invention provides a method of facilitating or enhancing brain repair, comprising administering to the subject a uridine, thereby facilitating or enhancing brain repair. In another embodiment, the present invention provides a method of facilitating or enhancing brain repair, comprising administering to the subject an acylated uridine compound or acyl derivative of a uridine, thereby facilitating or enhancing brain repair. In another embodiment, the present invention provides a method of facilitating or enhancing brain repair, comprising administering to the subject a uridine phosphate, thereby facilitating or enhancing brain repair. Each possibility represents a separate embodiment of the present invention.

In another embodiment, the present invention provides a method of facilitating or enhancing brain repair, comprising administering to the subject a composition comprising (a) a uridine; and (b) a choline or salt thereof, thereby facilitating or enhancing brain repair. In another embodiment, the present invention provides a method of facilitating or enhancing brain repair, comprising administering to the subject a composition comprising (a) an acylated uridine compound or acyl derivative of a uridine; and (b) a choline or salt thereof, thereby facilitating or enhancing brain repair. In another embodiment, the present invention provides a method of facilitating or enhancing brain repair, comprising administering to the subject a composition comprising (a) a uridine phosphate; and (b) a choline or salt thereof, thereby facilitating or enhancing brain repair. Each possibility represents a separate embodiment of the present invention.

In another embodiment, the present invention provides a method of inhibiting a decline in a memory capability of a subject, comprising administering to the subject a uridine, an acyl derivative thereof, a uridine phosphate, uracil, or a salt thereof, thereby inhibiting a decline in a memory capability of a subject.

In another embodiment, the present invention provides a method of inhibiting a decline in a memory capability of a subject, comprising administering to the subject a composition comprising (a) a uridine, an acyl derivative thereof, a uridine phosphate, uracil, or a salt thereof, and (b) a choline or salt thereof, thereby inhibiting a decline in a memory capability of a subject.

In another embodiment, the brain repair is facilitated or enhanced following a stroke. In another embodiment, the brain repair is facilitated or enhanced following a brain injury. In another embodiment, the brain repair is facilitated or enhanced following any other event, disease or disorder known in the art that necessitates brain repair. Each possibility represents another embodiment of the present invention.

In another embodiment, the administration that is performed in a method of the present invention is chronically administering. "Chronically administering" refers, in one embodiment, to regular administration indefinitely. In another embodiment, the term refers to regular administration for at least one month. In another embodiment, the term refers to regular administration for at least 6 weeks. In another embodiment, the term refers to regular administration for at least two months. In another embodiment, the term refers to regular administration for at least 3 months. In another embodiment, the term refers to regular administration for at least 4 months. In another embodiment, the term refers to regular administration for at least 5 months. In another embodiment, the term refers to regular administration for at least 6 months. In another embodiment, the term refers to regular administration for at least 9 months. In another embodiment, the term refers to regular administration for at least 1 year. In another embodiment, the term refers to regular administration for at least 1.5 years. In another embodiment, the term refers to regular administration for at least 2 years. In another embodiment, the term refers to regular, administration for more than 2 years. In another embodiment, the term refers to regular administration until a follow-up visit. In another embodiment, the term refers to regular administration until re-assessment of the disease or disorder being treated. In another embodiment, the term refers to administration of a composition of the present invention by a feeding tube. In another embodiment, the administration is enteral. In another embodiment, the feeding tube is used for a comatose patient or subject. In another embodiment, the composition is used to restore cognitive function to the patient or subject Each possibility represents a separate embodiment of the present invention.

In another embodiment, "regular intervals" refers to daily administration. In another embodiment, the term refers to weekly administration. In another embodiment, the term refers to daily administration. In another embodiment, the term refers to administration 1-2 times per week. In another embodiment, the term refers to administration 1-3 times per week. In another embodiment, the term refers to administration 2-3 times per week. In another embodiment, the term refers to administration 14 times per week. In another embodiment, the term refers to administration 1-4 times per week. In another embodiment, the term refers to administration 1-5 times per week. In another embodiment, the term refers to administration 2-5 times per week. In another embodiment, the term refers to administration 3-5 times per week. In another embodiment, the term refers to administration 1-2 times per day. In another embodiment, the term refers to administration 1-3 times per day. In another embodiment, the term refers to administration 1-4 times per day. In another embodiment the term refers to administration 2-3 times per day. In another embodiment, the term refers to administration 2-4 times per day. In another embodiment, the term refers to administration 3-4 times per day. In another embodiment, the term refers to administration 2-5 times per day. In another embodiment, the term refers to administration 3-5 times per day. In another embodiment, the term refers to administration 4-5 times per day.

In another embodiment of methods and compositions of the present invention, 20 mg of uridine or a derivative thereof is administered per day. In another embodiment, the dosage is 10 mg/day. In another embodiment, the dosage is 30 mg/day. In another embodiment, the dosage is 40 mg/day. In another embodiment, the dosage is 60 mg/day. In another embodiment, the dosage is mg/day. In another embodiment, the dosage is 100 mg/day. In another embodiment, the dosage is 150 mg/day. In another embodiment, the dosage is 200 mg/day. In another embodiment, the dosage is 300 mg/day. In another embodiment, the dosage is 400 mg/day. In another embodiment, the dosage is 600 mg/day. In another embodiment, the dosage is 800 mg/day. In another embodiment, the dosage is 1 g/day. In another embodiment, the dosage is 1.5 g/day. In another embodiment, the dosage is 2 g/day. In another embodiment, the dosage is 3 g/day. In another embodiment, the dosage is 5 g/day. In another embodiment, the dosage is more than 5 g/day.

In another embodiment, the dosage is 10-20 mg/day. In another embodiment, the dosage is 20-30 mg/day. In another embodiment, the dosage is 20-40 ma/day. In another embodiment, the dosage is 30-60 mg/day. In another embodiment, the dosage is 40-80 mg/day. In another embodiment, the dosage is 50-100 mg/day. In another embodiment, the dosage is 50-150 mg/day. In another embodiment, the dosage is 100-200 mg/day. In another embodiment, the dosage is 200-300 mg/day. In another embodiment, the dosage is 300-400 mg/day. In another embodiment, the dosage is 400-600 mg/day. In another embodiment, the dosage is 500-800 mg/day. In another embodiment, the dosage is 400 mg-1 g/day. In another embodiment, the dosage is 800 mg-1 g/day. In another embodiment, the dosage is 1-1.5 g/day. In another embodiment, the dosage is 1.5-2 g/day. In another embodiment, the dosage is 1-2 g/day. In another embodiment, the dosage is 1-3 g/day. In another embodiment, the dosage is 1.5-3 g/day. In another embodiment, the dosage is 2-3 g/day. In another embodiment, the dosage is 1-4 g/day. In another embodiment, the dosage is 24 g/day. In another embodiment, the dosage is 1-5 g/day. In another embodiment, the dosage is 2-5 g/day. In another embodiment, the dosage is 3-5 g/day. Each possibility represents another embodiment of the present invention.

In another embodiment, one of the above amounts is administered twice per day. In another embodiment, one of the above amounts is administered three times per day. In another embodiment, one of the above amounts is administered once per week. In another embodiment, one of the above amounts is administered twice per week. In another embodiment, one of the above amounts is administered three times per week. In another embodiment, one of the above amounts is administered according to any other dosing regimen known in the art. Each possibility represents another embodiment of the present invention.

In another embodiment of methods and compositions of the present invention, 20 mg of uridine or a derivative thereof is administered per dose. In another embodiment, the dosage is 10 mg/dose. In another embodiment, the dosage is 30 mg/dose. In another embodiment, the dosage is 40 mg/dose. In another embodiment, the dosage is 60 mg/dose. In another embodiment, the dosage is mg/dose. In another embodiment, the dosage is 100 mg/dose. In another embodiment, the dosage is 150 mg/dose. In another embodiment, the dosage is 200 mg/dose. In another embodiment, the dosage is 300 mg/dose. In another embodiment, the dosage is 400 mg/dose. In another embodiment, the dosage is 600 mg/dose. In another embodiment, the dosage is 800 mg/dose. In another embodiment, the dosage is 1 g/dose. In another embodiment, the dosage is 1.5 g/dose. In another embodiment, the dosage is 2 g/dose. In another embodiment, the dosage is 3 g/dose. In another embodiment, the dosage is 5 g/dose. In another embodiment, the dosage is more than 5 g/dose.

In another embodiment, the dosage is 10-20 mg/dose. In another embodiment, the dosage is 20-30 mg/dose. In another embodiment, the dosage is 20-40 mg/dose. In another embodiment, the dosage is 30-60 mg/dose In another embodiment, the dosage is 40-80 mg/dose. In another embodiment, the dosage is 50-100 mg/dose. In another embodiment, the dosage is 50-150 mg/dose. In another embodiment, the dosage is 100-200 mg/dose. In another embodiment, the dosage is 200-300 mg/dose. In another embodiment, the dosage is 300-400 mg/dose. In another embodiment, the dosage is 400-600 mg/dose. In another embodiment, the dosage is 500-800 mg/dose. In another embodiment, the dosage is 400 mg-1 g/dose. In another embodiment, the dosage is 800 mg-1 g/dose. In another embodiment, the dosage is 1-1.5 g/dose. In another embodiment, the dosage is 1.5-2 g/dose. In another embodiment, the dosage is 1-2 g/dose. In another embodiment, the dosage is 1-3 g/dose. In another embodiment, the dosage is; 1.5-3 g/dose. In another embodiment, the dosage is 2-3 g/dose. In another embodiment, the dosage is 1-4 g/dose. In another embodiment, the dosage is 2-4 g/dose. In another embodiment, the dosage is 1-5 g/dose. In another embodiment, the dosage is 2-5 g/dose. In another embodiment, the dosage is 3-5 g/dose. Each possibility represents another embodiment of the present invention.

Each of the above embodiments of "chronic administration" represents a separate embodiment of the present invention.

Figure 17A:
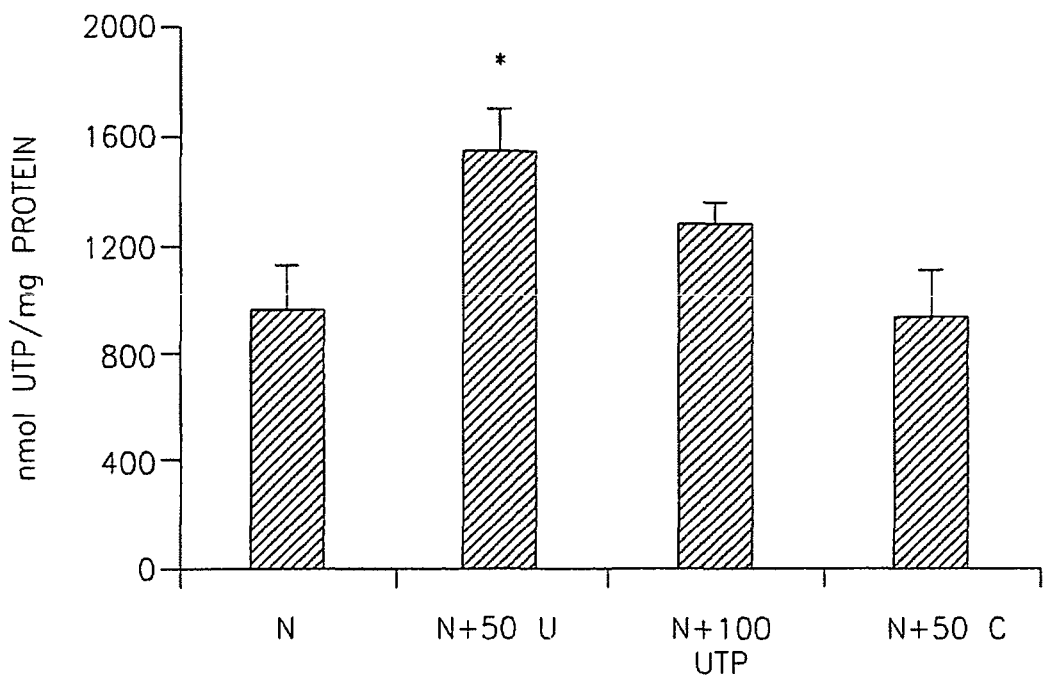
FIG. 17. P2Y receptor antagonists inhibited the effect of uridine on neurite outgrowth. Cells were treated for 4 days with NGF and with or without uridine (100 μM) and the P2Y receptor antagonists PPADS, suramin, or RB-2. Values represent means+SEM. ***$p<0.001$ vs. NGF treatment; #$p<0.05$, ###$p<0.001$ vs. NGF plus uridine treatment.
Figure 17B:
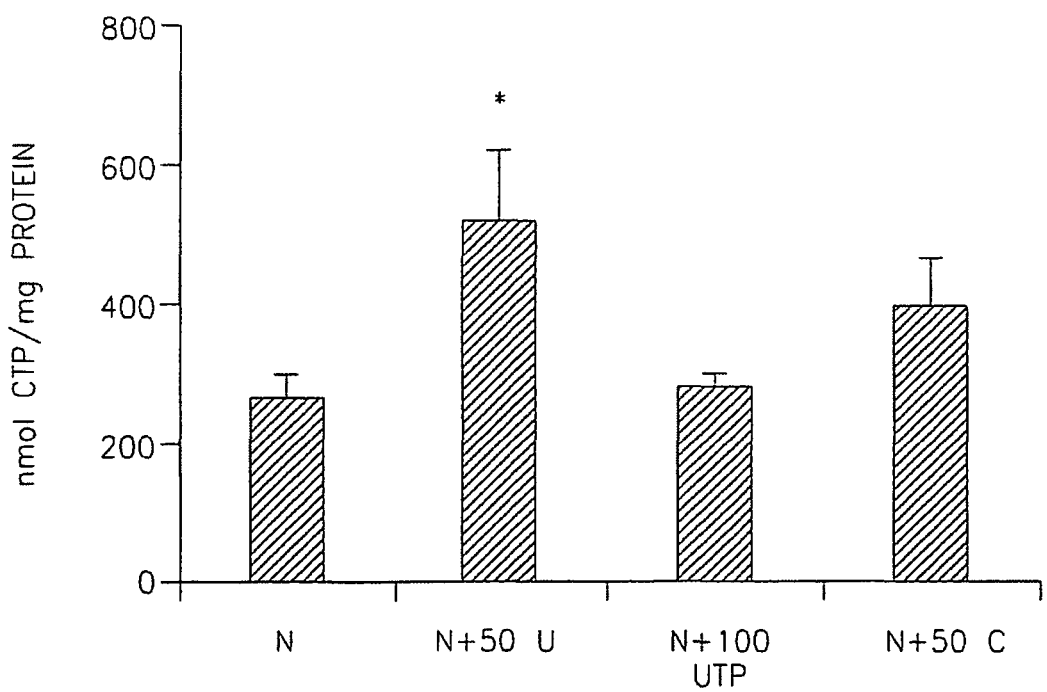
Figure 18:
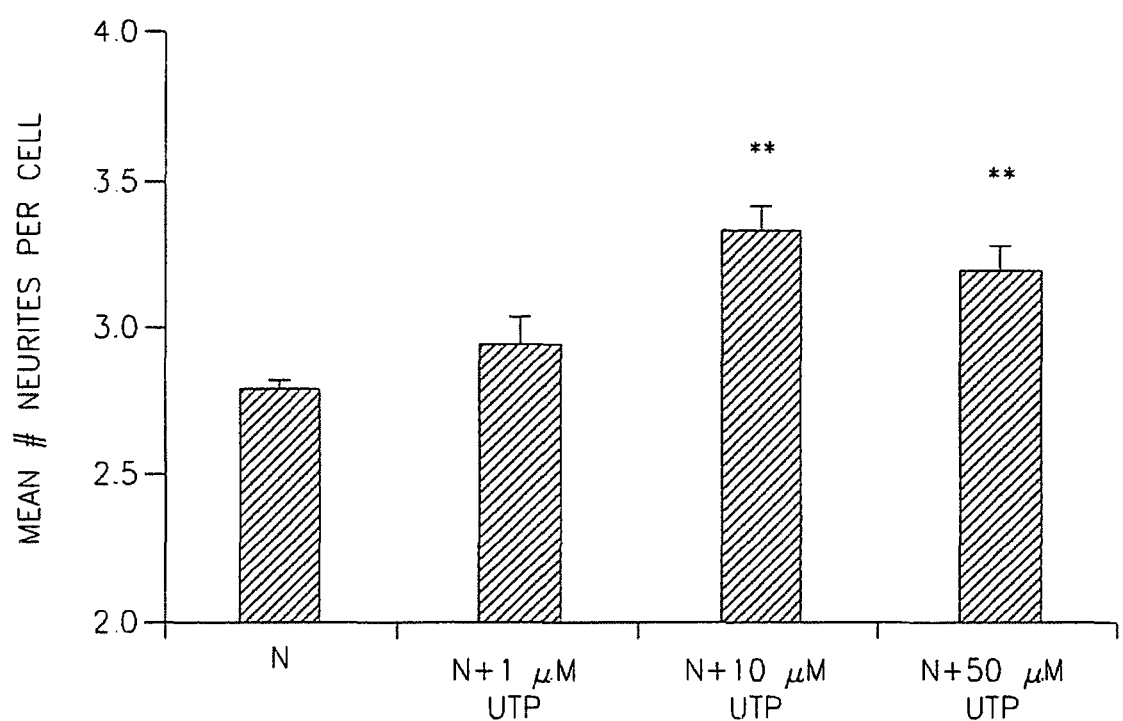
FIG. 18. Phosphatidylinositol (PI) turnover is stimulated by UTP and uridine. Cells were metabolically labeled with [$^3$H]inositol overnight, stimulated with UTP, uridine, or UTP plus PPADS in the presence of lithium at the indicated concentrations, and radio-labeled inositol phosphates derived from PI breakdown were measured by scintillation counting. Values represent means+SEM. *$p<0.05$, ** $p<0.01$ vs. control; #$p<0.05$ vs. 100 μM UTP treatment.
Figure 19A:
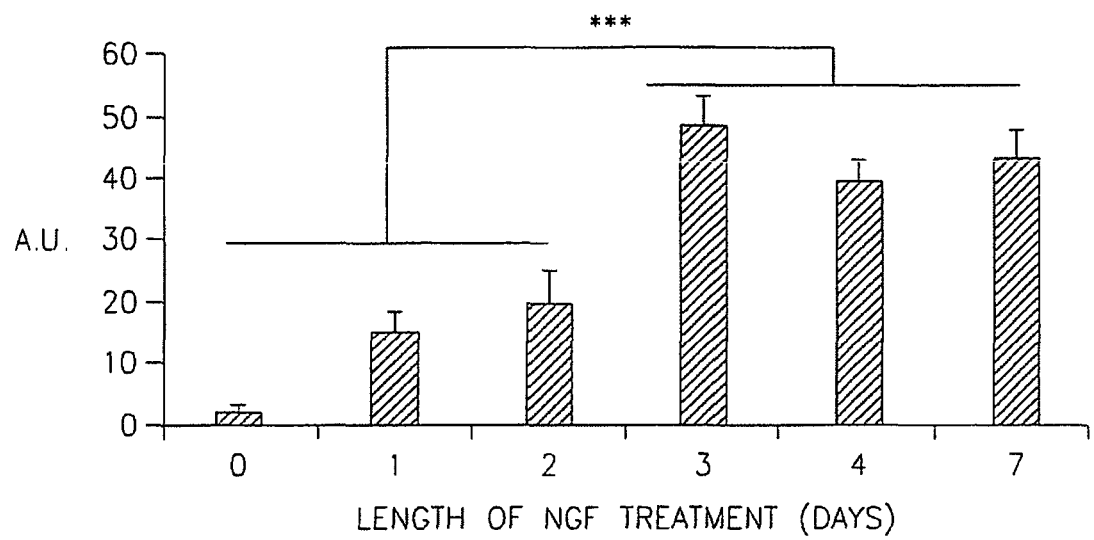
FIG. 19. Oral UMP improves learning and spatial memory in rats. 18-month old rats in restricted environments consumed a control diet or a UMP diet for 6 weeks, and then were tested, using a Morris Water Maze, 4 trials/day for 4 days. Mean time to locate the platform is given in seconds.
Figure 19B:
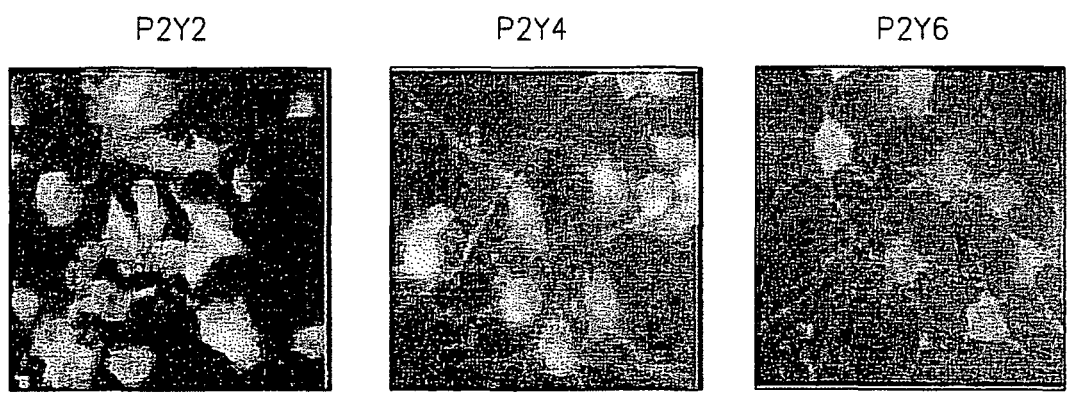

As provided herein, the data in FIGS. 17-19 show that uridine improves several types of memory. The consistency of the effect across different species and in different types of assessments of memory verifies the findings of the present invention. The data in Example 13 further show that the effects of uridine are enhanced by inclusion of a choline. Thus, administration of compositions comprising uridine and choline are effective at improving memory; more effective, in one embodiment, than administration of either uridine or choline alone In another embodiment, the present invention provides a method of restoring a cognitive function in a subject having an impairment in said cognitive function, comprising administering to said subject a uridine, an acyl derivative thereof, a uridine phosphate, uracil, or a salt thereof, thereby restoring a cognitive function in a subject having an impairment in said cognitive function.

In another embodiment, the present invention provides a method of restoring a cognitive function in a subject having an impairment in said cognitive function, comprising administering to said subject a comprising (a) a uridine, an acyl derivative thereof, a uridine phosphate, uracil. Or a salt thereof; and (b) a choline or salt thereof, thereby restoring a cognitive function in a subject having an impairment in said cognitive function.

In another embodiment, the present invention provides a method of treating or reducing an incidence of an age-related cognitive disorder or Age-Associated Memory Impairment (AAMI) in a subject, comprising administering to said subject a uridine, an acyl derivative thereof, a uridine phosphate, uracil, or a salt thereof, thereby treating or reducing an incidence of an age-related cognitive disorder or AAMI in a subject.

In another embodiment, the present invention provides a method of treating or reducing an incidence of an age-related cognitive disorder or AAMI in a subject, comprising administering to said subject a composition comprising (a) a uridine, an acyl derivative thereof, a uridine phosphate, uracil, or a salt thereof; and (b) a choline or salt thereof, thereby treating or reducing an incidence of an age-related cognitive disorder or AAMI in a subject.

In another embodiment, the present invention provides a method of improving or restoring a cholinergic function of a brain of a subject, comprising administering to said subject a uridine, an acyl derivative thereof, a uridine phosphate, uracil, or a salt thereof, thereby improving or restoring a cholinergic function of a brain of a subject.

In another embodiment, the present invention provides a method of improving or restoring a cholinergic function of a brain of a subject, comprising administering to said subject a composition comprising (a) a uridine, an acyl derivative thereof, a uridine phosphate, uracil, or a salt thereof; and (b) a choline or salt thereof, thereby improving or restoring a cholinergic function of a brain of a subject.

In another embodiment of methods of the present invention, administration of a composition of the present invention increases a cytidine level in the subject, thereby mediating one of the effects recited herein (e.g. improving memory or cognitive function, stimulating neural function, membrane synthesis, neurotransmitter release, etc). In another embodiment, the effect is mediated by increasing a level of cytidine triphosphate (CTP) in the subject. In another embodiment, the effect is mediated by increasing a level of CDP-choline in the subject In another embodiment, the effect is mediated by increasing a level of a derivative of cytidine, CTP, CDP-choline in the subject. In another embodiment, the effect is mediated by increasing a level of a metabolite of cytidine, CTP, CDP-choline in the subject. In another embodiment, the effect is mediated without increasing a level of cytidine, CTP, CDP-choline, or a derivative or metabolite thereof. Each possibility represents a separate embodiment of the present invention. Each possibility represents a separate embodiment of the present invention.

Figure 6:
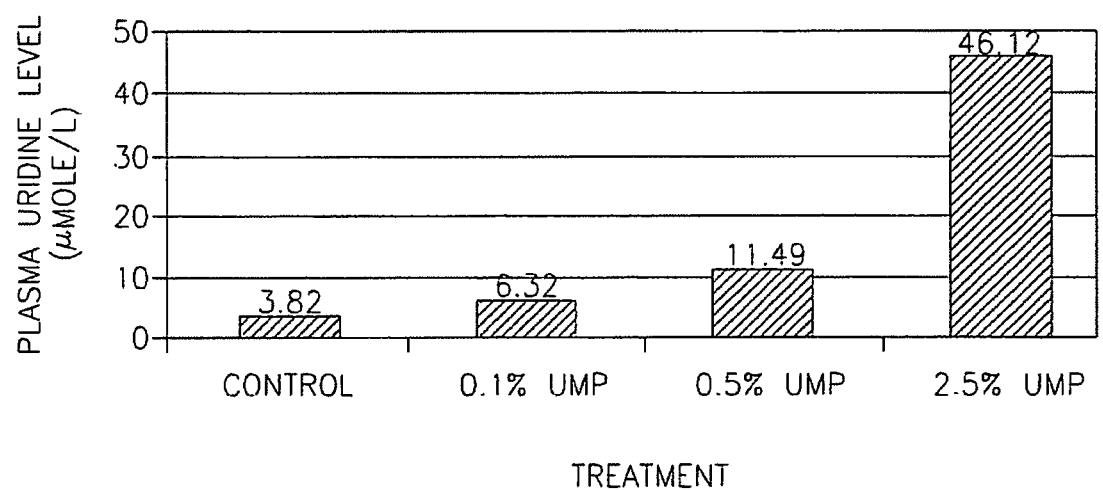
FIG. 6. Oral UMP administration raises brain uridine levels. Depicted are brain uridine levels at various time points following administration or administration of water or UMP.
Figure 7:
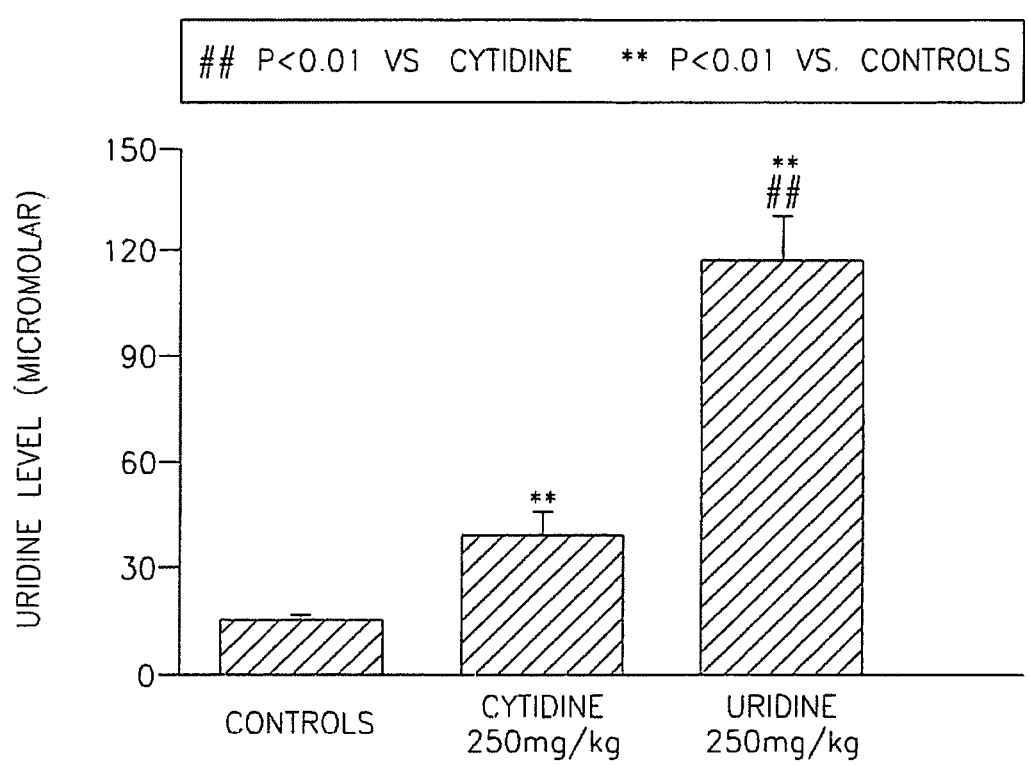
FIG. 7. Uridine is converted to cytidine in the brain. Depicted is the ratio of uridine (100%) to cytidine in plasma (A) and in the brain (B) after oral administration of 250 milligram per kg of body weight (mg/kg) of uridine.
Figure 8:
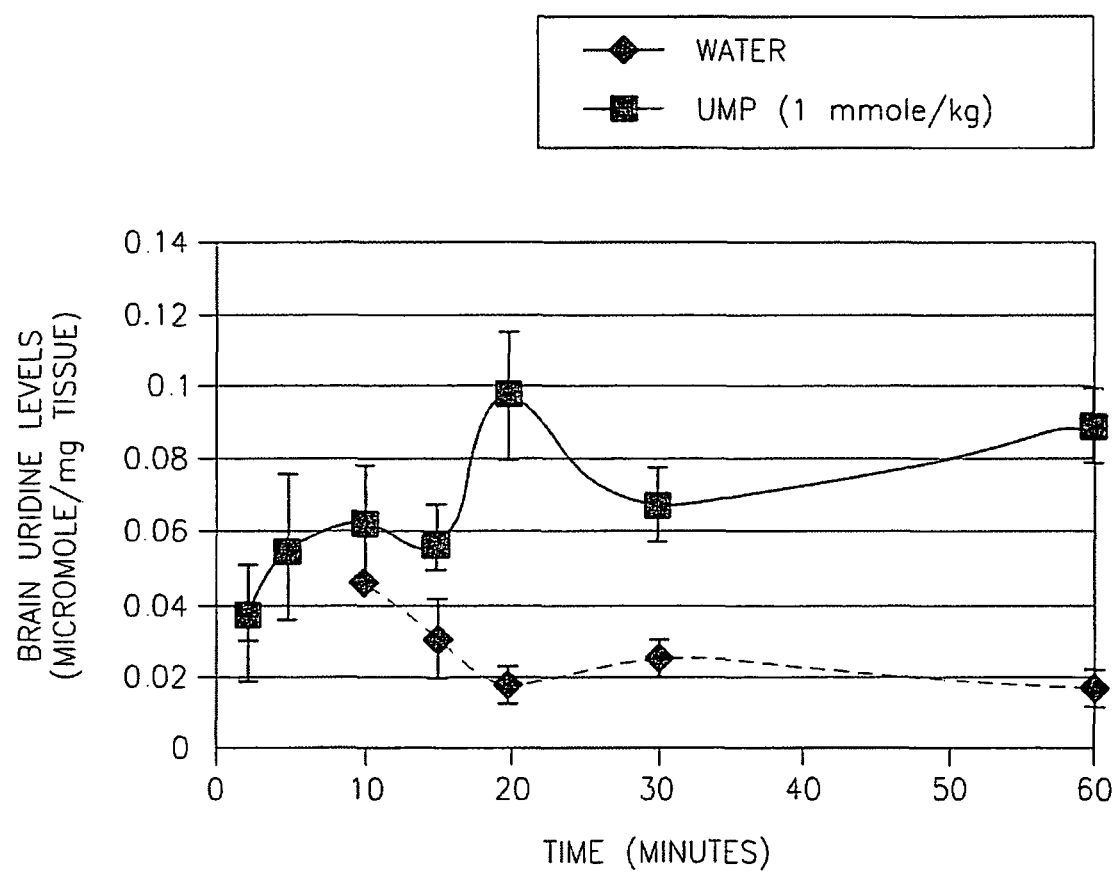
FIG. 8. Oral UMP administration raises brain CDP-choline levels. Depicted are brain CDP-choline levels at various time points following administration or administration of water or UMP.
Figure 9A:
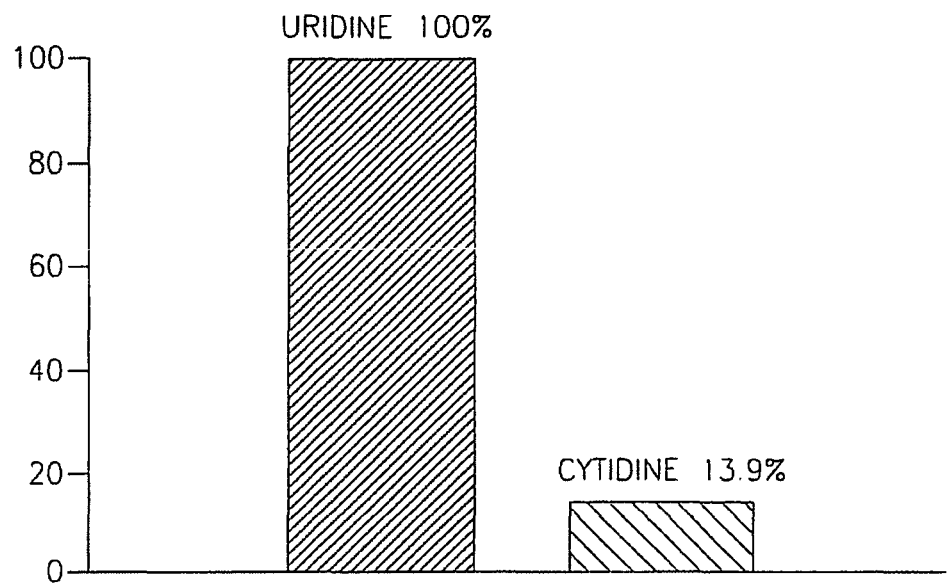
FIG. 9. Uridine increases intracellular levels of CDP-choline in a neural cell line. Cells were incubated for 6 h with the indicated concentrations of uridine. Depicted are the means+/−S.E.M. of six dishes, expressed as picomole (pmol) CDP-choline/mg protein. The experiment was repeated 3 times. **: $p<0.05$.
Figure 9B:
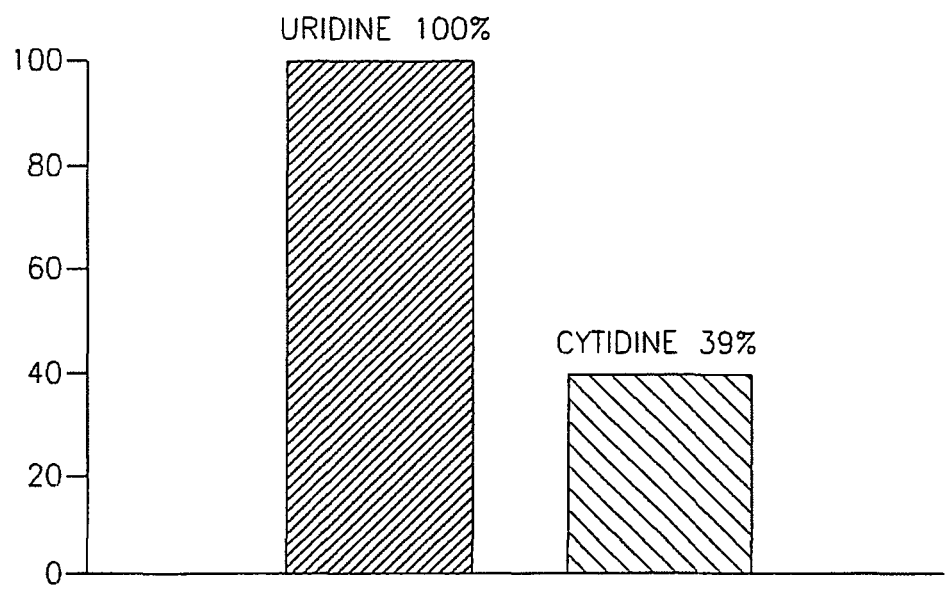

As described herein, FIGS. 7-9 show that orally administered uridine acts rapidly and effectively to raise levels of cytidine in the brain. In combination with FIGS. 3-6, which show that uridine is effectively and rapidly absorbed into the bloodstream, in several species, including humans, these findings demonstrate that administration of uridine raises levels of cytidine, CTP, and CDP-choline. The data in Example 13 further show that the effects of uridine are enhanced by inclusion of a choline.

In one embodiment, the cytidine level is a systemic level. In another embodiment, the cytidine level is a brain level In another embodiment, the cytidine level is a nervous system level. Each possibility represents a separate embodiment of the present invention.

In another embodiment, the increase in cytidine, CTP, or CDP-choline or a derivative or metabolite thereof enables the cell to increase levels of a phospholipid, thereby mediating one of the effects recited herein (e.g. improving memory or cognitive function, stimulating neural function, membrane synthesis, neurotransmitter release, etc). In one embodiment, the phospholipid is phosphatidylcholine (PC). In another embodiment, the phospholipid is phosphatidylethanolarnine (PE). In another embodiment, the phospholipid is phosphatidylserine (PS). In another embodiment, the phospholipid is or a derivative or metabolite of PC, PE, or PS. Each possibility represents a separate embodiment of the present invention.

In another embodiment of methods of the present invention, administration of a composition of the present invention improves a neurological function in a subject, thereby mediating one of the effects recited herein (e.g. improving memory or cognitive function, stimulating neural function, membrane synthesis neurotransmitter release, etc).

In another embodiment, the neurological function that is improved by a method of the present invention is a synaptic transmission. In one embodiment, the synaptic transmission is adjacent to a motor neuron. In another embodiment, the synaptic transmission is adjacent to an interneuron. In one embodiment, the synaptic transmission is adjacent to a sensory neuron. Each type of synaptic transmission represents a separate embodiment of the present invention.

In another embodiment of methods of the present invention, administration of a composition of the present invention stimulates or enhances the outgrowth of neurites of neural cells, thereby mediating one of the effects recited herein (e.g. improving memory or cognitive function, stimulating neural function, membrane synthesis, neurotransmitter release, etc). In another embodiment of methods of the present invention, administration of a composition of the present invention stimulates or enhances the branching of neurites, thereby mediating one of the effects recited herein. In another embodiment, one of the effects recited herein occurs without increasing the number of neurites of the neural cell. Each possibility represents a separate embodiment of the present invention.

"Neurite" refers, in another embodiment, to a process growing out of a neuron. In one embodiment, the process is a dendrite. In another embodiment, the process is an axon. Each type of neurite represents a separate embodiment of the present invention.

In another embodiment of methods of the present invention, administration of a composition of the present invention increases the average number of neurites of neural cells, thereby mediating one of the effects recited herein (e.g. improving memory or cognitive function, stimulating neural function, membrane synthesis, neurotransmitter release, etc). In another embodiment, one of the effects recited herein occurs without increasing the number of neurites of the neural cell. Each possibility represents a separate embodiment of the present invention.

As provided herein, the findings of Example 8 show that when levels of membrane precursors are increased, neurons produce more neurites, with more branches. By increasing its surface area and size, a cell is able, in another embodiment, to form more connections with neighboring cells. The data in Example 13 further show that this effect of uridine is enhanced by inclusion of choline Moreover, an increase in the amount or composition of plasma membrane alters, in one embodiment, neurotransmitter synthesis and release, which also, in one embodiment, affects memory formation. Thus, compounds that promote neurite outgrowth, such as uridine, improve memory and cognition.

In another embodiment of methods of the present invention, administration of a composition of the present invention increases the amount of neural cell membranes, thereby mediating one of the effects recited herein (e.g. improving memory or cognitive function, stimulating neural function, neurotransmitter release, etc). In another embodiment, one of the effects recited herein is achieved by stimulating synthesis of neural cell membranes. The data in Example 13 further show that this effect of uridine is enhanced by inclusion of choline. In another embodiment, stimulating or enhancing the amount of or synthesis of a membrane of a neural cell is partially responsible for mediating one of the effects recited herein. In another embodiment, the composition of the present invention mediates one of the effects recited herein without stimulating or enhancing the amount of or synthesis of neural cell membranes. Each possibility represents a separate embodiment of the present invention.

In one embodiment, the membrane increased by a method of the present invention is a neurite membrane. In another embodiment, the membrane is a dendritic membrane. In another embodiment, the membrane is an axonal membrane. In another embodiment, the membrane is any other type of membrane known in the art. Each type of membrane represents a separate embodiment of the present invention.

In another embodiment, synthesis of a component of a cell membrane or synapse is enhanced. As described herein, findings of the present invention show that uridine enhances synthesis of the PC precursor CDP-choline (Example 5). In another embodiment, the component whose synthesis is enhanced by a method of the present invention is a PC. In another embodiment, the component is a glycerophospholipid. In another embodiment, the component is a phosphatidic acid. In another embodiment, the component is a phosphatidylethanolamine. In another embodiment, the component is a lecithin. In another embodiment, the component is a phosphatidylinositol. In another embodiment, the component is a phosphatidylserine. In another embodiment, the component is a 2-lysolecithin. In another embodiment, the component is a plasmalogen. In another embodiment, the component is a choline plasmalogen. In another embodiment, the component is a phosphatidylglycerol. In another embodiment, the component is a choline diphosphatidylglycerol. In another embodiment, the component is a choline sphingolipid. In another embodiment, the component is a choline sphingomyelin. In another embodiment, the component is any other phospholipid known in the art. Each type of phospholipid represents a separate embodiment of the present invention.

In another embodiment, synthesis of a phospholipid precursor is enhanced. In another embodiment, the phospholipid precursor is CDP-choline (Example 5). In another embodiment, the phospholipid precursor is CTP. In another embodiment, the phospholipid precursor is inositol. In another embodiment the phospholipid precursor is choline. In another embodiment, the phospholipid precursor is glycerol. In another embodiment, the phospholipid precursor is acetate. In another embodiment, the phospholipid precursor is any other phospholipid precursor known in the art. Each phospholipid precursor represents a separate embodiment of the present invention.

In another embodiment of methods of the present invention, administration of a composition of the present invention improves or enhances a function of a neurotransmitter, thereby mediating one of the effects recited herein (e.g. improving memory or cognitive function, stimulating neural function, neurotransmitter release, etc). In another embodiment, improving or enhancing a function of a neurotransmitter occurs by means of increasing a level of the neurotransmitter in a synapse. In another embodiment, improving or enhancing a function of a neurotransmitter occurs by means of increasing the release of the neurotransmitter into a synapse. As described herein, findings of the present invention show that uridine enhances the ability of neurons to synthesize neurotransmitters and repeatedly release them (Example 6). The data in Example 13 further show that this effect of uridine is enhanced by inclusion of choline. Each possibility represents another embodiment of the present invention.

In another embodiment, the release that is enhanced occurs following a stimulation of the neuron. In another embodiment, the release occurs following a depolarization of the neuron. In another embodiment, the release is a basal neurotransmitter release. In another embodiment, the stimulation of the neuron comprises exposure of the neuron to a potassium ion. In another embodiment, the stimulation of the neuron comprises any other means of neural stimulation known in the art. Methods for assessing neural stimulation and release of neurotransmitters are well known in the art, and are described, for example, in Bewick G S, J Neurocytol 32: 473-87, 2003. Each possibility represents a separate embodiment of the present invention. In another embodiment, improving or enhancing a function of a neurotransmitter occurs without changing the level or release of the neurotransmitter in a synapse. Each possibility represents a separate embodiment of the present invention.

Figure 10:
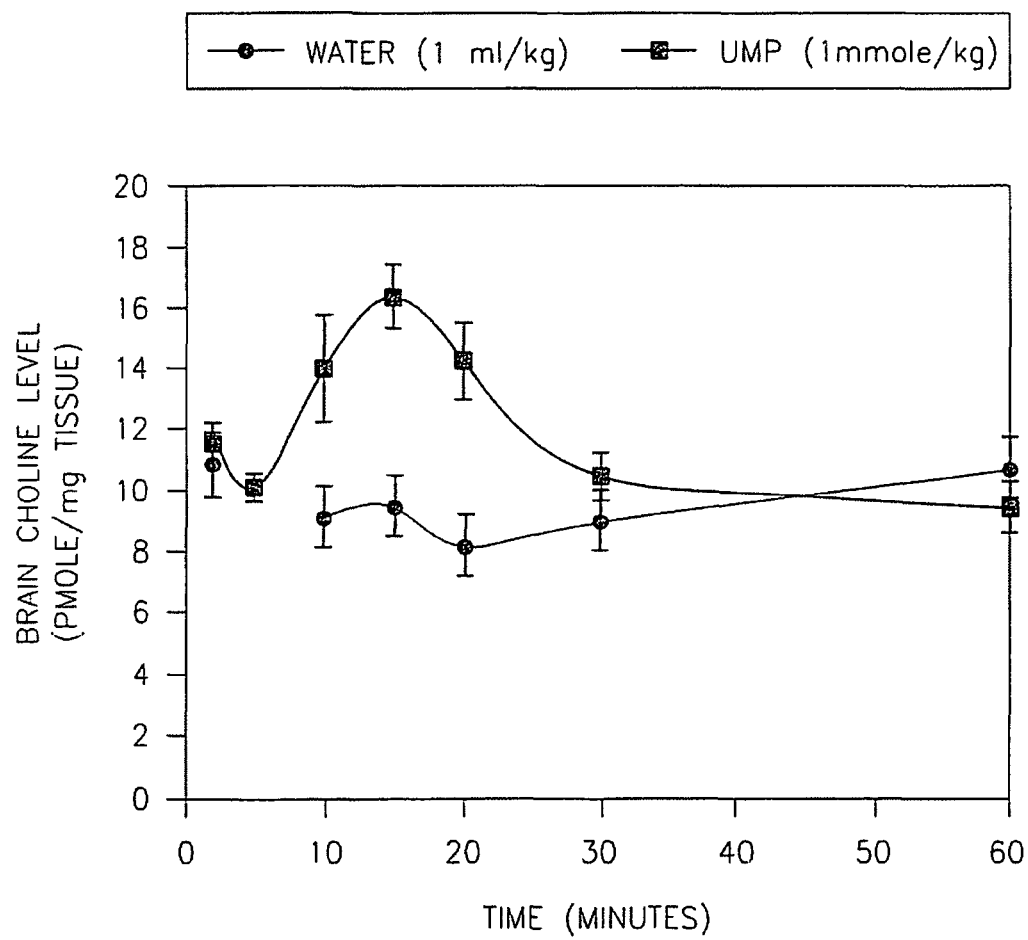
FIG. 10. UMP dietary supplementation significantly increases potassium-evoked dopamine (DA) release in striatal dialysate. (A) Effect of dietary UMP supplementations on $K^+$-evoked striatal DA release. Data were calculated from six to nine measurements at each point (means±standard error of measurement [S.E.M.]). The 100% value represented the mean of the four measurements before potassium stimulation was set at 100%. (B) Data were pooled according to UMP treatment groups. "*" denotes $p<0.05$ compared to corresponding controls.

As provided herein, the findings depicted in FIG. 10 show that uridine significantly improves neurotransmitter function, highlighting the ability of uridine to improve neurological function. The data depicted in FIGS. 11-14 show a beneficial effect of uridine on the morphology of neurites, further demonstrating the ability of uridine to improve neurological function. The data in Example 13 further show that the effects of uridine are enhanced by inclusion of a choline. Thus, administration of compositions comprising uridine and choline are effective at improving neurological function—more effective, in one embodiment, than administration of either uridine or choline alone.

In another embodiment, the neurotransmitter whose levels or activity, or release is affected by methods of the present invention is acetylcholine. In another embodiment, the neurotransmitter is dopamine. In another embodiment, the neurotransmitter is serotonin. In another embodiment, the neurotransmitter is 5-hydroxytryptamine (5-HT) In another any other neurotransmitter known in the art. Each type of neurotransmitter represents a separate embodiment of the present invention.

In another embodiment, stimulating an amount of or a synthesis of the cell membrane is accomplished by stimulating or enhancing a synthesis of a phospholipid (Example 5). In another embodiment, stimulating or enhancing an amount of or a synthesis of a membrane of a neural cell is accomplished by stimulating or enhancing a synthesis of a phospholipid precursor (Example 5). In another embodiment, stimulating or enhancing a synthesis of a phospholipid or a precursor thereof is partially responsible for stimulating an amount of or a synthesis of a membrane of a neural cell. In another embodiment, a composition of the present invention stimulates the amount of or a synthesis of a membrane without stimulating or enhancing a synthesis of a phospholipid or a precursor thereof. Each possibility represents a separate embodiment of the present invention.

In another embodiment, a method of the present invention causes one of the above effects by means of stimulating a P2Y receptor of a neural cell, neuron, or brain cell. In another embodiment, one of the above effects is caused partially as a result of stimulating a P2Y receptor of a neural cell or neuron. In another embodiment, one of the above effects is caused partially or fully by means of stimulating a P2Y receptor of another cell type. In another embodiment, one of the above effects is caused without stimulating a P2Y receptor. Each possibility represents a separate embodiment of the present invention.

In one embodiment, the stimulation of a P2Y receptor is mediated by uridine or a related compound supplied by a composition of the present invention. In another embodiment, the uridine is converted to a second compound that stimulates a P2Y receptor in the cell. In one embodiment, the second compound is uridine-5'-triphosphate. In another embodiment, the second compound is any metabolic product known in the art of uridine or derivative or source thereof. Each compound represents a separate embodiment of the present invention. In one embodiment, the uridine or derivative or source thereof is converted into the second compound intracellularly. In another embodiment, the uridine or derivative or source thereof is converted into the second compound extracellularly. In another embodiment, the uridine or derivative or source thereof is secreted from a cell after being converted into the second compound. In another embodiment, the uridine or derivative or source thereof contacts a different cell after being secreted from the cell in which it was converted to the second compound, and stimulates a P2Y receptor in the different cell. Each possibility represents a separate embodiment of the present invention.

P2Y receptors are a family of receptors known to be involved in platelet activation and other biological functions. They are reviewed in Mahaut-Smith M P et al, Platelets. 2004 15:131-44, 2004.

In one embodiment, the P2Y receptor of the present invention is a P2Y2 receptor. In another embodiment, the P2Y receptor is a P2Y4 receptor. In another embodiment, the P2Y receptor is a P2Y6 receptor. In another embodiment, the P2Y receptor is any other P2Y receptor known in the art. Each possibility represents a separate embodiment of the present invention.

In one embodiment, the P2Y receptor stimulates a second messenger. In one embodiment, the second messenger is a G alpha protein. In another embodiment, the second messenger is a G alpha(q) protein In another embodiment, the second messenger is cAMP. In another embodiment, the second messenger is any other second messenger known in the art. Second messengers, and their associated signaling pathways, are well known in the art, and are described, for example, in Ferguson S, Pharm Rev 53: 1-24, 2001; Huang E et al, Ann Rev Biochem 72: 609-642, 2003; and Blitterswijk W et al, Biochem. J. 369: 199-211, 2003. Each second messenger represents a separate embodiment of the present invention.

In another embodiment, the second messenger stimulates a phospholipase C enzyme. In another embodiment, the second messenger modulates intracellular calcium levels. In another embodiment, the second messenger increases protein kinase C activity. In one embodiment, one or more of the above pathways stimulates membrane production. In another embodiment, the second messenger modulates or stimulates another cellular pathway that stimulates membrane production. Each possibility represents a separate embodiment of the present invention.

In another embodiment, methods and compositions of the present invention increase the level of PC and/or another phosphatide (e.g. phosphatidylinositol, spingomyelin), which in turn increases the levels of a first or second messenger, thereby mediating their effects on memory and/or cognition. In another embodiment, the messenger is an eicosanoid. In another embodiment, the messenger is diacylglcerol. In another embodiment, the messenger is inositol triphosphate. In another embodiment, the messenger is platelet-activating factor (PAF). In another embodiment, the messenger is any other message derived from PC and/or another phosphatide. Each possibility represents another embodiment of the present invention.

Methods for assessing production of a brain cell membrane or neural cell membrane are well known in art. In another embodiment, membrane production is assessed by measuring the level of neurite outgrowth or branching (Example 8). In another embodiment, membrane production is assessed by measuring the level of a membrane marker protein (Example 7). In another embodiment, membrane production is assessed by measuring synthesis of a membrane precursor. In another embodiment, membrane production is assessed by measuring amounts of membrane prior to and following uridine treatment. In another embodiment, membrane production is assessed by measuring biological indicators of membrane turnover. Indicators or cellular membrane turnover are well known in the art, and are described, for example, in Das K P et al, Neurotoxicol Teratol 26(3): 397-406, 2004. Each method of assessing membrane production represents a separate embodiment of the present invention.

In another embodiment, the cell that is the target of methods of the present invention or is contacted in the methods is a neural cell. In another embodiment, the cell is a brain cell. In another embodiment, the cell is any cell in which synthesis of a membrane or a component thereof is enhanced by contact with a composition comprising a uridine and a choline. In another embodiment, the cell is any cell in which a neurological function is enhanced by contact with a composition comprising a uridine and a choline. Each possibility represents a separate embodiment of the present invention.

In another embodiment, the neural cell, neurite, or brain cell of methods of the present invention is newly differentiated. In another embodiment, the cell is not newly differentiated In one embodiment, "newly differentiated" refers to a neuron that has differentiated in the 24 hours prior to commencing administration of the composition of the present invention. In another embodiment, "newly differentiated" refers to a neuron that has differentiated in the 48 hours prior to commencing administration of the composition of the present invention. In another embodiment, "newly differentiated" refers to a neuron that has differentiated in the 72 hours prior to commencing administration of the composition of the present invention In another embodiment, "newly differentiated" refers to a neuron that has differentiated in the 1 week prior to commencing administration of the composition of the present invention. In another embodiment, "newly differentiated" refers to a neuron that completes its differentiation following commencement of administration of the composition of the present invention. Each possibility represents a separate embodiment of the present invention.

Methods of assessing neuronal differentiation are well known in the art, and are described, for example, in Contestabile A et al (Neurochem Int. 45: 903-14, 2004). Each such method represents a separate embodiment of the present invention.

In another embodiment, methods and compositions of the present invention comprise a uridine salt or administration thereof. In another embodiment, the uridine salt is a uridine-5'-monophosphate (UMP). In another embodiment, the uridine salt is a uridine-5'-diphosphate (UDP). In another embodiment, the uridine salt is a uridine-5'-triphosphate (UTP). In another embodiment, the uridine salt is UDP glucose. In another embodiment, the uridine salt is any known salt of a uridine precursor, derivative or source thereof Each possibility represents a separate embodiment of the present invention.

In another embodiment, a uridine precursor is administered in methods of the present invention. In one embodiment, the uridine precursor that is administered is a cytidine-5'-monophosphate. In another embodiment, the uridine precursor that is administered is a cytidine-5'-diphosphate (CDP). In another embodiment, the uridine precursor that is administered is a CDP-glucose. In another embodiment, the uridine precursor that is administered is any pharmacologically acceptable uridine precursor, derivative or metabolite known in the art.

In another embodiment, a uridine derivative is administered in methods of the present invention. The term "derivative" in one embodiment refers to a compound chemically related to uridine in such a way that uridine is converted to the derivative in a subject's body. In another embodiment, "derivative" refers to a compound chemically related to uridine in such a way that the derivative is converted to uridine in a subject's body. In one embodiment, the conversion occurs via one or more stable intermediates. In another embodiment, the conversion occurs directly. Each possibility represents a separate embodiment of the present invention.

In another embodiment, a uridine metabolite is administered in methods of the present invention.

In another embodiment of methods and compositions of the present invention, uridine is administered in the form of a uridine-based compound or a uridine precursor. In another embodiment, the uridine-based compound or uridine precursor is a uridine salt. In another embodiment, the uridine-based compound or uridine precursor is a uridine phosphate. In another embodiment, the uridine-based compound or uridine precursor is an acylated uridine derivative. In another embodiment, therapeutically or pharmacologically effective doses of acyl derivatives of uridine or mixtures thereof, e.g. those disclosed in U.S. Pat. No. 5,470,838, are also administered. In another embodiment, the uridine-based compound or uridine precursor is uracil or a salt thereof. In another embodiment, the uridine-based compound or uridine precursor is deoxyuridine, a salt thereof, or a phosphate thereof. Each uridine-based compound or uridine precursor represents a separate embodiment of the present invention.

In another embodiment of methods and compositions of the present invention, uridine is administered in the form of a uridine source. In another embodiment, the uridine source is a uridine-rich food. In another embodiment, the uridine source is a uridine-rich dietary product. In another embodiment, the uridine source is algae.

In another embodiment, the uridine source is a RNA extract or DNA extract from a cellular material or from a tissue. In other embodiments, the cellular material or tissue is obtained from plants, yeasts, micro-organisms, animals, milk, eggs, or other animal products. In other embodiments, the extract is obtained by isolating RNA and/or DNA. In other embodiments, the extract is obtained by purifying nuclear, mitochondrial or endoplasmatic reticular material. In another embodiment, isolation of the extract further comprises concentrating the uridines relative to the other pyrimidines, purines, and/or phosphates or deoxy variants thereof that are present therein. In another embodiment, at least 50% of the nucleoside bases and/or phosphates or deoxy variants thereof that are present in the extract contains are uridine and/or phosphates or deoxy variants thereof. In another embodiment, the percentage is at least 55%. In another embodiment, the percentage is at least 60%. In another embodiment, the percentage is at least 65%. In another embodiment, the percentage is at least 70%. In another embodiment, the percentage is at least 75%. In another embodiment, the percentage is at least 80%. In another embodiment, the percentage is at least 85%. In another embodiment, the percentage is at least 90%. In another embodiment, the percentage is at least 95%. In another embodiment, the percentage is at least 98%. In another embodiment, the percentage is close to 100%. In another embodiment, no detectable amounts of nucleoside bases other than uridine are present. Each possibility represents a separate embodiment of the present invention.

In another embodiment a mixture of two or more of the above uridine-related compounds is administered. Each type of uridine precursor, derivative, metabolite, or source represents a separate embodiment of the present invention Each uridine source, uridine-related compound, or combination thereof represents a separate embodiment of the present invention.

"Uridine" refers, in another embodiment, to any uridine phosphate, uridine precursor, uridine metabolite, uridine-based compound, or salt thereof mentioned above. In another embodiment, "uridine" refers to any uridine or related compound that is known in the art. Each possibility represents a separate embodiment of the present invention.

In another embodiment, methods and compositions of the present invention comprise administration of choline. In another embodiment, the choline is a choline salt. In another embodiment, the salt is choline chloride. In another embodiment, the salt is choline bitartrate. In another embodiment, the salt is choline stearate. In another embodiment, the salt is any other choline salt known in the art. Each possibility represents a separate embodiment of the present invention.

In another embodiment, the choline is a choline-based compound, e.g. a choline ester.

In another embodiment, the choline is a compound that dissociates to choline. In one embodiment, the compound is sphingomyelin. In one embodiment, the compound is cytidine-diphosphocholine (CDP-choline). In another embodiment, the compound is citicoline. In another embodiment, the compound is an acylglycerophosphocholine. In another embodiment, the compound is lecithin. In another embodiment, the compound is lysolecithin. In another embodiment, the compound is glycerophosphatidylcholine. In another embodiment a mixture of two or more of the above choline-related compounds is administered.

"Choline" refers, in other embodiments, to any choline phosphate, choline precursor, choline metabolite, choline-based compound, or salt thereof mentioned above. In another embodiment, "choline" refers to any choline or related compound that is known in the art. Each possibility represents a separate embodiment of the present invention.

In another embodiment of methods of the present invention, the choline or choline-related compound is administered in such a manner that a choline level of at least 20-30 nanomoles is attained in the subject's blood or brain. In another embodiment, a choline level of 10-50 nanomoles is attained In another embodiment, a choline level of 5-75 nanomoles is attained. In another embodiment, a choline level of 25-40 nanomoles is attained. In another embodiment, a choline level of 30-35 nanomoles is attained. Each possibility represents a separate embodiment of the present invention.

In another embodiment, the choline, derivative, source, or precursor thereof is administered at a dosage of 20 mg-50 g per day. In another embodiment, the dosage is about 50 mg-30 g per day. In another embodiment, the dosage is about 75 mg-20 g per day. In another embodiment, the dosage is about 100 mg-20 g per day. In another embodiment, the dosage is about 100 mg-10 g per day. In another embodiment, the dosage is about 200 mg-8 g per day. In another embodiment, the dosage is about 400 mg-6 g per day. In another embodiment, the dosage is about 600 mg-4 g per day. In another embodiment, the dosage is about 800 mg-3 g per day. In another embodiment, the dosage is about 1-2.5 g per day. In another embodiment, the dosage is about 1.5-2 g per day. In another embodiment, the dosage is about 5 mg-5 g per day. In another embodiment, the dosage is about 5 mg-50 g per day. Each dosage range represents a separate embodiment of the present invention.

In another embodiment, a composition of the present invention is administered at a dose that produces a desired effect in at least 10% of a population of treated patients. In another embodiment, the dose is that which produces the effect in at least 20% of treated patients. In another embodiment, the effect is produced in at least 30% of treated patients. In another embodiment, the effect is produced in at least 40% of the patients. In another embodiment, the effect is produced in at least 50% of the patients. In another embodiment, the effect is produced in at least 60% of the patients. In another embodiment, the effect is produced in at least 70% of the patients. In another embodiment, the effect is produced in at least 80% of the patients. In another embodiment, the effect is produced in at least 90% of the patients. In another embodiment, the effect is produced in over 90% of the patients. Each possibility represents a separate embodiment of the present invention.

In one embodiment, the subject of methods of the present invention is a mammal. In another embodiment, the subject is a human. In another embodiment, the subject is a rodent. In another embodiment, the subject is a laboratory animal. In another embodiment, the subject is a male. In another embodiment the subject is a female. In another embodiment, the subject is any other type of subject known in the art. Each possibility represents a separate embodiment of the present invention.

In another embodiment, an additional therapeutic compound is administered to the subject as part of a method of the present invention. In another embodiment, the uridine or precursor, derivative or source thereof is the sole active ingredient in the composition utilized thereby. In another embodiment, the uridine or precursor, derivative or source thereof and choline or precursor, derivative or source thereof are the sole active ingredients in the composition utilized thereby. Each possibility represents a separate embodiment of the present invention.

In one embodiment, the additional therapeutic compound is a drug that acts as a uridine phosphorylase inhibitor; e.g. benzyl barbiturate or derivatives thereof. In another embodiment, the additional therapeutic compound is a drug that increases uridine availability. In another embodiment, the additional therapeutic compound is a uridine secretion-inhibiting compound, e.g. dilazep or hexobendine. In another embodiment, the additional therapeutic compound is a uridine renal transport competitors, e.g. L-uridine, L-2',3'-dideoxyuridine, and D-2',3'-dideoxyuridine. In another embodiment, the additional therapeutic compound is a drug that acts in synergy with uridine in generation of a phospholipid. In another embodiment, the additional therapeutic compound is a compound which competes with uridine in kidney clearance, e.g. L-uridine, L-2',3'-dideoxyuridine, and D-2',3'-dideoxyuridine or mixtures thereof as disclosed in U.S. Pat. Nos. 5,793,449 and 5,567,689. In another embodiment, the additional therapeutic compound is any other compound that is beneficial to a subject.

In other embodiments, the additional therapeutic compound is sphingomyelin, an acylglycerophosphocholine, a lecithin, a lysolecithin, a glycerophosphatidylcholine, or a mixture thereof. Each additional therapeutic compound represents a separate embodiment of the present invention.

In another embodiment of the methods of the present invention, the uridine and/or choline is carried in the subjects' bloodstream to the subject's brain cell or neural cell. In another embodiment, the uridine and/or choline is carried by diffusion to the subject's brain cell or neural cell. In another embodiment, the uridine and/or choline is carried by active transport to the subject's brain cell or neural cell. In another embodiment, the uridine and/or choline is administered to the subject in such a way that it directly contacts the subject's brain cell or neural cell Each possibility represents a separate embodiment of the present invention.

In another embodiment, methods of the present invention comprise administering a pharmaceutical composition comprising an analog, derivative, isomer, metabolite, pharmaceutically acceptable salt, pharmaceutical product, hydrate, N-oxide, or any combination thereof of a uridine or precursor, derivative or source thereof. In another embodiment, methods and compositions of the present invention further comprise an analog, derivative, isomer, metabolite, pharmaceutically acceptable salt, pharmaceutical product, hydrate, N-oxide, or any combination thereof of a choline or derivative or source thereof.

Pharmaceutical compositions of the present invention are, in other embodiments, administered to a subject by any method known to a person skilled in the art, such as parenterally, paracancerally, transmucosally, transdermally, intramuscularly, intravenously, intra-dermally, subcutaneously, intra-peritoneally, intra-ventricularly, intra-cranially, intra-vaginally or intra-tumorally. Each possibility represents another embodiment of the present invention.

In another embodiment of methods and compositions of the present invention, the composition comprising the uridine or precursor, derivative or source thereof and/or choline or derivative or source thereof further comprises a lipid fraction. In another embodiment, the lipid fraction comprises more than 10% (by wt) omega-3 fatty acids In another embodiment, the lipid fraction comprises more than 10% omega-3 fatty acids having a length larger than 18 carbon atoms. In another embodiment, the percentage of omega-3 fatty acids, or of omega-3 fatty acids longer than 18 carbon atoms, is over 16%. In another embodiment, the percentage is over 20%. In another embodiment, the percentage is over 25%. In another embodiment, the percentage is over 30%. In another embodiment, the percentage is over 35%. In another embodiment, the percentage is over 40%. In another embodiment, the percentage is over 45%. In another embodiment, the percentage is 10-40%. In another embodiment, the percentage is over 10-50%. In another embodiment, the percentage is 16-40%. In another embodiment, the percentage is over 16-50%. In another embodiment, the percentage is 20-40%. In another embodiment, the percentage is over 20-50%. In another embodiment, the percentage is 30-40%. In another embodiment, the percentage is over 30-50%. Each possibility represents a separate embodiment of the present invention.

In another embodiment, the lipid fraction of the composition comprising the uridine or precursor, derivative or source thereof comprises docosahexaenoic acid, eicosapentaenoic acid, docosapentaenoic acid, or a combination thereof. In another embodiment, the sum of these fatty acids is more than 50% by weight of the omega-3 long chain fatty acids that are present. In another embodiment, the sum of these fatty acids is more than 60% of the omega-3 long chain fatty acids. In another embodiment, the sum of these fatty acids is more than 70% of the omega-3 long chain fatty acids In another embodiment, the sum of these fatty acids is more than 75% of the omega-3 long chain fatty acids. In another embodiment, the sum of these fatty acids is more than 80% of the omega-3 long chain fatty acids: In another embodiment, the sum of these fatty acids is more than 85% of the omega-3 long chain fatty acids.

In another embodiment, the ratio of the sum of these fatty acids (DHA, DPA, and EPA) to linoleic acid is greater than 0.5. In another embodiment, the ratio is greater than 0.6. In another embodiment, the ratio (is greater than 0.7. In another embodiment, the ratio is greater than 0.8. In another embodiment, the ratio is greater than 1. In another embodiment, the ratio is greater than 1.5. In another embodiment, the ratio is greater than 2. In another embodiment, the ratio is greater than 3. In another embodiment, the ratio is greater than 5. In another embodiment, the ratio is greater than 7. In another embodiment, the ratio is greater than 10. In another embodiment, the ratio is greater than 12. In another embodiment, the ratio is greater than 15. In another embodiment, the ratio is from 1-25. In another embodiment, the ratio is from 2-22. In another embodiment, the ratio is from 3-22. In another embodiment, the ratio is from 5-20. In another embodiment, the ratio is from 7-15. In another embodiment, the ratio is from 10-12.

In another embodiment, the lipid fraction of the composition comprising the uridine or precursor, derivative or source thereof contributes 20-60% of the energy content of the composition. In another embodiment, the energy contribution from the lipid fraction is 25-55%. In another embodiment, the energy contribution is 30-50%. In another embodiment, the energy contribution is 32-45%.

The weight ratio of DHA to EPA in the lipid fraction of the composition comprising the uridine or precursor, derivative or source thereof is, in another embodiment, from 1-20. In another embodiment, the range is from 2-18. In another embodiment, the range is from 3-16. In another embodiment, the range is from 5-14. In another embodiment, the range is from 7-12.

In another embodiment, a composition of methods and compositions of the present invention is a nutritional supplement (in another embodiment, a drink) that comprises:

| | |
|---|---|
| UMP | 0.5 g |
| choline | 0.3 g |
| fish oil | 3.7 g |
| carbohydrate | 9.0 g |
| milk protein | 3 g |

In another embodiment of methods and compositions of the present invention, the pharmaceutical compositions are administered orally, and are thus formulated in a form suitable for oral administration. In another embodiment, the form is nutritional formula. In another embodiment, the form is a solid preparation. In another embodiment, the form is a semi-solid preparation. In another embodiment, the form is a liquid preparation. In other embodiments, the solid oral formulations are tablets, capsules, pills, granules, pellets, or the like. In another embodiment, the semi-solid preparation is a gel; in another embodiment, a sports gel. In other embodiments, the liquid oral formulations are solutions, suspensions, dispersions, emulsions, oils, or the like.

Each of the above types of lipid fractions of the composition comprising the uridine or precursor, derivative or source thereof represents a separate embodiment, of the present invention.

In another embodiment, the active ingredient(s) are formulated in a capsule. In another embodiment, the compositions of the present invention comprise, in addition to the active compound and the inert carrier or diluent, a hard gelating capsule.

In another embodiment, the pharmaceutical compositions are administered by intravenous, intra-arterial, or intra-muscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In another embodiment, the pharmaceutical compositions are administered topically to body surfaces and are thus formulated in a form suitable for topical administration. Suitable topical formulations include gels, ointments, creams, lotions, drops and the like. For topical administration, compositions of present invention are applied as solutions, suspensions, or emulsions in a physiologically acceptable diluent with or without a pharmaceutical carrier.

In another embodiment, the pharmaceutical composition is administered as a suppository, for example a rectal suppository or a urethral suppository. In another embodiment, the pharmaceutical composition is administered by subcutaneous implantation of a pellet. In another embodiment, the pellet provides for controlled release of the active agent(s) over a period of time.

In another embodiment, the active compound is delivered in a vesicle, e.g. a liposome.

In other embodiments, carriers or diluents used in methods of the present invention include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

In another embodiment, parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In other embodiments, the compositions further comprises binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants Each of the above excipients represents a separate embodiment of the present invention.

In another embodiment, the pharmaceutical composition is delivered in a controlled release system. For example, the agent may be administered using intravenous infusion, an implantable osmotic pump, a transdermal patch, liposomes, or other modes of administration in one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials are used; e.g. in microspheres in or an implant. In yet another embodiment, a controlled release system is placed in proximity to the therapeutic target, i.e., the brain, thus requiring only a fraction of the systemic dose (see, e.g., Goodson, in Medical Applications of Controlled Release, supra, vol. 2, pp. 115-138 (1984); and Langer R, Science 249: 1527-1533 (1990).

The compositions also include, in another embodiment, incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also included in the present invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity is achieved, in another embodiment, by the administration of such polymer-compound abducts less frequently or in lower doses than with the unmodified compound.

An active component is, in another embodiment, formulated into the composition as a neutralized pharmaceutically acceptable salt form Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimetliylamine, 2-ethylamino ethanol, histidine, procaine, and the like.

Each of the above additives, excipients, formulations and methods of administration represents a separate embodiment of the present invention.

EXPERIMENTAL DETAILS SECTION

Example 1

Measurement of Cytidine by HPLC without Interference from Tyrosine

Materials and Methods

Sample Preparation 1-milliliter (mL) samples of heparinized plasma were spiked with 1 µg fluoro-uridine for use as an internal standard, then deproteinized by adding methanol (5 mL). Samples were centrifuged, lyophilized, reconstituted in 5 mL of 0.25 N ammonium acetate (pH 8.8), then immediately purified over boronate affinity columns.

Boronate Affinity Columns

All steps were performed at 4° C. Boronate affinity columns (Affigel-601, Bio-Rad) were primed with two 5-mL ammonium acetate washes, samples were applied, and columns were washed again with ammonium acetate, after which the nucleosides were eluted with 0.1 N formic acid (7 mL). Eluates were lyophilized, then reconstituted in 100 µL water for HPLC analysis. Boronate affinity columns bind many biological molecules, including the nucleotide bases adenosine, cytidine, guanosine, thymidine and uridine.

HPLC

HPLC analysis was performed using a Beckman System Gold apparatus (Beckman Instruments) equipped with a Rainin Dynamax Microsorb C18 column (3 µm packing; 4.6× 100 mm) at room temperature. The standard HPLC method is described in Lopez-Coviella et al, (J. Neurochem 65: 889-894, 1995). For modified HPLC, an isocratic elution buffer was used containing 0.004 N potassium phosphate buffer (pH 5.8) and 0.1% methanol instead of formic acid, flowing at 1 mL/min and heated to 35°.

Results

Figure 2:
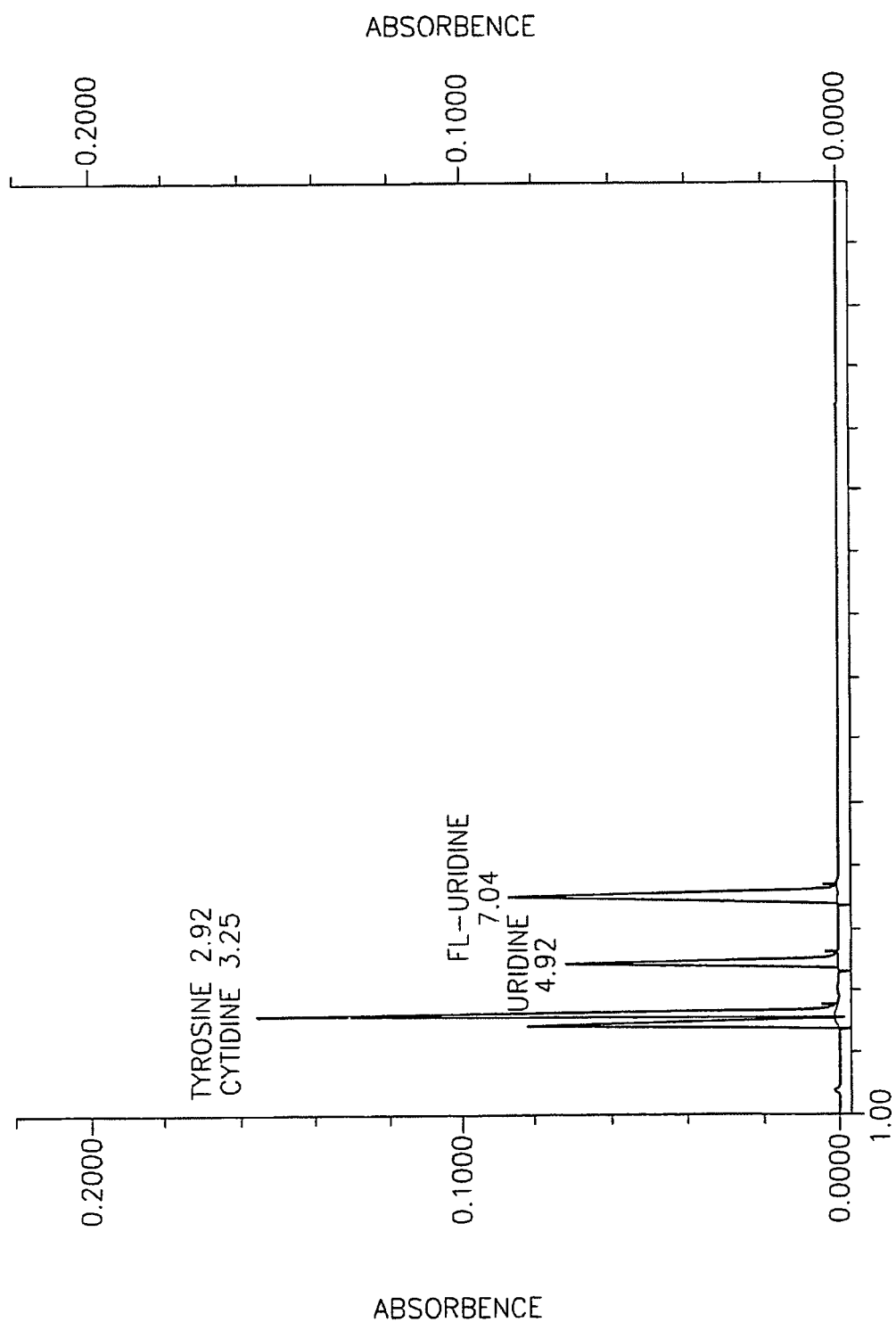
FIG. 2 illustrates distinct cytidine (3.25) and tyrosine (2.92) peaks when tested by a modified HPLC method which utilizes elution buffer with low methanol.

A standard HPLC method for measuring nucleosides yields separate peaks for uridine and cytidine; however, a coincidence of the cytidine and tyrosine peaks precludes accurate measurement of cytidine levels as shown for human plasma samples (FIG. 1). Tyrosine is present in many biological fluids, e.g., plasma or cerebrospinal fluid (CSF). In the present Example, a modified HPLC method was used which distinguished cytidine and tyrosine peaks, permitting accurate measurement of cytidine levels (FIG. 2).

Example 2

Oral Administration of UMP Increases Plasma Uridine Levels in Humans

Materials and Experimental Methods

Study Design

Eight healthy subjects (5 male, 3 female, 27-67 years old) were instructed to fast overnight and given sequentially increasing doses (500, 1000, and 2000 mg) of disodium UMP (Numico, Wageningen, NL) at 7-8 AM on each of three days, separated by at least a three-day washout period. All subjects were given lunch. Blood samples were drawn over an eight-hour period into heparinized tubes. Plasma was treated with methanol to precipitate protein, extracted with chloroform, and an aliquot of the aqueous layer lyophilized, dissolved in water, and assayed by HPLC with UV detection.

Statistical Analyses

Statistical analyses were carried out with SPSS 12.0. Data were represented as mean±SEM. Unpaired Student's t test, one-way analysis of variance (ANOVA), ANOVA with repeated measures, two-way ANOVA were used to assess the statistical effects, as described in detail in the context. Tukey's HSD post hoc analyses were conducted when appropriate. The significance level was set at $p<0.05$.

Results

Figure 3:
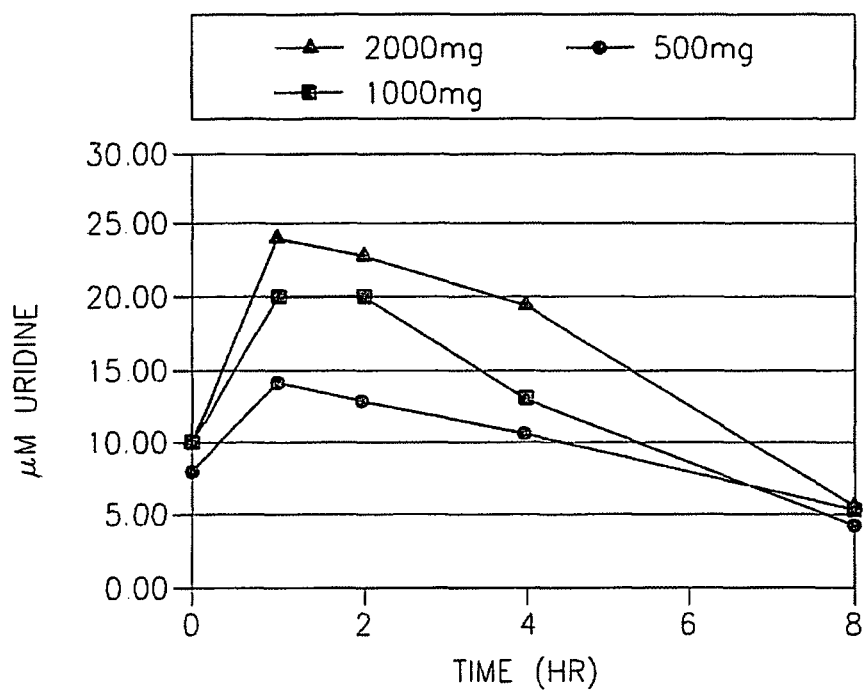
FIG. 3. Oral UMP administration raises blood uridine levels in humans. Depicted is the ratio of uridine (set as 100% value) to cytidine in plasma after oral administration of 250 milligram per kg of body weight (mg/kd) of uridine.
Figure 4:
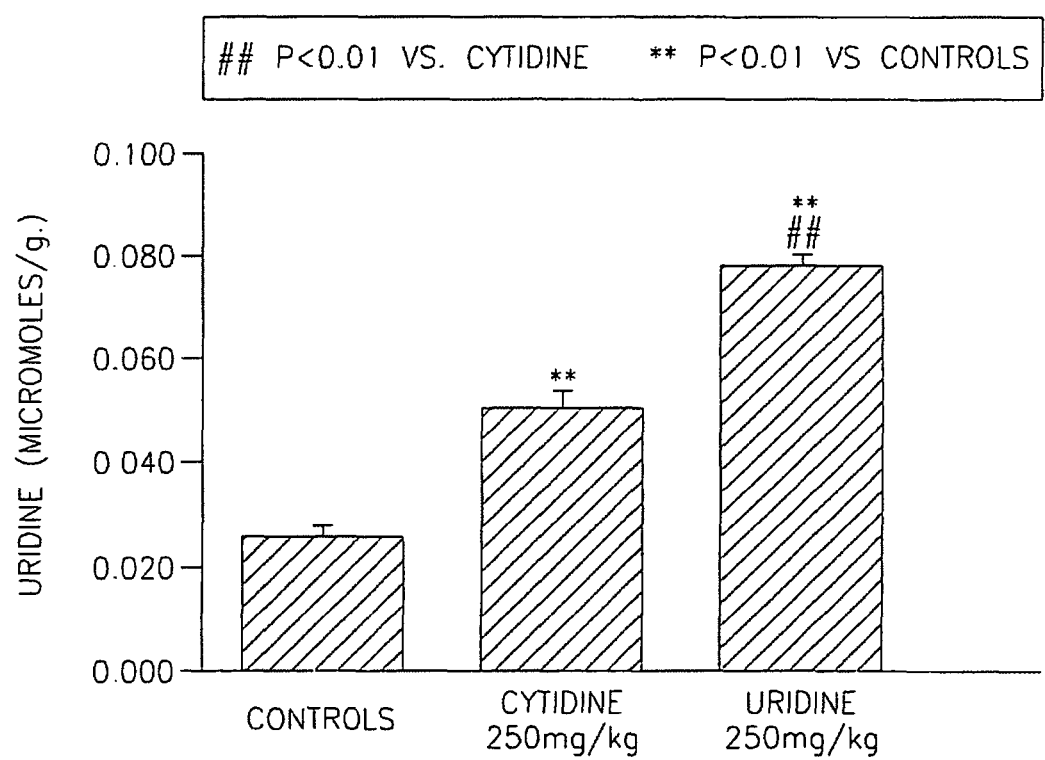
FIG. 4. Oral uridine administration raises blood uridine levels in gerbils. Depicted are plasma uridine levels 60 minutes following mock administration or administration of cytidine or uridine. **: $p<0.01$ vs. mock-fed control; ##: $p<0.01$ vs. cytidine.

Subjects were administered 500, 1000, or 2000 mg UMP orally, and blood uridine levels were measured at baseline and 1, 2, 4 and 8 hours (hr) following dosing. Plasma uridine levels were assayed as described in Example 1. Plasma uridine levels increased in response to oral UMP in a dose-dependent fashion, then returned to baseline levels within 8 hr (FIG. 3). Similar results were observed in gerbils (FIG. 4).

Example 3

Oral Administration of Uridine or UMP Increases Brain Uridine Levels in Gerbils Materials and Experimental Methods Experimental Design Groups of eight to nine male gerbils (60-80 g) were fasted overnight, administered (a) uridine (Sigma, St. Louis, Mo.; 250 mg/kg body weight) or disodium UMP (1 mmol/kg body weight, a dose equivalent to 250 mg/kg uridine by gavage) and sacrificed by decapitation under Telazol anesthesia one hour later. Blood collected from the neck was collected into tubes containing EDTA and was treated as described above for Example 2.

Gerbil Brain Tissue Preparation

Brains were quickly removed from the skull after decapitation, frozen on dry ice, homogenized in 80% methanol, centrifuged, lyophilized and analyzed as described for blood in Example 2.

Results

Figure 5:
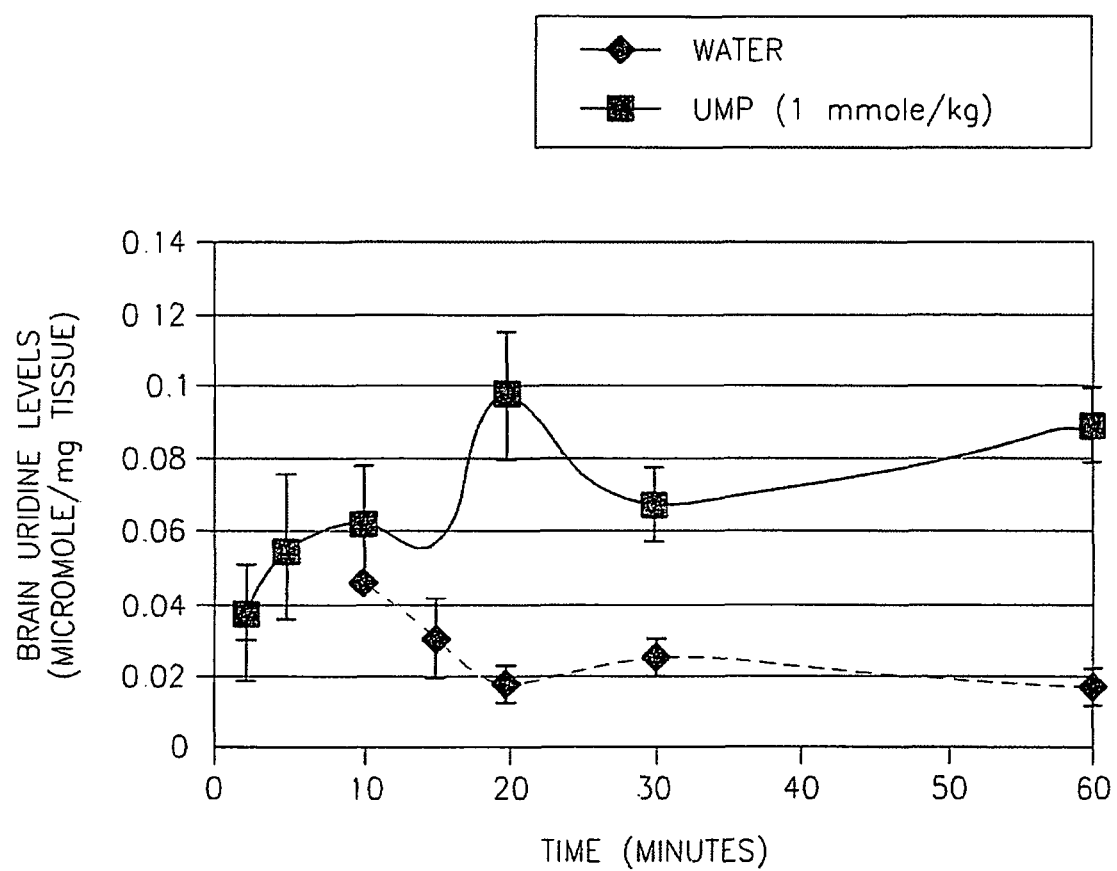
FIG. 5. Oral uridine administration raises brain uridine levels. Depicted are brain uridine levels 60 minutes following mock administration or administration of cytidine or uridine. **: $p<0.01$ vs. mock-fed control; ##: $p<0.01$ vs. cytidine.

To ascertain whether oral administration of uridine can raise plasma uridine levels, gerbils were fed by gavage 250 mg/kg cytidine or uridine. 60 minutes (min) later, the brains were homogenized, and the uridine levels were assayed. Oral administration of cytidine resulted in a two-fold increase in brain uridine levels, and oral administration of uridine resulted in a greater than a three-fold increase in brain uridine levels, relative to the control animals (FIG. 5). All differences between groups were statistically significant.

In a separate experiment to assess the time course of the increase in plasma uridine levels, gerbils were administered either water or 1 millimole (mmol) UMP per kilogram (kg) body weight, were sacrificed at various time points in the following 60 min, and brain uridine levels were assessed. Brain uridine levels increased within 10 min of uridine administration, reaching peak levels within 30 min, similar to the results observed with plasma uridine levels (FIG. 6). Thus, orally administered uridine is efficiently transported into the brain.

Example 4

Uridine is Readily Converted to Cytidine in the Brain

In a separate experiment, gerbils were orally administered 250 mg/kg body weight uridine, and 60 min later plasma and brain levels of cytidine and uridine were assessed. The fold-increases relative to control animals was calculated and are depicted in FIGS. 7A (plasma) and 7B (brain). In each case, the fold-increase of cytidine was normalized to the fold increase of uridine, which was arbitrarily set as 100%. These results indicate that (a) uridine in the bloodstream is transported into the brain and (b) uridine is metabolically processed differently in the brain than in plasma; specifically, it is more efficiently converted to cytidine than in plasma.

Example 5

Uridine Increases Levels of CDP-Choline in the Brain and in a Neural Cell Line Materials and Experimental Methods Experimental Design Data was pooled from three experiments, with group sizes ranging from 5 to 16 animals. Male gerbils (60-80 g) were given UMP (1 mmole/kg body weight) by gavage and sacrificed at the indicated times. After brain homogenization, protein precipitation, and lyophilization as described for Example 3, samples were analyzed by HPLC-UV.

Assessment of CDP-Choline Levels

Brain tissue or cells was dissolved in methanol/chloroform (1:2 vol/vol), centrifuged, and the aqueous phase was dried under vacuum, resuspended in 100-200 μL water and separated by HPLC on an ion-exchange column (Alltech Hypersil APS-2, 5 μM, 250×4.6 mm). CDP-choline was eluted with a linear gradient of $NaH_2PO_4$ buffers A (1.75 mM $NaH_2PO_4$, pH 2.9) and B (500 mM, pH 4.5), which allowed resolution of CDP-choline from closely co-eluting substances such as UMP over 40 min. The retention time for CDP-choline was 9.5 min. Individual nucleotide peaks were detected by UV absorption at 380 nm, and were identified by comparison with the positions of authentic standards, as well as by the addition of nucleotide standards to selected samples.

PC12 Cells

PC12 cells were maintained in Minimal Essential Medium (MEM; Invitrogen, Carlsbad, Calif.) supplemented with 10% fetal bovine serum (FBS) at 37° C. Experimental incubations were for 2 or 4 days in medium containing 50 ng/ml mouse 2.5 S (2.5 subunit) NGF and 1% FBS, with or without test compounds. NGF and FBS were obtained from Invitrogen.

Results

In order to assess the effect of orally administered uridine on levels of phospholipid precursors in the brain, brains of the gerbils from the second experiment of Example 3 were assayed for levels of CDP-choline, a key intermediate in phospholipid biosynthesis via the Kennedy pathway Levels of CDP-choline rose significantly in a linear fashion (regression analysis, r=0.98, p<0.02) for 30 min after administration of UMP (FIG. 8).

To directly demonstrate conversion of uridine to CDP-choline in neural cells, PC 12 cells, a cell line capable of differentiation into neural cells, were treated with uridine, and intracellular levels of CDP-choline were measured. Uridine treatment resulted in a statistically significant increase in CDP-choline levels after 50 minutes (FIG. 9). These results show that, after transport to the brain, uridine is converted to phospholipid precursors such as CDP-choline, perhaps via the intermediate CTP, and therefore augments cognitive function and intelligence by increasing synthesis of phospholipid precursors in brain cells.

Example 6

Oral Administration OF UMP Increases Neurotransmitter Release in Brains of Aged Rats Materials and Experimental Methods Animals and Dietary UMP Supplementation Male middle aged Fischer 344 rats, 22-24 months old at the time of doing microdialysis, were obtained from National Institute on Aging (Harlan Sprague-Dawley, Indianapolis, Ind.). Rats were housed individually under standard husbandry conditions and exposed to 12 hr light/dark cycle with food and water provided ad libitum. Each rat consumed approximately 500 mg/kg/day of UMP·2Na ($LD_{50}$ by i.p. of uridine is about 4.3 g/Kg).

Rats were acclimated to the animal facility for more than 7 days before fed a control laboratory diet (Teklad Global 16% protein rodent diet, TD.00217, Harlan Telclad, Madison, Wis.), or this diet fortified with UMP·2Na$^+$ (2.5%, TD.03398, UMP·2Na$^+$; Numico Research, the Netherlands) for 6 weeks.

Rats were not fed with the research diet until at least 7 days later after their arrival. They were weighed at the time of beginning feeding (t=0), as well as 1, 2, 4, 6 weeks later. At time 0, rats were randomly assigned into two groups. There were no significant differences of body weight between groups ($F_{1,11}$=3.03, p>0.05); average weight was 455±5 (N=13 rats). Repeated measures with weeks as within-subjects factor showed feeding time (0, 1, 2, 4, 6 weeks) significantly changed body weight ($F_{4,44}$=2.65, p<0.05), while neither UMP-diet (vs. control) nor UMP time interaction affected body weight ($F_{1,11}$=0.01, $F_{4,44}$=1.25, respectively; all p>0.05).

The experiment described in this Example was performed twice, each time with 7 control rats and 9 rats administered the UMP diet. Results were consistent between the two experiments.

Chemicals and Solutions

Dopamine (DA), dihydroxyphenylacetic acid (DOPAC), homovanillic acid (HVA), serotonin (5-HT), 5-hydroxyindoleacetic acid (5-HIAA), and 3,4-dihydroxybenzoic acid (DHBA; internal standard) were purchased from Sigma (St. Louis, Mo.) and were dissolved in $HClO_4$ (0.1 M) to make 1 mM stock solutions, and aliquots were kept at −80° C. Ketamine hydrochloride (100 mg/ml) was purchased from Fort Dodge Animal Health (Fort Dorge, Iowa). Xylazine (20 mg/ml) originated from Phoenix Scientific, Inc. (St. Joseph, Mo.).

Ringer solution consisted of NaCl 147, KCl 2.7, $CaCl_2$ 1.2 and $MgCl_2$ 0.85 mM. For high potassium solution, KCl was increased to 80 mM, with NaCl decreased to 69.7 mM to maintain osmolarity. All solutions were made from doubly distilled deionized water and filtered by Steriflip® (Millipore. Bedford, Mass.).

In Vivo Microdialysis

Rats were anesthetized with a mixture of ketamine and xylazine (80 and 10 mg/Kg of body weight, respectively, intraperitoneally), and were placed in a Kopf stereotaxic frame. All surgical instruments were sterilized by a hot bead dry sterilizer or 70% ethanol. A small hole was drilled into the skull by a 2-mm trephine bone drill. CMA/11 14/04 Cupr probe (O.D. 0.24 mm, 4 mm membrane, 6,000 Da, CMA microdialysis, Sweden) was implanted into the right striatum (AP=+0.5, ML=−3.0 from Bregma, DV=−7.3 mm from Dura, as described in Paxinos G et al, The Rat Brain in Stereotaxic Coordinates, 2$^{nd}$ ed., Academic Press, San Diego) with incisor bar set at −5.0 mm. Probes were secured permanently in position using dental cement and three anchor screws to the skull. After surgery, rats were injected intraperitoneally with saline (5 ml/kg) and kept on a heating pad maintaining body temperature at 37° C. until awaking.

The freely moving rat was perfused in a circular bowl on a rotating platform obviating the need for a liquid swivel (see Wang L et al, Neurochem Int 42: 465-70, 2003), and was habituated to the environment on the first day after surgery. Experiments were performed approximately 48 hr after the surgery, and were carried out between 10:00 am to 4:00 pm. Ringer's solution was perfused continuously using Fluorinatedethylenepropylene (FEP) Resin tubing and a gas-tight syringe (Exmire type I, CMA), at a constant rate of 1.5 μl/min by a microinfusion pump (CMA/100). Dialysates were collected at 15-min intervals. 5 μl of antioxidant mixture, consisting of 0.2 M $HClO_4$ and 0.1 mM EDTA, was added to the sampling vial prior to collection to protect dopamine and its metabolites. The samples within the first 60 min were discarded from analysis. Subsequently, 3 consecutive sessions of samples were collected Except for the last session (1.5 hrs, 6 samples), the others were collected for 1 hr (4 samples). The order was as follows: session 1 (aCSF), 2 (High K$^+$), 3 (aCSF). All samples were collected on crushed ice, instantly frozen and kept at −80° C. until HPLC analysis Brain Dissection For The Proteins and Monoamines After microdialysis experiments, rats were anesthetized with ketamine and xylazine (80 and 10 mg/Kg, i.p.). A black ink was pushed through the probe to stain the tissue around the probe. Rats were decapitated with a guillotine. Brains were quickly dissected on a chilled dissection board. The left striatum was snap-frozen in an Eppendorf tube placed in liquid nitrogen for future protein assays. The right striatum was further dissected, and the position of probe was determined by visual observation Data were not included if probe was found not within the striatum.

An additional group of rats (20 months old; n=6 for both control and UMP) were fed for 6 weeks. No microdialysis was carried out in these rats. Striata (both left and right) were collected as above to determine tissue levels of dopamine and its metabolites.

Extraction of Tissue Dopamine Samples

The striatum were weighed and homogenized in an Eppendorf tube on ice for 1 min with 1 ml of $H_2O$ containing 0.1 M $HClO_4$ and 1 μM EDTA. After vortexing for 10 seconds, an aliquot was used for Bicinchoninic Acid (Sigma, St. Louis, Mo.) protein assay. The homogenates were then filtered with Ultrafree-MC centrifugal filter units (Millipore, 14,000 rpm/5 min/4° C.). A 1: 10 dilution was made before the aqueous layer was subjected to HPLC. DHBA was added to the samples prior to homogenization as the internal standard Concentrations of dopamine and its metabolites were determined by HPLC, and values from the three repeated measures were averaged and normalized to the amount of protein per sample.

Analysis of Dopamine and Metabolites

DA and metabolites in dialysates and tissue samples were determined using an ESA Coulochem 11 5100A detector ($E_1$=−175 mV; $E_2$=+325 mV; $E_{guard}$=350 mV) with an ESA Microdialysis Cell (model 5014B, ESA, North Chelmsford, Mass.). The mobile phase (MD-TM, ESA) consisted of 75 mM $NaH_2PO_4$, 1.7 mM 1-octanesulfonic acid, 100 μl/L Triethylamine, 25 μM EDTA, 10% acetonitrile, pH 3.0. The flow rate was 0.4 mL/min The column (ESA MD 150, 3×150 mm, 3 μm, 120 Å) was kept in a 40° C. column oven. Samples were injected to HPLC by an Alltech 580 autosampler (Alltech, Deerfield, Ill.) and maintained to 4° C. with a cooling tray during analysis. Data were captured by Alltech AllChrom™ data system, and analyzed with AllChrom Plus™ software. A timeline program, which could change the detection gain during sample separation and detection, was used to make it possible to get low DA and high metabolites concentration data in dialysate through one injection.

Data Analysis

Data were represented according to sampling time of six to nine measurements each point (means±standard error of measurement [S.E.M.]). Basal values of DA and major metabolites were determined based on the averages of the first four consecutive samples prior to K$^+$ stimulation (mean value in the dialysate was 10.2±0.4 nM, n=22), which was assigned a value of 100%. Statistics were performed using two-way ANOVA (Treatment×time) with Turkey's HSD post hoc test. One-way ANOVA was used to compare the differences among the three groups in each time point. A p value of >0.05 was used to assess statistical significance. Basal levels of dopamine were homogeneous between the two replicated experiments and were therefore pooled into the corresponding groups ($F_{1,20}$=3.99, p>0.05). Basal DA levels in the dialysates were stable after 1 hr equilibration, in the four consecutive samples prior to K$^+$ stimulation ($F_{3,57}$=0.05, p>0.05; one-way ANOVA with repeated measures using sampling time (0, 15, 30, 45 min) as within-subjects factor).

Similar to basal DA levels, basal levels of DOPAC and HVA in the dialysates were 612±14 and 369±7 nM (n=22 rats), and were stable ($F_{3,57}$=1.06, $F_{3,57}$=0.84, respectively; in each case, p>0.05). There were no effects of UMP treatment on the basal DOPAC and HVA levels (Control vs. UMP-1 week vs. UMP-6 weeks; $F_{2,19}$=0.27, $F_{2,19}$=0.03, respectively; in each case, p>0.05).

Results

In order to assess the effect of orally administered uridine metabolites on neurotransmitter release in the brain, aged rats maintained in a restricted environment consumed for 1 or 6 weeks either a control diet or a diet supplemented with 2.5% UMP. UMP supplementation did not affect basal DA levels in the dialysate among treatment groups (control vs. UMP-1 week vs. UMP-6 weeks; $F_{2,19}$=0.98). DA concentration in the dialysate was 10.2±0.4 nM (n22 rats).

Figure 12A:
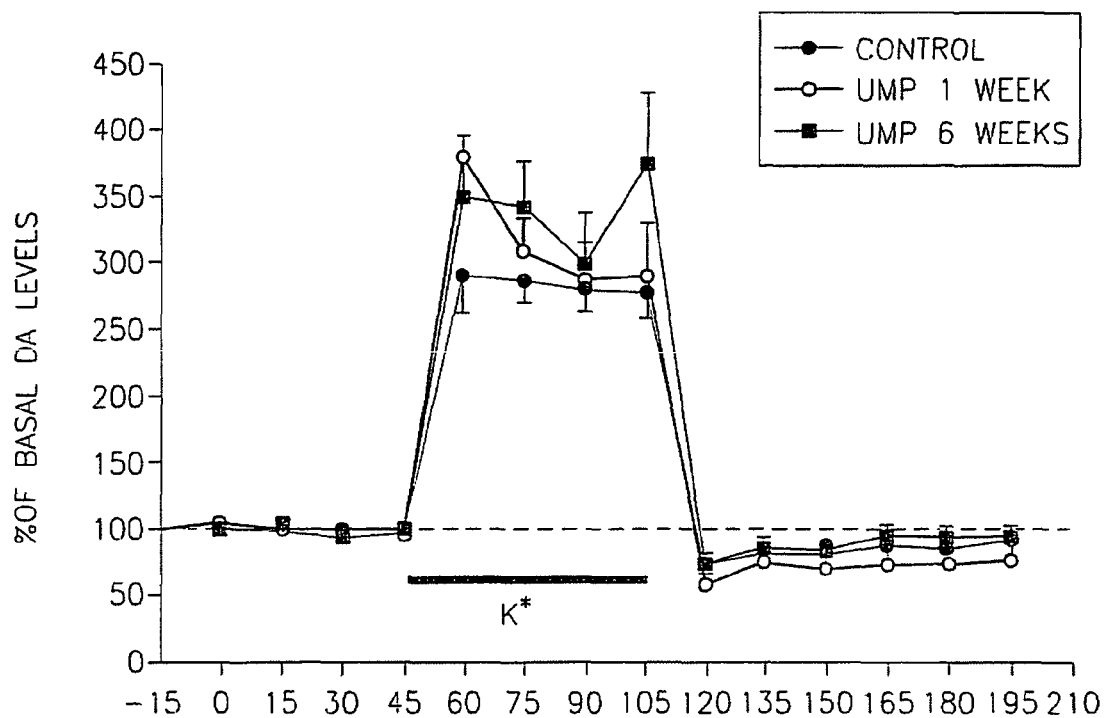
FIG. 12. Effect of UMP dietary supplementation on neurofilament protein levels in contralateral striatum. (A): NF-70. (B): NF-M *: $p<0.05$, **: $p<0.01$ compared to corresponding controls.
Figure 12B:
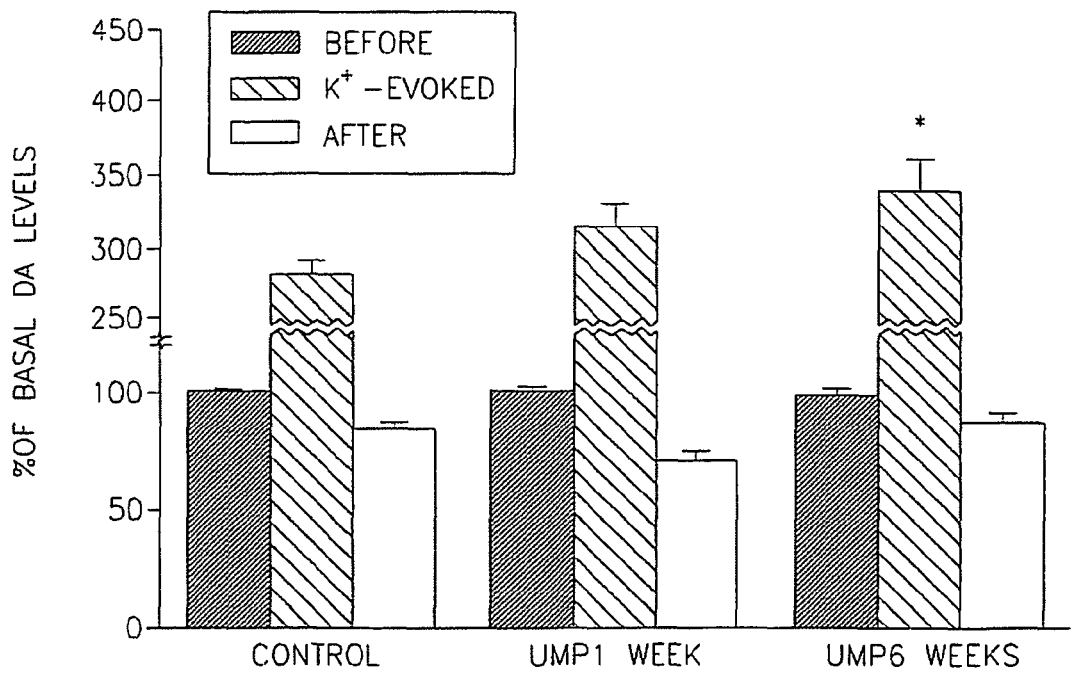
Figure 13A:
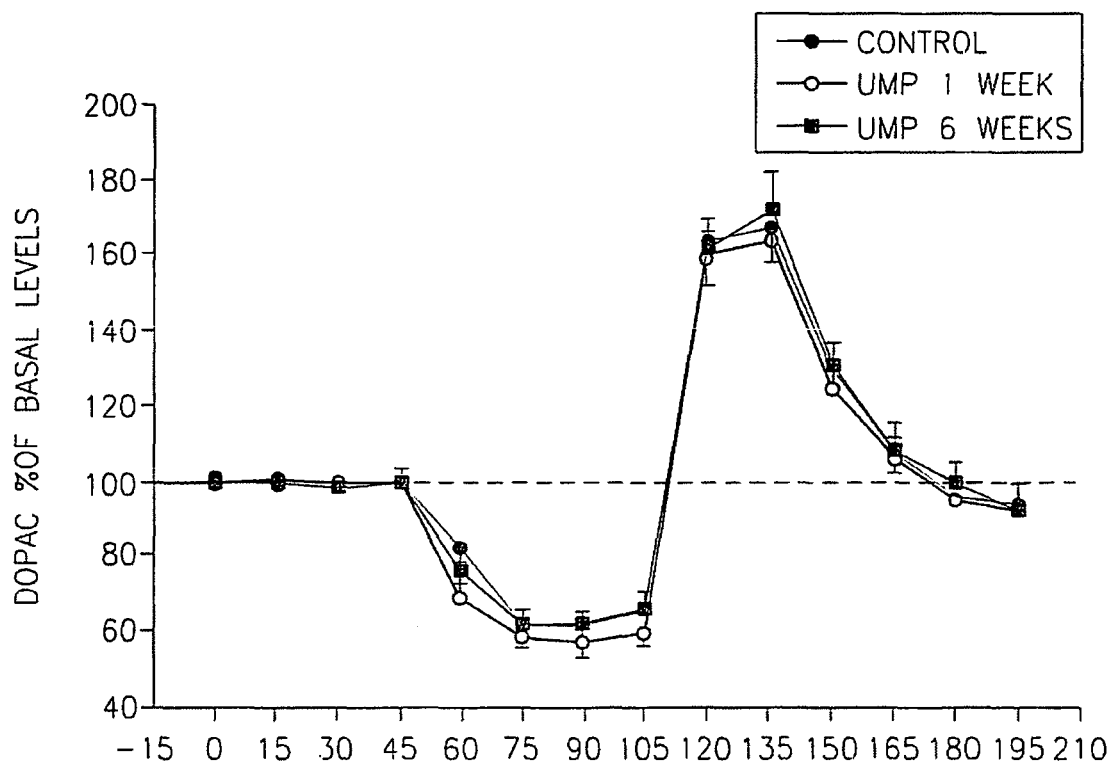
FIG. 13. Uridine treatment enhances neurite outgrowth. A. PC 12 cells treated for 4 days with NGF (50 ng/ml) in the presence or absence of uridine (50 μM). B. Number of neurites per cell after 2 or 4 days of treatment. C. Number of neurites per cell after 2 or 4 days of NGF plus different concentrations of uridine (50, 100 and 200 μM). D. Quantification of the number of branch points for each cell. E. Levels of the structural proteins NF-70 and NF-M, as determined using Western blotting N=NGF, U=Uridine. Values represent means+SEM. : $p<0.01$, *: $p<0.001$ vs. NGF treatment.
Figure 13B:
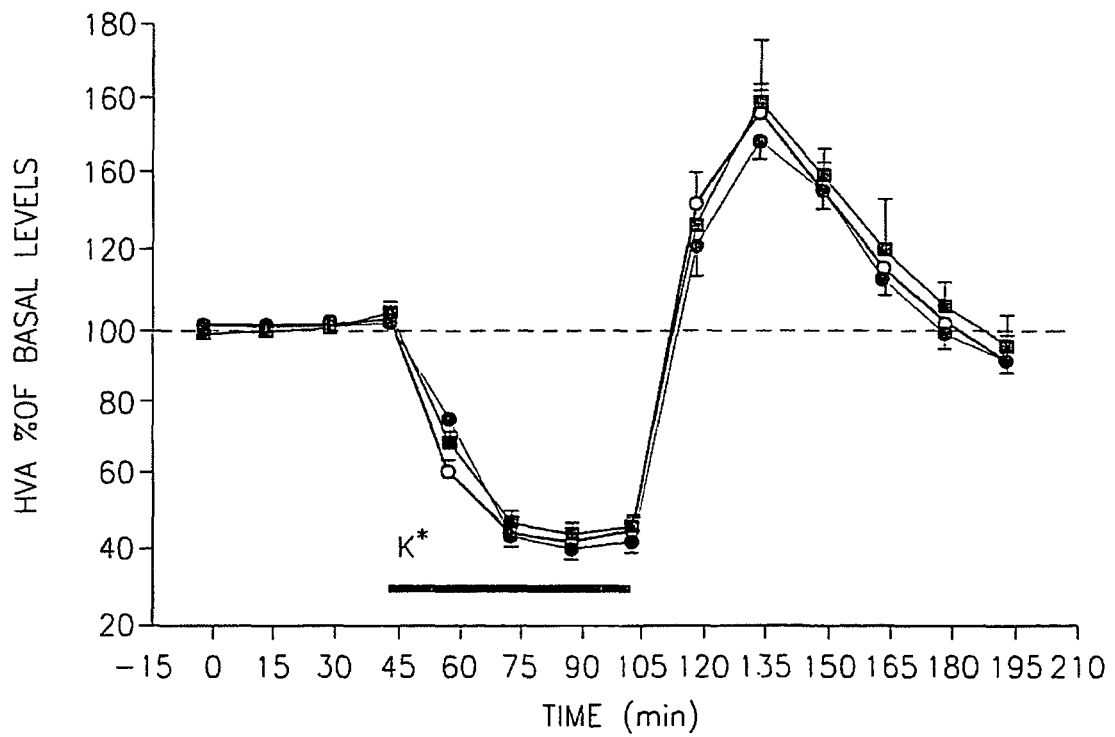
Figure 14:
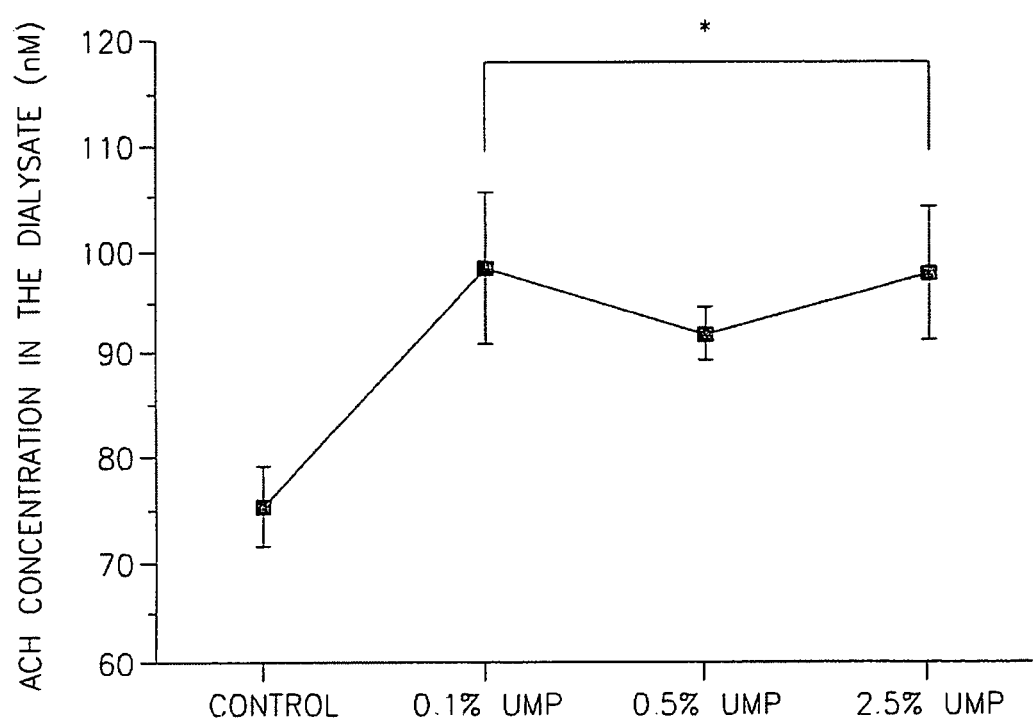
FIG. 14. Uridine treatment increases intracellular levels of UTP and CTP in cells treated with NGF. Uridine treatment (50 μM) significantly increased intracellular UTP levels (A) and intracellular CTP levels (B). N=NGF, U=Uridine, C=Cytidine. Values represent means+SEM. *: $p<0.05$ vs. NGF treatment.

The effect of dietary UMP supplementation on K$^+$-evoked striatal DA release (following perfusion with the high-K+ solution) is depicted in FIG. 12A. A statistically significant difference ($F_{2,266}$=3.36) was found in DA levels in the dialysates among the control, UMP-1 week, and UMP-6 weeks treatment groups. Post hoc multiple comparisons revealed a significant difference between control and UMP-6 weeks' groups. Data were further divided into three sections (before, K$^+$-evoked and after), which also revealed a significant enhancement of K$^+$-evoked DA release between control and UMP-6 weeks' groups, from 283±9% to 341±21% (FIG. 12B). The UMP-1 week group also exhibited increased DA release (316±15%) relative to the control group; however, this increase was not significant.

Figure 11:
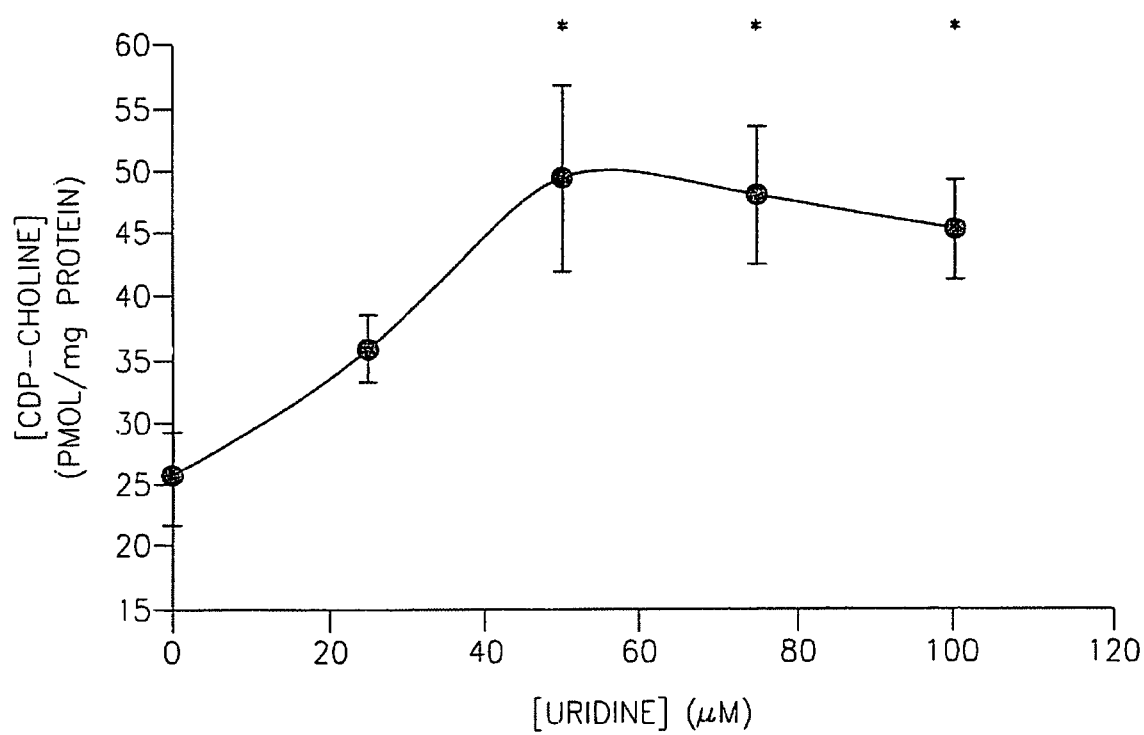
FIG. 11. Increased acetylcholine basal concentration with UMP treatment. Depicted are means+/−SEM. "*" denotes p value of >0.05.

In addition, dietary UMP was shown to increase the basal release of the neurotransmitter acetylcholine from neurons in the corpus striatum (FIG. 11).

These results show that (a) orally administered uridine improves neurotransmitter release in the brain; (b) uridine-mediated augmentation of brain function is a multi-species phenomenon, not limited to gerbils; and (c) augmentation of brain function by uridine occurs in a biologically relevant animal model for age-impaired cognitive dysfunction.

Example 7

UTP Administration Increases Levels of NF-70 and NF-M in Brains of Ages Rats

Materials and Experimental Methods

Data Analysis

Data were represented according to UMP treatment of six to sixteen measurements each group (means±S.E.M.). One-way ANOVA with Turkey's HSD post hoc tests were used to compare the difference among the treatments the Newman-Keuls multiple range test was used for the data in FIG. 13.

Western Blotting

Striatal tissues were placed in Eppendorf tubes containing 200 µl lysis buffer (60 mM Tris-HCl, 4% SDS, 20% glycerol, 1 mM dithiothreitol, 1 mM AEBSF, 8 µM aprotinin, 500 µM bestatin, 15 µM E64, 200 µM leupeptin, 10 µM pepstatin A). The samples were sonicated, boiled (10 min), and centrifuged (14,000 g for 1 min at room temperature) The supernatant fluid was transferred to a clean tube, and total protein content was determined using the Bicinchoninic Acid assay (Sigma, St. Louis, Mo.).

Equal amounts of protein (40 µg protein/lane) were loaded for sodium dodecyl sulfate-polyacrylamide gel electrophoresis (4-15% SDS PAGE; Bio-Rad, Hercules, Calif.). Prior to gel electrophoresis, bromphenol blue solution (0.07%) was added to each sample. Proteins were separated, transferred onto polyvinylidene difluoride (PVDF) membranes (Immobilon-P, Millipore), and blocked with 5% bovine serum albumin (Tris-buffered saline/0.15% Tween 20) for 1 h. After 3 10 min rinses in Tris-buffered saline (TBST), blots were incubated in TBST with various antibodies against the proteins of interest, including NF-70, NF-M (1: 2000, 1: 5000, respectively; Calbiochem, La Jolla, Calif.) at 4° C. overnight on an orbital shaker. Protein-antibody complexes were detected and visualized using the ECL system (Amersham, Piscataway, N.J.) and Kodak X-AR film, respectively, as suggested by the manufacturer. Films were digitized using a Supervista S-12 scanner with a transparency adapter (UMAX Technologies, Freemont, Calif.). Analysis was performed using the public domain NIH Image program (NIH V.1.61).

Results

In order to assess whether increasing uridine levels can augment the production of new membrane in the brain, levels of neurofilament-70 (NF-70) and neurofilament-M (NF-M), biomarkers of neurite outgrowth, were assessed in the brains of the rats from the experiment described in Example 6 UMP dietary supplementation for 6 weeks significantly increased the levels of NF-70 (FIG. 12A) and NF-M (FIG. 12B), to 182±25% (F2,31=6.01, p<0.05) and 221±34% (F2,21=8.86, p<0.01) of control values, respectively. Consumption of a UMP diet for 1 week did not increase the levels of these two proteins compared to control group in a statistically significant manner. Levels of NF-70 and NF-M in striatum increased to 204±36% and 221±34% of control values, respectively.

Example 8

Uridine or UTP Administration Increases Neurite Outgrowth, Branching, and NF-70 and NF-M Levels in Neurite Cells Materials and Experimental Methods Data Analysis Data are presented as mean±S.E.M. Analysis of variance (ANOVA) was used to determine differences between groups (significance level, p<0.05). When differences were detected, means were separated using the Newman-Keuls multiple range test.

Neurite Outgrowth Studies

PC12 cells were sparsely plated on collagen-coated 60 mm culture dishes in MEM containing 1% fetal bovine serum. Experimental groups were as follows: uridine, uridine triphospate, cytidine, reactive blue 2, suramin and PPADS (Sigma, St. Louis, Mo.). All treatments were performed 24 h after plating. At the end of the treatment period, images were obtained with a phase-contrast Zeiss Axioplan 2 microscope, using OpenLab software. Six digital images were captured for each dish, for a total of 18 to 24 images per treatment group Approximately 300 cells were quantified for each treatment group for each experiment. Experiments were performed in triplicate. Quantification of neurites, including neurite branching and neurite length, was performed by one more researchers blinded to experimental groups Neurite length was measured using the public domain NIH software "Image J." Processes longer than the diameter of the cell body were counted as neurites. Only process-bearing cells were analyzed.

Detection of Intracellular UTP and CTP

Levels of intracellular UTP and CTP were analyzed by HPLC as described for Example 5, except that 5 mM $NaH_2PO_4$, pH 2.65 was used as buffer A.

Results

The effect of uridine treatment (10-200 µM) on NGF-induced neurite outgrowth was next tested. In the absence of NGF, PC12 cells did not sprout neurites (fewer than 1%). Uridine treatment (50 µM, 2 or 4 days) in the absence of NGF did not result in the production of neurites. In the presence of NGF, uridine (50-200 µM) significantly (p<0.01 or 0.001) enhanced the number of neurites per cell after 4 days of treatment (FIG. 13A-C), whereas 2-day treatment or lower uridine concentrations (10, 25 µM) had no effect. Treatment of the NGF-exposed cells with cytidine also had no effect on neurite outgrowth.

Since uridine increased the number of neurites per cell, the effect of uridine on neurite branching and length in the presence of NGF was also assessed. After 4 days of treatment with uridine (50 µM) and NGF, the numbers of neurite branch points per cell were significantly (p<0.01) increased, compared with those in cells treated with only NGF (FIG. 13D). Uridine did not significantly affect average neurite length in NGF-differentiated cells.

Neurofilament proteins are highly enriched within neurites; therefore, an increase in neurite number should be associated with increased expression of neurofilament proteins. NF-70 (70 kD) and NF-M (145 kD) levels following 4-day treatment of PC 12 cells with NGF alone, or NGF plus uridine (50 µM) were thus measured (FIG. 13E). Both NF-70 and NF-M expression significantly (p<0.01, p<0.001, respectively) increased following uridine treatment, compared to cells treated only with NGF. In the absence of NGF, uridine treatment had no effect on levels of either neurofilament protein. Thus, uridine augments neurite outgrowth in PC 12 cells.

In the absence of NGF, the addition of exogenous uridine increases intracellular UTP and CDP-choline levels in PC 12 cells (Example 5). To determine whether uridine affects UTP or CTP levels in the presence of NGF, levels of UTP and CTP were measured in PC 12 cells for 2 days with NGF, treated with no nucleotide, (control), uridine, cytidine or UTP, in the presence of NGF. Uridine (50 µM) significantly (p<0.05) increased both UTP and CTP levels (FIG. 14 A-B, respectively) compared to cells receiving only NGF treatment. UTP (100 µM) or cytidine (50 µM) did not significantly affect the intracellular levels of either nucleotide.

Figure 15A:
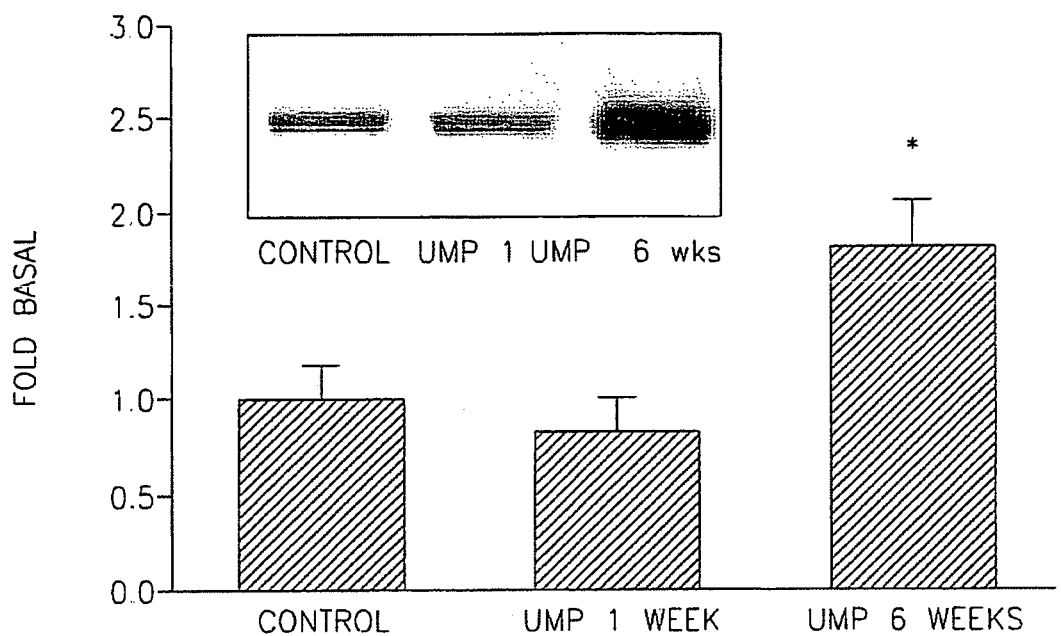
FIG. 15. UTP treatment increases neurite outgrowth. Treatment of PC 12 cells for 4 days with NGF and UTP significantly enhanced the number of neurites produced per cell, compared to treatment with NGF alone. Values represent means+SEM. **$p<0.01$.
Figure 15B:
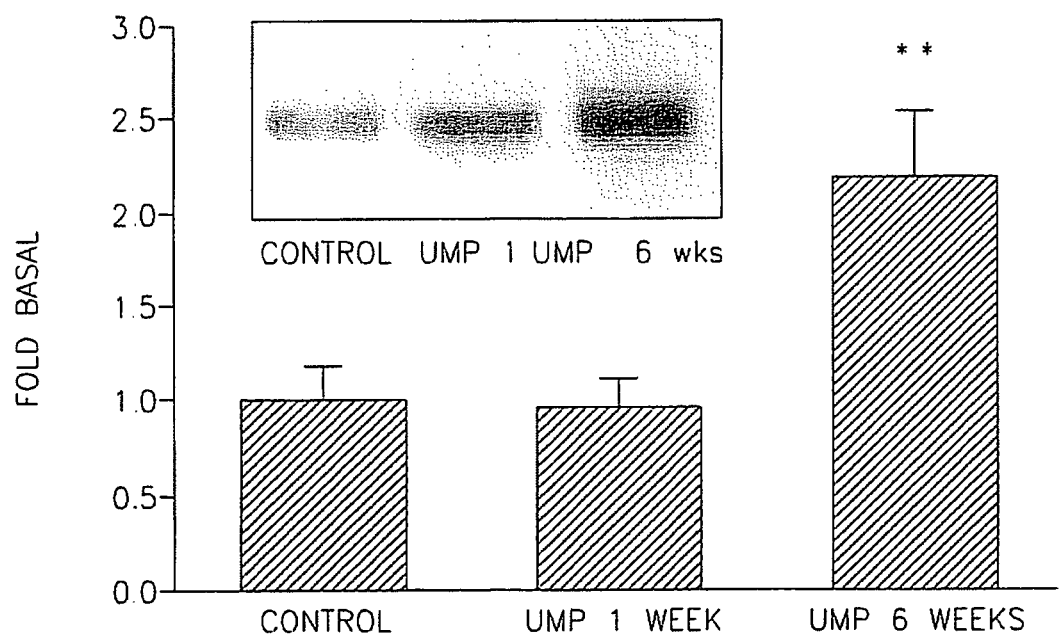

In order to ascertain whether UTP may mediate the effect of uridine on neurite outgrowth, PC12 cells were treated with NGF and various doses of UTP. After 4 days of treatment, UTP (10 and 50 µM) significantly (p<0.01) enhanced neurite outgrowth, compared to that in cells treated only with NGF (FIG. 15). Thus, either uridine or UTP augments neurite outgrowth.

In conclusion, uridine or UTP dietary supplementation increased the levels of two major neurofilament proteins in rat brain, and was directly shown to induce neurite outgrowth in PC 12 cells.

Example 9

NGF-Differentiated PC 12 Cells Express Pyrimidine-Sensitive P2Y2, P2Y4 and P2Y6 Receptors Materials and Experimental Methods Detection of P2Y Receptors Western blots utilized rabbit anti-P2Y2, anti-P2Y4 (both from Calbiochem); or rabbit anti-P2Y6 (Novus Biologicals, Littleton, Colo.).

Immunocytochemistry

PC 12 cells were treated as described above, except they were grown on 12 mm glass cover slips (A Daigger & Co., Vernon Hills, Ill.) coated with collagen. Proteins were visualized using immunofluorescence. Briefly, the cells were fixed with 4% paraformaldehyde, permeabilized with 0.25% Triton X-100, blocked in 10% normal goat serum, and incubated overnight in the appropriate antibodies (mouse anti-NF-70, and either rabbit anti-P2Y2, rabbit anti-P2Y4 or rabbit anti-P2Y6). For P2Y2 and P2Y4 visualization, control cultures were incubated with primary antibody plus a control antigen in order to ensure that the immuno-staining would be specific. Control antigen was not available for the P2Y6 receptor. Cells were then incubated in fluorochrome-conjugated secondary antibodies for 1 hour (goat anti-rabbit ALEXA 488 and goat anti-mouse ALEXA 568; Molecular Probes, Eugene, Oreg.) and mounted on glass slides with mounting media with or without DAPI (Vector Laboratories, Burlingame, Calif.). Control antigens provided with the primary antibodies were used to ensure that immuno-staining was specific. Digital images were obtained on a Zeiss (Oberkochen, Germany) Axioplan microscope with OpenLab software, using a Zeiss Plan-Neofluor 40x oil-immersion objective.

Results

Figure 16A:
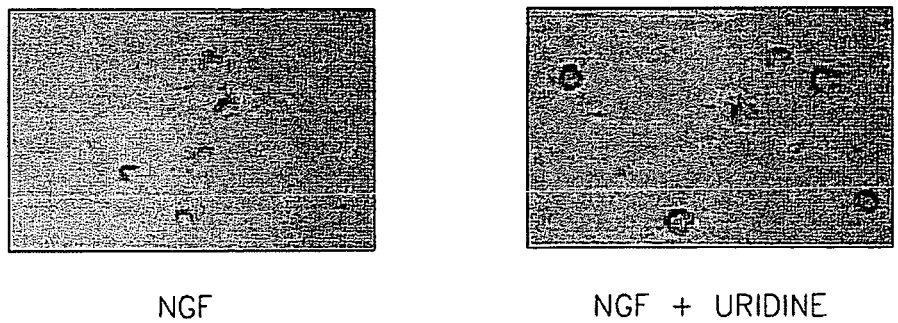
FIG. 16. NGF-differentiated cells express pyrimidine-sensitive P2Y receptors. A. Levels of P2Y2, P2Y4 and P2Y6 receptor expression after incubation of cells with NGF for varying lengths of time. B. Following 4 days of NGF treatment, cells were fixed and NF-70 (red) and P2Y receptor (green) proteins were visualized using immunofluorescence. Left panel: P2Y2. Middle panel: P2Y4. Right panel: P2Y6. Values represent means+SEM. *** $p<0.001$.
Figure 16B:
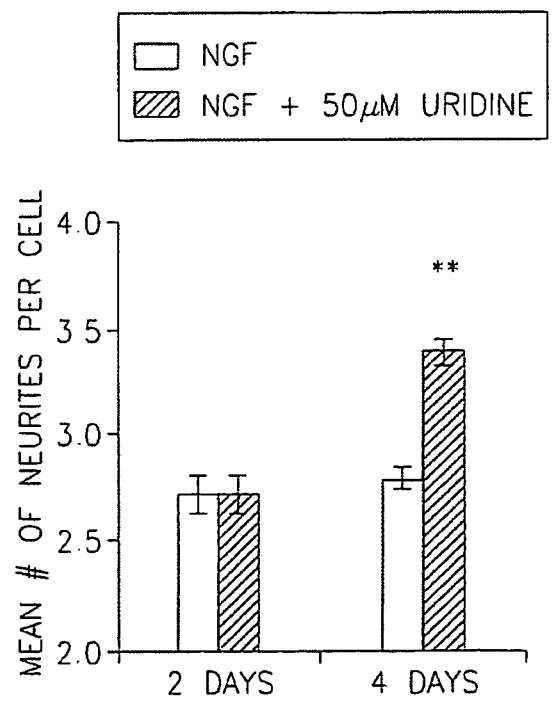
Figure 16C:
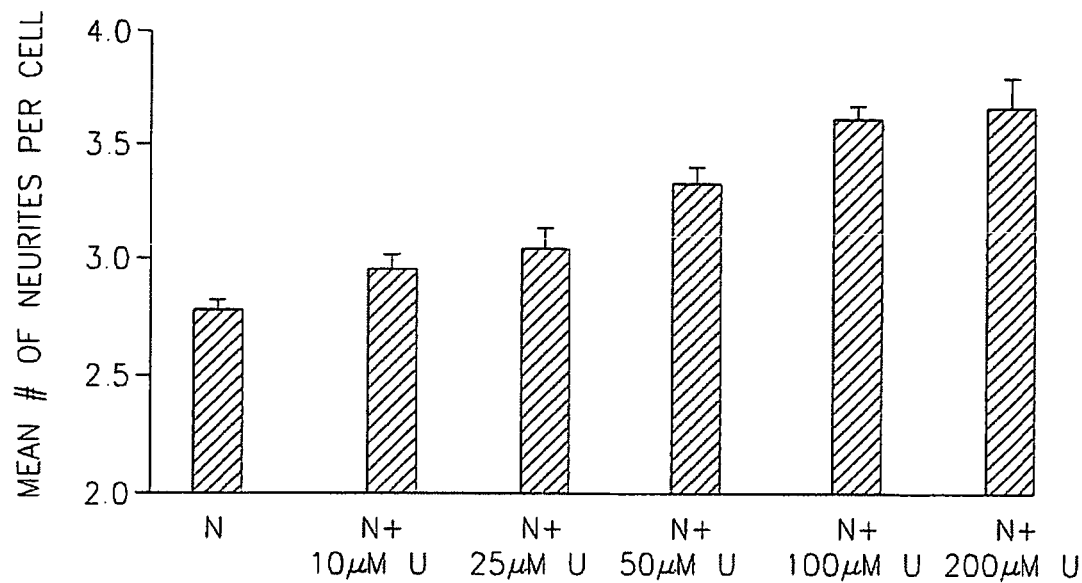
Figure 16D:
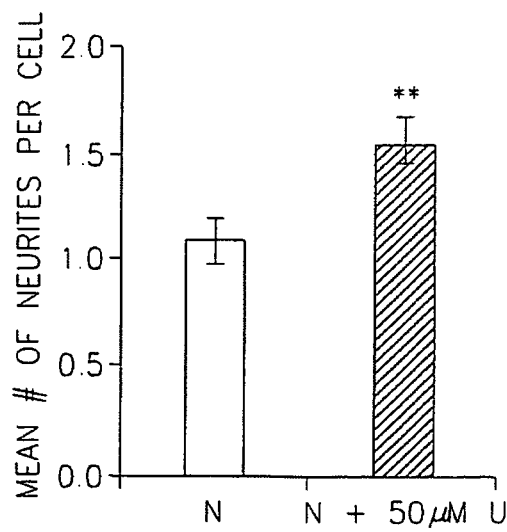

UTP is an agonist of the pyrimidine-activated class of P2Y receptors, namely P2Y2, P2Y4 and P2Y6 receptors. To determine whether these receptors participate in the mechanism by which extracellular UTP affects neurite outgrowth, it was first determined whether the receptors are expressed in PC12 cells, and whether exposure to NGF alters their expression, PC 12 cells were treated for 0-7 days with NGF and levels of the receptors measured. After 3 days of NGF treatment, expression of the P2Y2 receptor reached maximal levels, which were significantly ($p<0.001$) higher than those seen at less than 3 days of NGF treatment (FIG. 16A). To visualize the expression and localization of the P2Y2, as well as the P2Y4 and P2Y6, receptors, cells were grown in the presence or absence of NGF for 4 days and then immuno-stained them for the neuritic marker NF-70, and for P2Y2, P2Y4, or P2Y6 (FIG. 16B, left to right, respectively). All three receptors were highly expressed in NGF-differentiated PC12 cells. In addition, P2Y2 co-localized with the neuronal marker MAP-2. In the absence of NGF, receptor protein expression was undetectable by immuno-staining. Moreover, the presence of uridine did not affect the expression of the receptors compared with the quantities present in cells exposed to NGF alone. Thus, the P2Y2, P2Y4 and P2Y6 receptors are present in neural cells, but not in their precursors.

Example 10

Antagonism of P2Y Receptors Inhibits the Effect of Uridine on NGF-Induced Neurite Outgrowth To ascertain whether signaling by P2Y receptors mediate induction of neurite outgrowth by uridine, PC 12 cells were incubated for 4 days with NGF, uridine (100 µM) and the P2Y receptor antagonists suramin (30 µM), pyridoxal-phosphate-6-azophenyl-2',4' disulfonic acid (PPADS; 30 µM) and reactive blue 2 (RB-2; 10 µM). Each of the antagonists significantly ($p<0.05$ or $0.001$) blocked uridine enhancement of NGF-stimulated neurite outgrowth (FIG. 17) None of the P2Y receptor antagonists inhibited the uptake of uridine into the PC12 cells These results show that signaling via P2Y receptors mediates uridine induction of neurite outgrowth.

Example 11

Phosphatidylinositol (IP) Signaling is Stimulated by UTP and Uridine

Materials and Experimental Methods

Metabolic Labeling and PI Turnover Analysis
Analysis of PI turnover was performed as described by (Nitsch R M et al, J Neurochem 69: 704-12, 1997). Briefly, cells were labeled metabolically for 36 h with 1.25 microCurie (µCi)/dish of myo-[2-$^3$H]inositol (17.0 Curie/mmol; Amersham Biosciences) in serum-free MEM, washed twice with Hank's balanced salt solution (HBSS), and treated for 15 min with 10 mM lithium chloride in HBSS. Drugs were added in the presence of 10 mM lithium for 60 min at 37° C. Cells were lysed with ice-cold methanol, and lipids were removed by extraction with chloroform/methanol/water (2:2:1 by volume). Labeled water-soluble inositol phosphates were separated from free [$^3$H]inositol by ion-exchange chromatography, using AG 1-X8 columns (Bio-Rad), and 1M ammonium formate and 0.1M formic acid as eluent. Radioactivity was quantified by liquid scintillation spectrometry.

Results

P2Y2, P2Y4 and P2Y6 receptors activate the phospholipase C/diacylglycerollinositol triphosphate (PLC/DAG/IP3) signaling pathway. To determine whether concentrations of uridine or UTP that promote neurite outgrowth activate these receptors, NGF-differentiated PC 12 cells were labeled with [$^3$H]-inositol (50 µM) or UTP (10, 100 µM) for 1 hour, and IP signaling was assessed by measuring turnover of radio-labeled IP (FIG. 18). Formation of IP was significantly increased by addition of 100 µM UTP ($p<0.05$) and by 50 µM uridine ($p<0.01$). The P2Y receptor antagonist PPADS (100 µM) significantly ($p<0.05$) blocked the stimulation of IP signaling by UTP. These findings indicate that UTP promotes neurite outgrowth via P2Y receptors-mediated stimulation of the IP signaling pathway.

The findings of Examples 9-11 provide a mechanism by which uridine and its metabolites stimulate neurite outgrowth: namely, by activation of P2Y receptors. At least part of the action of the P2Y receptors is mediated by IP signaling. Overall, the findings from Examples 6-11 provide further evidence that uridine treatment can improve cognitive function and intelligence by enhancing neurotransmission by multiple mechanisms: (1) enhancing neurotransmitter release; (2) acting, through CTP, as a precursor for membrane phosphatides; (3) activating, through UTP, the P2Y receptor-coupled intracellular signaling pathway. In another embodiment, mechanism (2) and (3) act together to increase neurite formation.

Example 12

UMP-Supplemented Diets Enhance Learning and Memory in Multiple Species

Materials and Experimental Methods

Morris Water Maze
Aging rats (18 months, 500 g) were fed a control diet or a diet containing 2.5% UMP diets for six weeks. They were then shown a hidden platform in a six-foot diameter pool of water, placed somewhere in each of the four quadrants of the pool in turn, and were allowed 90 seconds in each trial to attempt to relocate the platform by swimming, and the swimming time "mean escape latency" recorded. The set of four trials was repeated on each of four consecutive days. The platform was in the same place each day. This test, known as the Morris water maze, is an indicator of spatial memory.
Food Pellet Learning Assay
Male young adult gerbils fed control or UMP-containing chow (0, 0.1, 0.5 or 2.5%) ad lib for three weeks were tested in a radial arm maze, consisting of a central chamber with four branches primed with a small food pellet at the end of each. Before testing, animals were fasted overnight; each animal was then placed in the central chamber and allowed up to 180 seconds to find all of the pellets. A shorter time required to find the pellets is indicative of improved learning and spatial memory.
Working Memory and Reference Memory Assay
Groups of ten gerbils fed control or 0.1% UMP diet for four weeks and trained to successfully find all of the food pellets as described above were then given a modified test in which only two arms of the maze (but always the same two) contained food pellet rewards. In this test, a working memory error is one in which a gerbil revisits an arm from which it has already taken the pellet that day. A reference memory error is one in which the gerbil enters an arm which never had food pellets (during the modified tests.)

Results

Previous Examples showed that orally administered uridine improves augments the ability of neural cells to function in several ways. The present Example directly shows that uridine augments cognitive function and intelligence. Aging rats (1 g months, 500 g) were fed a control diet or a diet containing 2.5% UMP·2Na+ for six weeks, and their memory was tested using the Morris water maze, an indicator of spatial memory. Rats administered the UMP·2Na+-fortified diet showed a statistically significant reduction in the time required to reach the location of the platform (FIG. 19), indicating that UMP enhances spatial memory.

Figure 20:
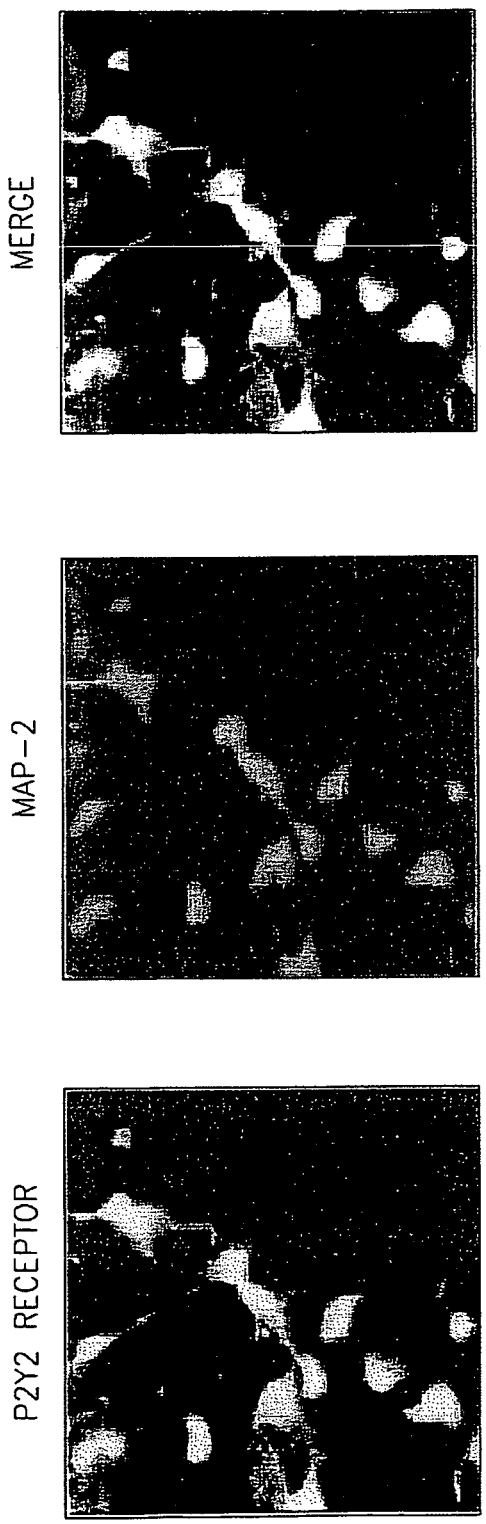
FIG. 20. Oral UMP improves learning and spatial memory in gerbils. Learning and spatial memory of gerbils fed a control diet or diets containing the indicated amount of UMP were tested in a radial arm maze. Results are depicted as the amount of time remaining before the 3-minute deadline.

The effect of orally administered uridine upon learning and spatial memory was also examined in gerbils. Male young adult gerbils fed control or UMP-containing chow (0, 0.1, 0.5 or 2.5%) ad lib for three weeks were tested in a radial arm maze, consisting of a central chamber with four branches primed with a small food pellet at the end of each. Before testing, animals were fasted overnight; each animal was then placed in the central chamber and allowed up to 180 seconds to find all of the pellets. The reduction in time needed to find the pellets requires spatial learning. UMP-supplemented diets reduced the time required for gerbils to find the pellet in a dose-dependent manner (FIG. 20).

Figure 21:
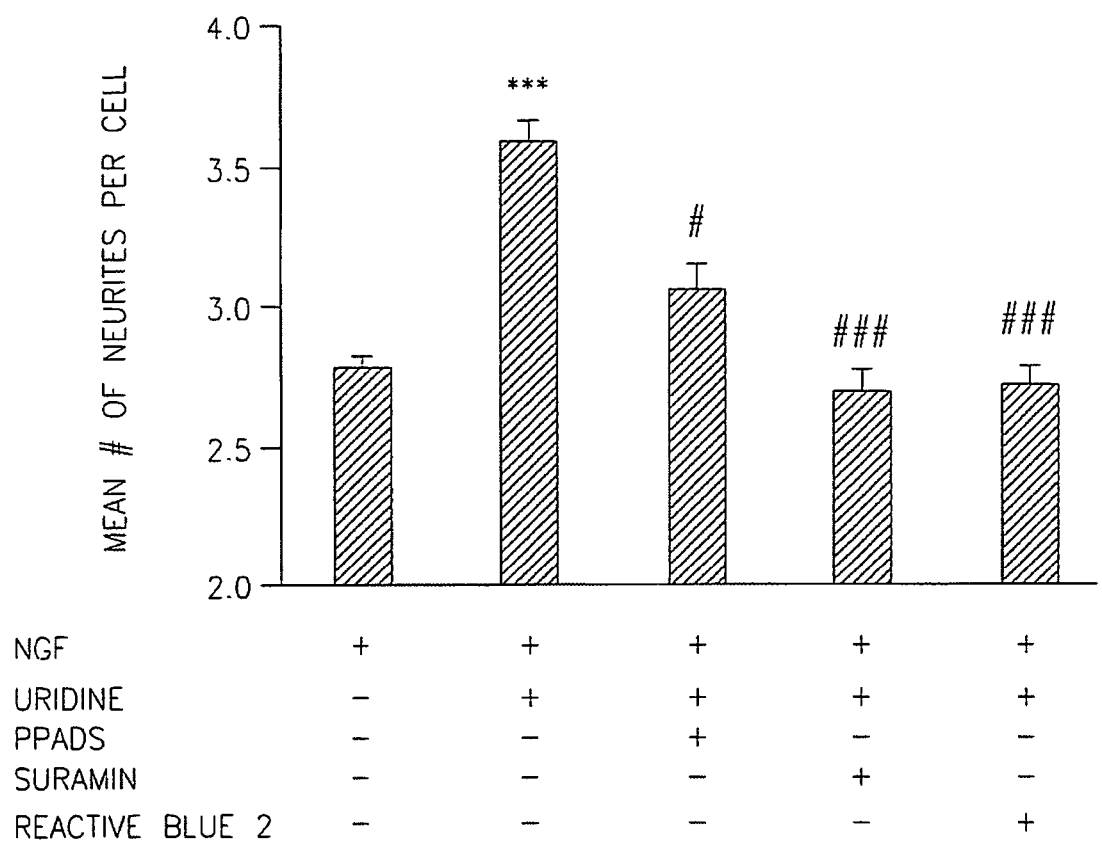
FIG. 21. Oral UMP improves working memory and reference memory. The memory of gerbils fed a control or a 0.1% UMP diet for four weeks was tested using modification of the test depicted in FIG. 20, which measured both working memory errors (A) and reference memory errors (B). Diamonds represent data points from control gerbils; triangles represent data points from gerbils fed 0.1% UMP diet.

In addition, the effect of orally administered uridine on working memory and reference memory was examined. Gerbils fed a control or a 0.1% UMP diet for four weeks and trained to successfully find all of the food pellets as described above were then given a modified test, that measures working memory and reference memory. Gerbils fed the UMP-supplemented diet exhibited reduced numbers of both working memory errors (FIG. 21A) and reference memory errors (FIG. 21B).

These findings directly show that (a) uridine dietary supplementation improves learning and various types (spatial, working, and reference) of memory; (b) the effect is not limited to a particular species; and (c) the effect is manifested in biologically relevant models of age-impaired cognitive function and intelligence.

In summary, the findings presented herein demonstrate that orally administered uridine positively affects neurological signaling, neural cell anatomy and cognitive memory or intelligence. The findings also implicate several mechanisms by which uridine exerts its effects.

Example 13

Uridine and Choline Increase Neurotransmitter Release

Materials and Experimental Methods

Brain Slice Preparation

Male Sprague-Dawley rats, 9-11 months old, were anesthetized with ketamine (85 mg/kg of body weight, intramuscularly) and were decapitated in a cold room at 4° C. Brains were rapidly removed and placed into chilled (4° C.) oxygenated Krebs buffer (119.5 mM NaCl, 3.3 mM KCl, 1.3 mM $CaCl_2$, 1.2 mM $MgSO_4$, 25 mM $NaHCO_3$, 1.2 mM $KH_2PO_4$, 11 mM glucose, and 0.03 mM EDTA, pH 7.4) containing 1 mM ketamine and 15 μg/ml eserine. After removal of remaining meninges and chorioid plexus, 30 μm slices of striatum, hippocampus, and cortex were immediately prepared with a McIllwain tissue chopper, washed 3 times, and placed into custom-made superfusion chambers (Warner Instrument, Hamden, Conn.).

Superfusion and Electrical Stimulation.

Slices were equilibrated for 60 min at 37° C. by superfusing the chambers with oxygenated Krebs/ketamine/eserine buffer described above at a flow rate of 0.8 ml/min. Superfusion chambers contained two opposing silver mesh electrodes that were connected to an electrical stimulator (model S88; Grass Instruments). A custom-made polarity reversal device was used to prevent chamber polarization and also to monitor both the current and voltage 50 microseconds after the onset of each pulse to ensure uniform chamber resistance. After the equilibration period, slices were depolarized by perfusion with a high-K+ (52 mM) version of the Krebs/ketamine/eserine buffer in the presence or absence of 20 μM choline, 25 μM cytidine, and/or 25 μM uridine. Perfusates were collected during the entire 2-hour period and assayed for acetylcholine. Values were normalized for protein content of slices.

Results

Figure 22:
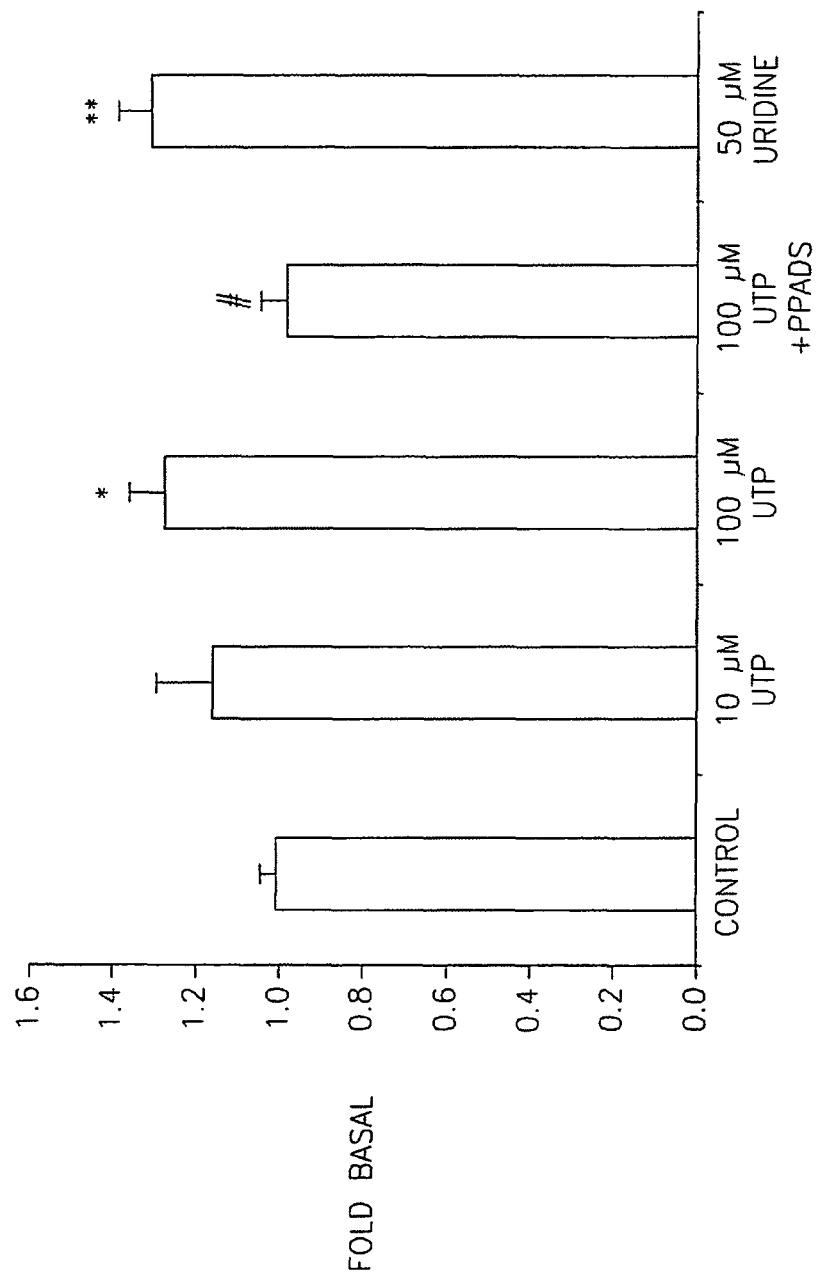
FIG. 22. Uridine and choline increase neurotransmitter release in striatal slices (top panel), hippocampal slices (middle panel), and cortical slices (top panel). Data are expressed as nanomoles per milligram protein per two hour, and depicted as means±SEM. "*"=P<0.001 relative to values obtained in the absence of choline. The first series in each panel was performed in the absence of choline; the second series was performed in the presence of choline. The bars in each series represent, from left to right, no additional compound added; cytidine added; and uridine added (each in addition to the choline, where appropriate).

To determine the effect of uridine and choline on acetylcholine release, slices of striatum, hippocampus, and cortex (n=8) were incubated in the presence or absence of choline and then depolarized, and acetylcholine release was measured. In some groups, cytidine or uridine was added as well. Choline increased acetylcholine release whether or not uridine was also present (FIG. 22).

These findings show that when neurons are repeatedly stimulated to release acetylcholine, choline increases the amount of neurotransmitter that is released, by replenishing stores of choline in membrane phospholipids (e.g. PC). The above Examples have shown that uridine augments synthesis of CDP-choline, which is then used to synthesize new PC. These findings and the findings of this Example show that the ability of neurons to synthesize new phospholipids, and thus repeatedly release neurotransmitters, is increased in an additive or synergistic fashion by addition of uridine together with choline.

Example 14

UMP Administration Improves Hippocampal-Dependent Memory Processing in EC and IC Rats Materials and Experimental Methods Animals Animals were maintained under standard environmental conditions (room temperature, 20-25° C.; relative humidity, 55-60%; light/dark schedule, 12/12). Seven pregnant Sprague Dawley rats (Charles River Laboratories) were obtained 1 wk prior to giving birth. At postnatal day 23, male pups were removed and separated into small groups and allowed to acclimatize for 1 wk. At this time, thirty-two rats were matched according to body weight, and assigned to either IC or EC conditions. One subgroup of IC rats (n=8) and one subgroup of EC rats (n=8) were given access to a control laboratory diet (Teklad Global 16% protein rodent diet, (Teklad diet 00217), Harlan Teklad, Madison, Wis.), while the remaining subgroups (n=8 each) received this diet supplemented with uridine-5'-monophosphate disodium (0.1% UMP-2Na+; Teklad diet 03273), corresponding to 200 mg/kg per day of UMP-2Na+, or approximately 132 mg/kg per day of uridine.

Rats were housed in the same rack in plastic cages (52× 32×20 cm high) with wire lids. Bedding and water were regularly changed, and animals were weighed each week, at which time general health assessments were made. Animals had ad libitum access to chow and water. EC rats were housed in groups of 2-3 animals Plastic toys (blocks, balls, PVC tubing, etc) placed in the EC cages were rotated between groups weekly; new toys were introduced monthly EC rats were taken to a "playroom" (12×6 ft; containing cabinets, desks, chairs, boxes, and toys) every other day for 45 min. The IC rats were housed individually, without toys, and handled three times per week to acclimatize the animals to experimenter handling and in order to alleviate fear and anxiety in subsequent behavioral training procedures. To avoid the typical weight gain caused by impoverished conditions (relative to enriched rats), IC rats were allowed to exercise three times per week for 15 min in an empty 4×6 ft room with only the experimenter present.

Animals were weighed weekly to ensure that UMP-treated and untreated rats were eating equivalent amounts of food. No significant differences in mean body weights were found between UMP-supplemented and control groups, showing that rats were eating equivalent amounts of diet whether it was supplemented with UMP or not. Also, as IC rats were exercised to avoid the weight gain that might otherwise occur (relative to EC rats), there was no difference in body weight between the EC and IC groups.

Water Maze Apparatus

A galvanized circular tank, 6 ft (185 cm) in diameter and 1.5 ft (0.55 cm) in height, was filled with water (25° C.+/−2° C.) to a depth of 20 cm and was located in a dimly-lit room containing several extra-maze cues. Four starting positions (north, south, east, west) were spaced around the perimeter of the tank, dividing the pool into four equal quadrants. For the visible platform version of the water maze, a white rubber ball (8 cm in diameter) was attached to the top of the submerged platform and protruded above the water surface. The platform could be used as a step to mount the ball to escape the water. A video camera was mounted directly above the water maze; this camera was linked to a computer With video tracking software to automatically record the escape latency (time to reach the platform), distance traveled (length of swim path taken to find the platform), and swim speed (HVS Image Ltd; Buckingham, UK).

Behavioral Procedures

Behavioral training was carried out between 10:00 AM-2:00 PM, in a blinded manner. Rats received a 4-d training session consisting of four trials (i.e., swims) per day to locate the hidden platform (1.5 cm below the water surface), which remained in the same position across trials for individual animals (i.e. within one of four quadrants). On each trial the animal was placed into the tank facing the wall at one of four designated start points (N, S, E, and W) and allowed to escape onto the hidden platform. A different starting point was used on each trial such that each starting point was used once each day. If an animal did not escape within 90 seconds, it was manually guided to the escape platform by the experimenter. After mounting the platform, rats remained on the platform for 20 seconds. Following each trial, animals were removed from the maze and placed in a holding cage for a 30 second inter-trial interval (ITI). The latency to mount the escape platform was used as a measure of task acquisition.

On day five, the rats were given a probe test. For this, the platform was removed and the swim path and time spent searching in the quadrant of the pool that previously contained the platform were measured over 60 s. This provides a measurement for the retention of spatial memory and indicates whether a spatial strategy was used during hidden platform training.

Statistical Analysis (this and the Following Example)

Results are expressed as means+/−S.E.M. Data were analyzed by ANOVA followed by Fisher's PLSD for post-hoc comparisons. Differences with a value of P<0.05 were considered significant.

Results

To determine the effect of oral UMP administration on hippocampal-dependent and/or cognitive memory processing, rats were exposed to either enriched (EC) or impoverished (IC) conditions for three months, and rats exposed to each condition were administered a control or UMP-enriched diet, then administered a hidden platform water maze task. The performance of all rats improved over the course of four days of training in the hidden platform water maze task (FIG. 23A), as evidenced by a significant main effect of blocks of trials (ANOVA analysis; P<0.001). Also, a main effect of group (P<0.01), and a significant group x diet interaction (P<0.05) were observed. IC-UMP and EC rats treated with either diet acquired the task at a significantly faster rate than did IC-CONT rats (IC rats administered a control diet) (post-hoc analysis; P<0.05). Moreover, EC rats treated with UMP acquired the task at a faster rate than EC-CONT rats (P<0.09). Thus, chronic dietary treatment with UMP prevents impairments caused by impoverished environmental conditions in spatial and/or cognitive memory and intelligence and improves spatial and/or cognitive memory and intelligence in healthy subjects.

Figure 23:
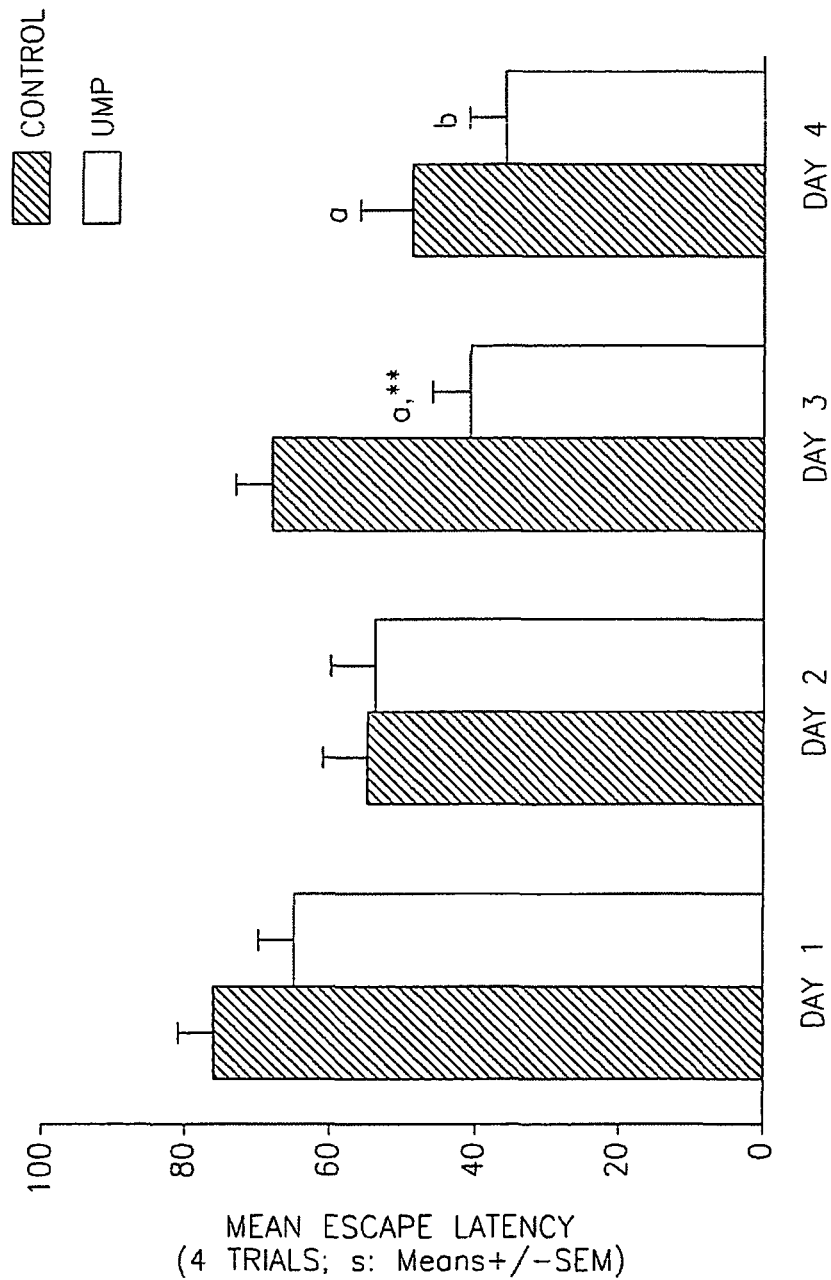
FIG. 23. The effects of environment and of a UMP-supplemented diet on memory for a hippocampal-dependent hidden platform water maze task. Untreated IC rats (IC-CONT), compared to EC rats (EC-CONT and EC-UMP) or IC rats treated with a diet high in UMP (IC-UMP), acquired the hidden platform water maze task at a slower rate (left panel) and, during the probe test, spent less time in the quadrant that had originally contained the platform (right panel). Error bars represent the SEM.

In addition, a probe test was administered to the rats. Overall, the rats spent more time in the quadrant that originally contained the platform, suggesting that all animals used spatial skills to some degree to acquire the hidden platform task (FIG. 23B). IC-UMP and treated or untreated EC rats spent significantly more time in the correct quadrant than IC-CONT rats did (ANOVA; p<0.01) during the 60 s probe test, providing further evidence that chronic dietary treatment with UMP prevents the impairments caused by impoverished environmental conditions in spatial and/or cognitive memory and intelligence and improves spatial and/or cognitive memory and intelligence in healthy subjects.

Example 15

UMP Administration does not Improve Striatal-Dependent Memory Processing in EC and IC Rats Materials and Experimental Methods Visible Water Maze Task One week after completion of the 4-day/4 trials per day spatial training task, the rats from the above Example received four training sessions consisting of four trials (i.e., swims) per day. On each trial the animal was placed into the tank facing the wall at one of four designated start points (N, S, E, and W) and allowed to escape onto the visibly cued platform. A different starting point was used on each trial such that each starting point was used each day. In addition, the visible escape platform was placed in a different quadrant on each trial such that each of the four quadrants contained the escape platform once each day. If an animal did not escape within 90 sec, it was manually guided to the escape platform by the experimenter. After mounting the platform, rats remained on the platform for 20 sec. Following each trial, animals were removed from the maze and placed in a holding cage for a 30-sec ITI.

Results

Figure 24:
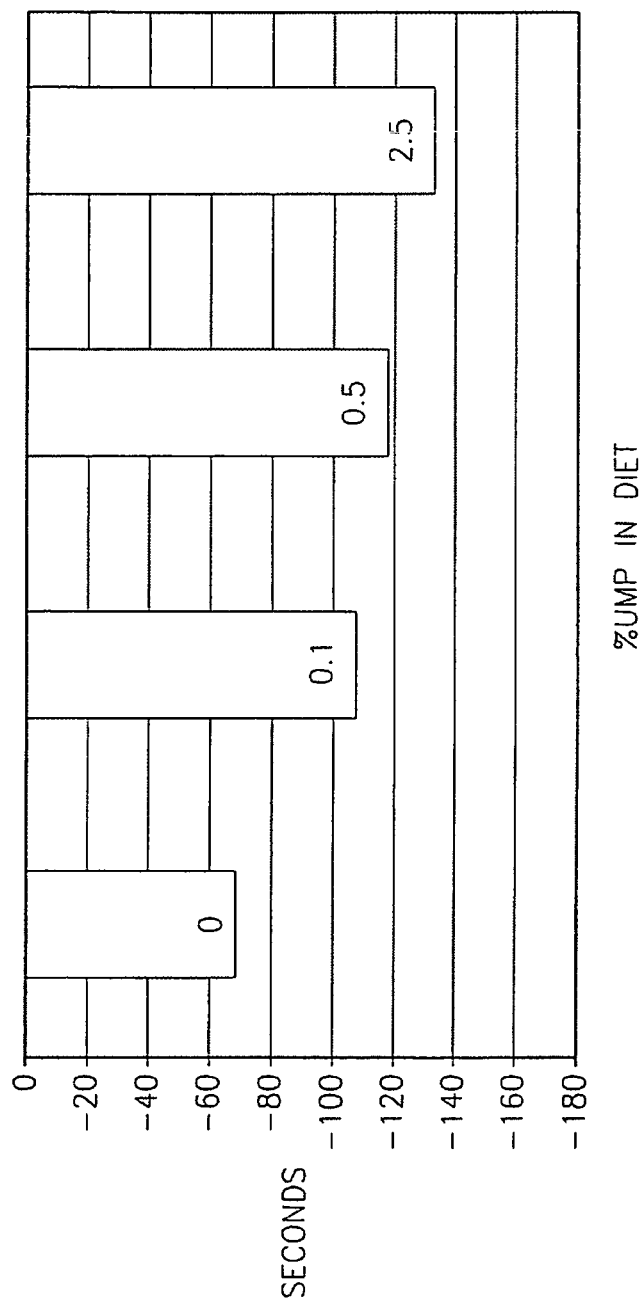
FIG. 24. Effects of environment and of a UMP-supplemented diet on memory for a striatal-dependent visible platform water maze task. All rats acquired the visible platform water maze task equal rates.
Figure 26A:
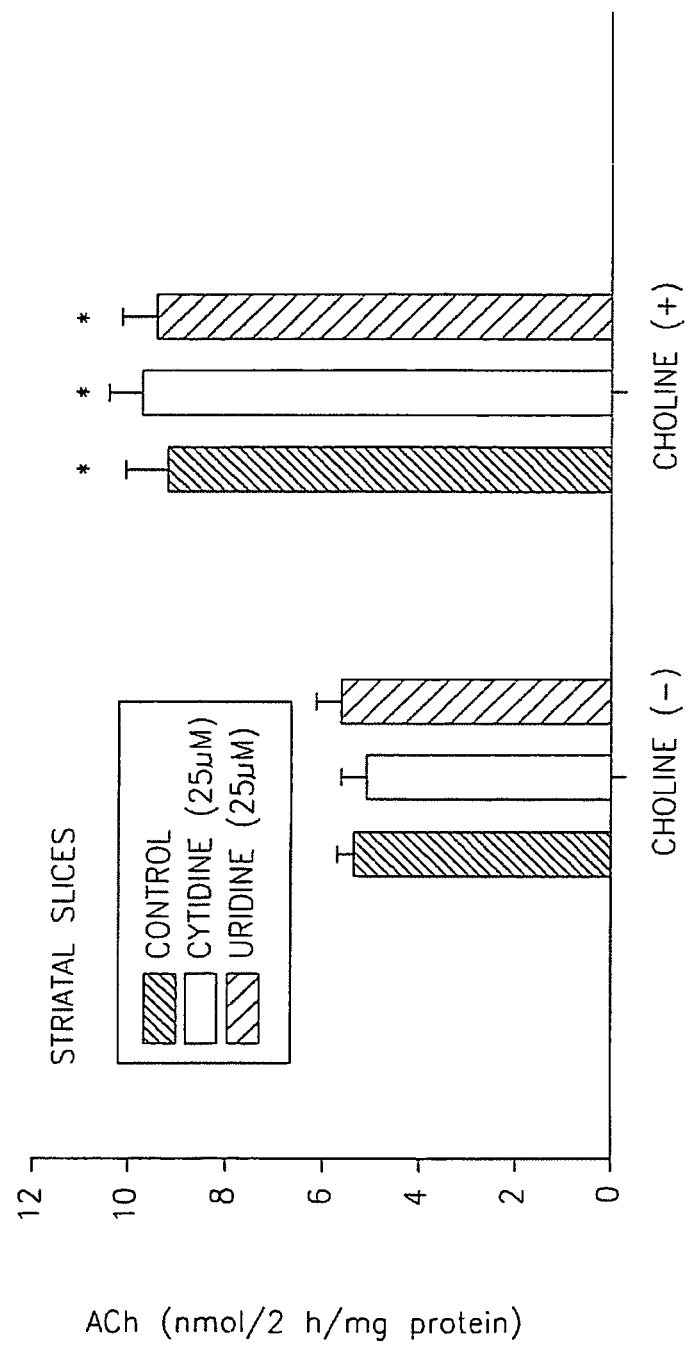
Figure 26B:
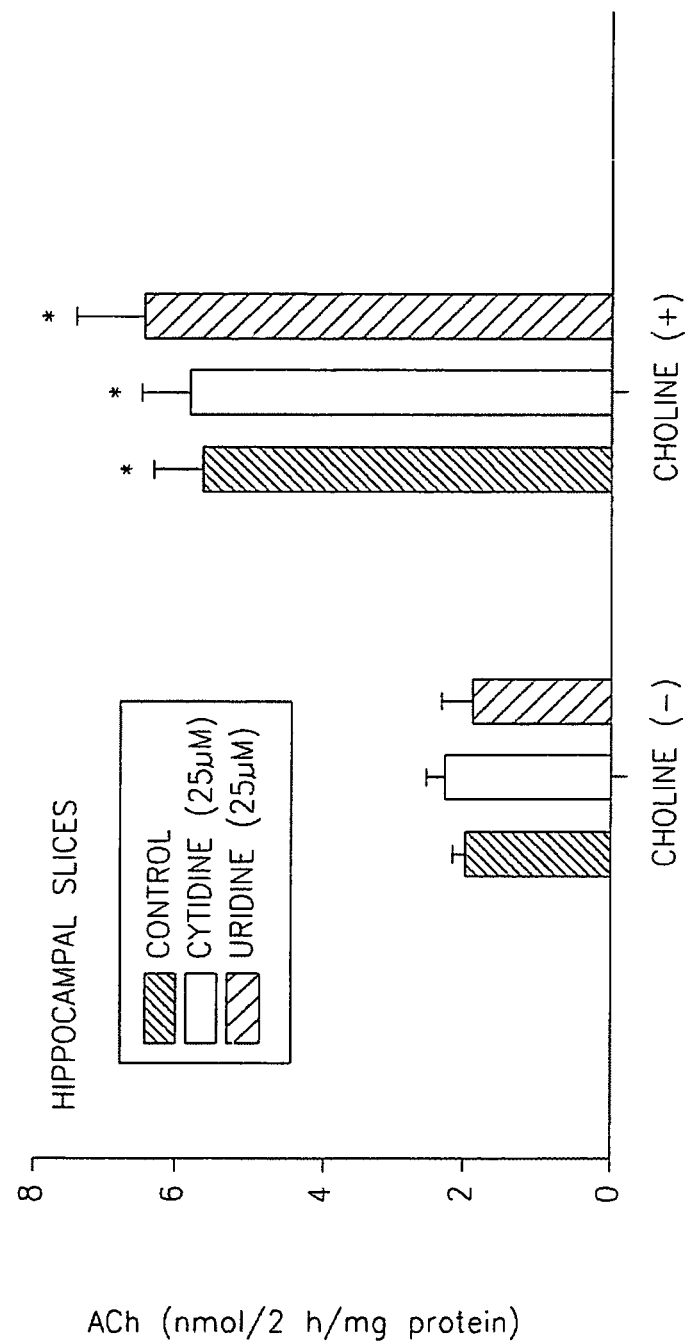
Figure 26C:
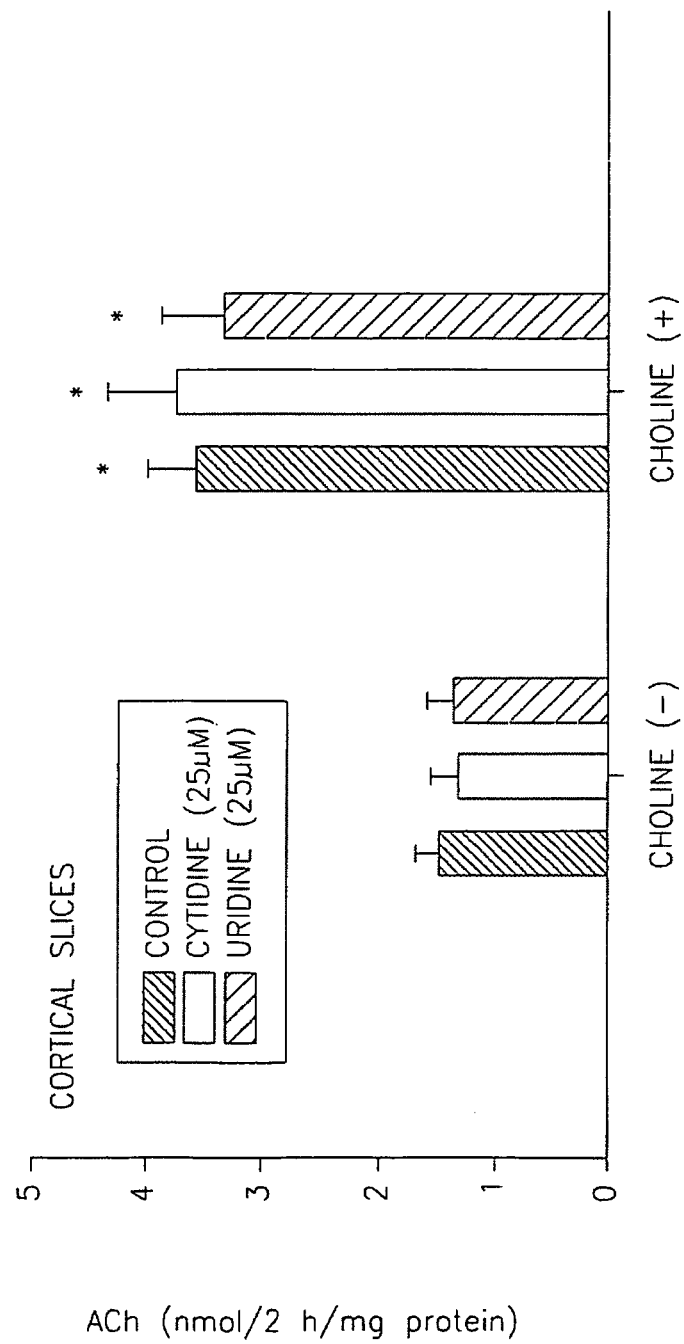

To determine the effect of oral UMP administration on striatal-dependent memory processing, rats were treated as in the previous Example and administered a visible platform water maze task are shown in FIG. 24. Performance of rats improved over the course of 4 days of training, as evidenced by a significant main effect of blocks of trials (ANOVA analysis; $P<0.001$). No other significant main effects were observed, indicating that environment and a UMP-supplemented diet have little or no effect on striatal-based (stimulus-response) memory.

What is claimed is:

1. A method of stimulating or enhancing a neurite outgrowth or branching of a neural cell of a subject in need thereof in the presence of NGF, comprising orally administering to said subject a composition comprising (a) between about 20 mg and about 1.5 g per day of uridine, an acyl derivative thereof, a uridine phosphate, or a salt of said uridine, acyl derivative thereof, or uridine phosphate; and (b) a choline source, a choline ester, a choline phosphate, a choline precursor or a choline salt, thereby stimulating or enhancing a neurite outgrowth or branching of a neural cell of a subject.

2. The method of claim 1, wherein said uridine phosphate is a uridine-5'-monophosphate (UMP), uridine-5'-diphosphate (UDP), uridine-5'-triphosphate (UTP), or is a salt of said UMP, UDP, or UTP.

3. The method of claim 1, wherein said choline salt is choline chloride, choline bitartrate, or choline stearate.

4. The method of claim 1, wherein said composition is administered for no less than 4 days.

5. The method of claim 1, wherein said uridine phosphate is uridine-5'-monophosphate (UMP).

6. The method of claim 1, wherein the composition is administered for a minimum period of about 6 weeks.

* * * * *